US009713591B2

(12) United States Patent
Barenholz et al.

(10) Patent No.: US 9,713,591 B2
(45) Date of Patent: Jul. 25, 2017

(54) COMPOSITION OF MATTER COMPRISING LIPOSOMES EMBEDDED IN A POLYMERIC MATRIX AND METHODS OF USING SAME

(75) Inventors: Yechezkel Barenholz, Jerusalem (IL); Rivka Cohen, Jerusalem (IL)

(73) Assignee: Yissum Research Development Company of the Hebrew University of Jerusalem, LTD., Jerusalem (IL)

( * ) Notice: Subject to any disclaimer, the term of this patent is extended or adjusted under 35 U.S.C. 154(b) by 286 days.

(21) Appl. No.: 13/123,130

(22) PCT Filed: Oct. 11, 2009

(86) PCT No.: PCT/IL2009/000967
§ 371 (c)(1),
(2), (4) Date: Jun. 22, 2011

(87) PCT Pub. No.: WO2010/041256
PCT Pub. Date: Apr. 15, 2010

(65) Prior Publication Data
US 2011/0244029 A1    Oct. 6, 2011

Related U.S. Application Data

(60) Provisional application No. 61/103,440, filed on Oct. 7, 2008.

(51) Int. Cl.
    *A61K 9/127*     (2006.01)
    *A61K 31/445*    (2006.01)
    *A61K 31/573*    (2006.01)

(52) U.S. Cl.
    CPC .......... *A61K 9/127* (2013.01); *A61K 31/445* (2013.01); *A61K 31/573* (2013.01)

(58) Field of Classification Search
    USPC ........................................................ 424/450
    See application file for complete search history.

(56) References Cited

U.S. PATENT DOCUMENTS

| | | | |
|---|---|---|---|
| 4,837,028 A | | 6/1989 | Allen |
| 4,877,619 A | * | 10/1989 | Richer .................... 424/1.21 |
| 4,900,556 A | * | 2/1990 | Wheatley et al. ......... 424/450 |
| 4,921,757 A | * | 5/1990 | Wheatley et al. ........ 428/402.2 |
| 5,009,819 A | * | 4/1991 | Popescu et al. ............. 264/4.1 |
| 5,192,549 A | | 3/1993 | Barenolz et al. |
| 5,316,771 A | | 5/1994 | Barenholz et al. |
| 5,616,341 A | | 4/1997 | Mayer et al. |
| 5,736,155 A | | 4/1998 | Bally et al. |
| 5,785,987 A | | 7/1998 | Hope et al. |
| 6,045,824 A | | 4/2000 | Kim et al. |
| 6,162,462 A | * | 12/2000 | Bolotin ............... A61K 31/445 264/4.1 |
| 6,348,213 B1 | | 2/2002 | Barenholz et al. |
| 6,451,543 B1 | | 9/2002 | Kochendoerfer et al. |
| 6,713,533 B1 | * | 3/2004 | Panzner ...................... 523/202 |
| 8,268,347 B1 | * | 9/2012 | Cipolla et al. ............. 424/450 |
| 2003/0235610 A1 | * | 12/2003 | McLean ............... A61K 9/1277 424/450 |
| 2004/0052857 A1 | * | 3/2004 | Keating ................... B82Y 5/00 424/490 |
| 2004/0224012 A1 | * | 11/2004 | Suvanprakorn et al. ..... 424/450 |
| 2004/0258747 A1 | * | 12/2004 | Ponzoni .............. A61K 31/704 424/450 |
| 2006/0141021 A1 | * | 6/2006 | Wang et al. .................. 424/450 |
| 2006/0165766 A1 | | 7/2006 | Barenholz et al. |
| 2006/0222694 A1 | | 10/2006 | Oh et al. |
| 2006/0239925 A1 | * | 10/2006 | Wada et al. ................. 424/9.45 |

(Continued)

FOREIGN PATENT DOCUMENTS

| | | |
|---|---|---|
| WO | 01/60339 A2 | 8/2001 |
| WO | 03/000227 A2 | 1/2003 |
| WO | 2006/001815 A1 | 1/2006 |

OTHER PUBLICATIONS

Avnir et al., "Amphipathic Weak Acid Glucocorticoid Prodrugs Remote-Loaded Into Sterically Stabilized Nanoliposomes Evaluated in Arthritic Rats and in a Beagle Dog—A Novel Approach to Treating Autoimmune Arthritis", Arthritis & Rheumatism, vol. 58, No. 1, Jan. 2008, pp. 119-129.

Bangham et al., "Diffusion of Univalent Ions across the Lamellae of Swollen Phospholipids", J. Mol. Biol. (1965) 13, pp. 238-252.

Clerc et al., "Loading of amphipathic weak acids into liposomes in response to transmembrane calcium acetate gradients", Biochimica et Biophysica Acta 1240 (1995) pp. 257-265.

Dai et al., "Preparation and characterization of liposomes-in-alginate (LIA) for protein delivery system", Colloids and Surfaces B: Biointerlaces 47 (2006), pp. 205-210.

(Continued)

*Primary Examiner* — Gollamudi Kishore

(74) *Attorney, Agent, or Firm* — Greenberg Traurig LLP

(57) ABSTRACT

The present disclosure provides a composition of matter comprising liposomes encapsulating in their intraliposomal aqueous compartment at least one active agent, the liposomes having a diameter of at least 200 nm and being embedded in a water insoluble, water absorbed cross-linked polymeric matrix. In one embodiment, the composition of matter is held within an aqueous medium, preferably being in iso-osmotic equilibrium with the intraliposomal aqueous compartments of the liposomes. The present disclosure also provides a method of removal of non-encapsulated active agent from the composition of matter, a method of preparing said composition of matter, a pharmaceutical composition comprising said composition of matter, use of such composition of matter; a method of providing prolonged delivery of a active agent to a subject in need thereof by administering to said subject the composition of matter disclosed herein as well as a package comprising said composition of matter held within said aqueous medium and instructions for use thereof.

7 Claims, 19 Drawing Sheets

(56) References Cited

U.S. PATENT DOCUMENTS

2009/0162425 A1 6/2009 Divi et al.

OTHER PUBLICATIONS

Garbuzenko et al., "Electrostatics of PEGylated Micelles and Liposomes Containing Charged and Neutral Lipopolymers", Langmuir 2005, 21, pp. 2560-2568.

Grant et al., "DRV Liposomal Bupivacaine: Preparation, Characterization, and In Vivo Evaluation in Mice", Pharmaceutical Research, vol. 18, No. 3, 2001, pp. 336-343.

Grant et al., "A Novel Liposomal Bupivacaine Formulation to Produce Ultralong-Acting Analgesia", Anesthesiology 2004; 101; pp. 133-137.

Haran et al., "Transmembrane ammonium sulfate gradients in liposomes produce efficient and stable entrapment of amphipathic weak bases", Biochimica et Biophysica Acta, 1151 (1993) pp. 201-215.

Hertz et al., "Permeability and Integrity Properties of Lecithin-Sphingomyelin Liposomes", Chemistry and Physics of Lipids 15 (1975), pp. 138-156.

Kirby et al., "Dehydration-Rehydration Vesicles: A Simple Method for High Yield Drug Entrapment in Liposomes", Bio/Technology Nov. 1984, pp. 979-984.

Machluf et al., "Characterization of microencapsulated liposome systems for the controlled delivery of liposome-associated macromolecules", Journal of Controlled Release 43 (1996), pp. 35-45.

George et al., "Polyionic hydrocolloids for the intestinal delivery of protein drugs: Alginate and chitosan—a review", Journal of Controlled Release 114 (2006), pp. 1-14.

Shew et al., "A novel method for encapsulation of macromolecules in liposomes", Biochimica et Biophysica Acta 816 (1985), pp. 1-8.

Swarbrick et al., "Encyclopedia of Pharmaceutical Technology", vol. 9, Liposomes as Pharmaceutical Dosage Forms to Microencapsulation, 1994.

Szoka et al., "Procedure for preparation of liposomes with large internal aqueous space and high capture by reverse-phase evaporation", Proc. Natl. Acad. Sci. USA, vol. 75, No. 9, pp. 4194-4198, Sep. 1978.

Zucker et al., "Liposome drugs' loading efficiency: A working model based on loading conditions and drug's physicochemical properties", Journal of Controlled Release 139 (2009), pp. 73-80.

* cited by examiner

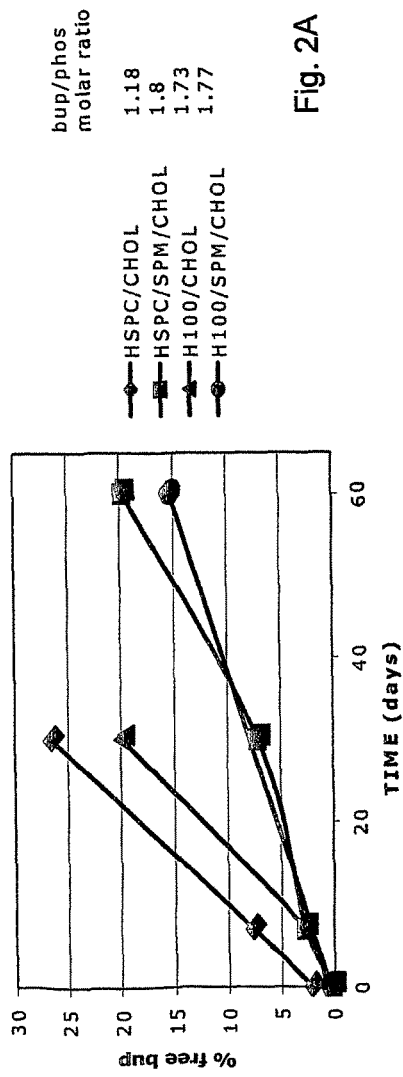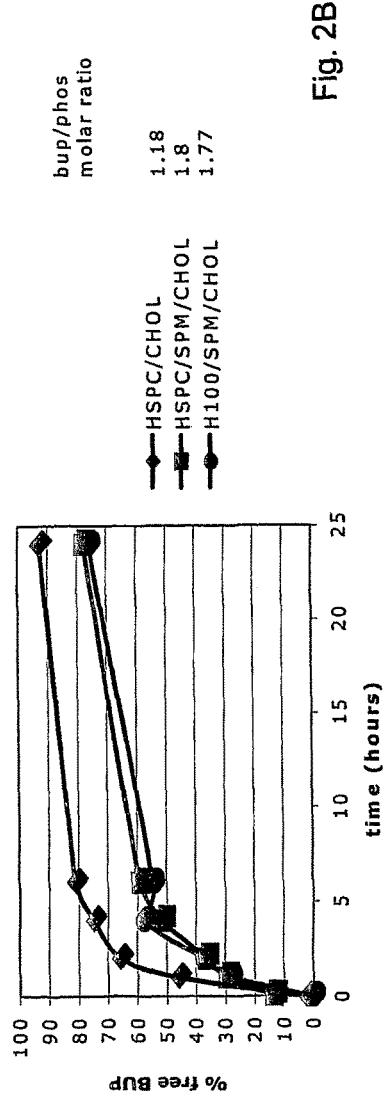

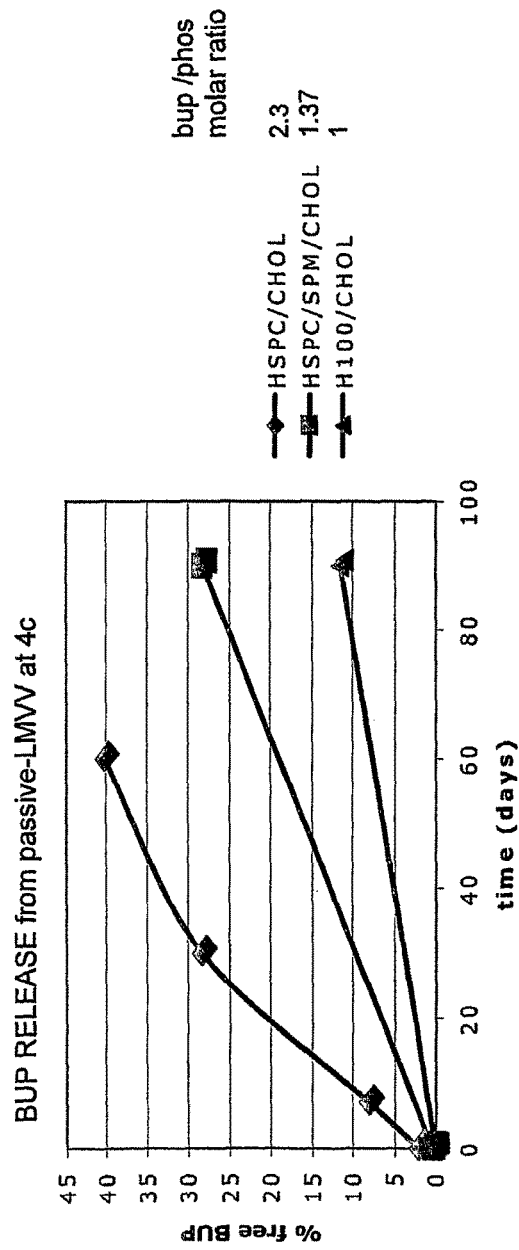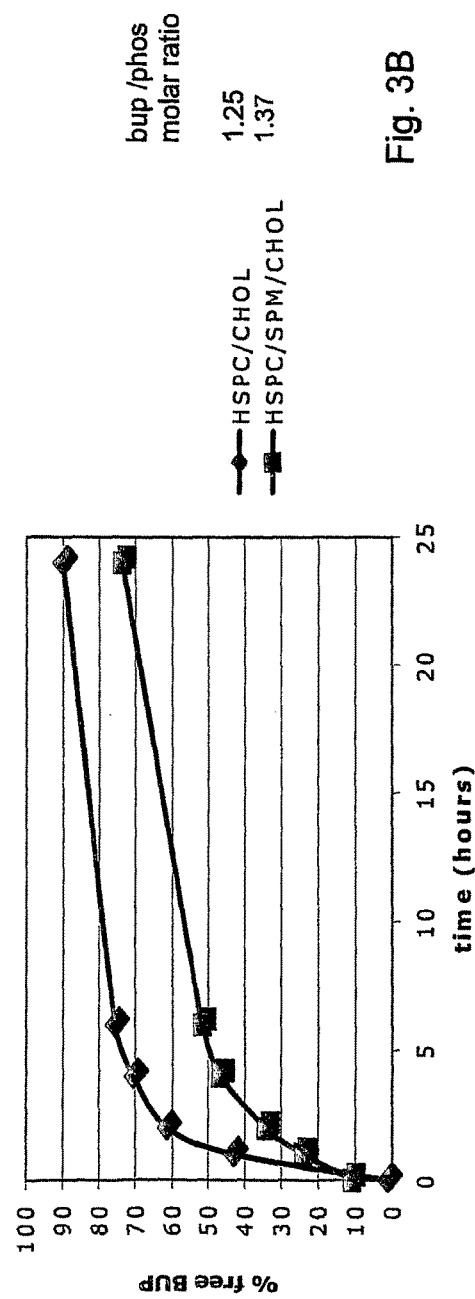
Fig. 3A
Fig. 3B washed ALG-LMVV-BUP beads with saline

Fig. 10A washed ALG-LMVV-BUP beads with saline

Fig. 10B

COMPOSITION OF MATTER COMPRISING LIPOSOMES EMBEDDED IN A POLYMERIC MATRIX AND METHODS OF USING SAME

RELATED APPLICATIONS

This application is a national phase filing under 35 U.S.C. 371 of International Application No. PCT/IL2009/000967, filed on Oct. 11, 2009, and claims the benefit of U.S. Provisional Application Ser. No. 61/103,440, filed Oct. 7, 2008, the entirety of these applications are hereby incorporated herein by reference for the teachings therein.

FIELD OF THE INVENTION

The present disclosure is in the field of biochemistry and in particular to compositions of matter comprising a combination of polymers and liposomes for carrying active agents.

BACKGROUND OF THE INVENTION

Among other applications, liposomes are used as carriers of drugs for delivery via a plurality of mechanisms. To this end, various types of liposomes are used, from small unilamellar vesicles (SUV), large unilamellar vesicles (LUV), multilamellar vesicles (MLV), multivesicular vesicles (MVV), large multivesicular vesicles (LMVV, also referred to, at times, by the term giant multivesicular vesicles, "GMV"), oligolamellar vesicles (OLV), and others. It is appreciated by those versed in the art that LMVV are somewhat different from unilamellar vesicles of various sizes and of the "onion like" MLV structure. In LMVV the amount of aqueous medium forming the aqueous phase per the amount of lipid is greater than that in MLV, this potentially allowing higher amount of drug to be loaded into the aqueous phase, namely, higher drug to lipid mole ratio in the LMVV when compared to MLV system of similar size distribution. This difference was exemplified by Grant et al. 2004 [Anesthesiology 101(1):133-7, 2004] and in U.S. Pat. No. 6,162,462. It has been found that the difference in structure between MLV an LMVV not only allows higher loading of the drug into the liposomes but also a prolonged release of the drug from the LMVV system.

Specifically, U.S. Pat. No. 6,162,462 discloses liposomal bupivacaine compositions in which the bupivacaine is loaded by a transmembrane ammonium sulfate gradient, the liposomes being giant multivesicular vesicles (GMV, a synonym for LMVV) having a mole ratio of encapsulated drug to lipid in said liposomal composition of at least 1.0. A specific drug encapsulated in the liposomes of U.S. Pat. No. 6,162,462 is the amphipathic analgesic drug bupivacaine (BUP). These bupivacaine loaded LMVV have shown to be provide superior analgesia in mice and humans [Grant et al. 2004, ibid. and U.S. Pat. No. 6,162,462]. However a phenomenon that still remains unresolved with these LMVV relates to leakage of bupivacaine from the LMVV during storage at 4° C. or room temperature. Thus, after time, free drug is contained in the composition of matter (the amount may be above drug MTD) and the administration of the composition of matter containing such free drug may result in toxicity and unwanted side effects (from exposure high amounts of free drug), unfavorable pharmacokinetics and shorter duration of the therapeutic effect. Thus, there is a need in the art to provide a composition of matter where leakage of drug from liposomes encapsulating same during storage is reduced or prevented.

SUMMARY OF THE INVENTION

The present disclosure provides, in accordance with a first of its aspects, a composition of matter comprising liposomes encapsulating in their intraliposomal aqueous compartment at least one active agent, the liposomes having a diameter of at least 200 nm and being embedded in a water insoluble, water absorbed cross-linked polymeric matrix. In one embodiment, this composition of matter is held in an aqueous medium, e.g. a storing medium. It has been found and shown herein that keeping the composition of matter in a suitable aqueous medium, as further defined herein, significantly reduces the amount of material that leaks from the liposomes.

Also provided by the present disclosure is a method of preparing a composition of matter comprising liposomes encapsulating in their intraliposomal aqueous compartment at least one active agent, the liposomes having a diameter of at least 200 nm and being embedded in a cross-linked water insoluble and water absorbed polymeric matrix, the method comprising mixing (i) liposomes encapsulating in their intraliposomal aqueous compartment at least one active agent, the liposomes having a diameter of at least 200 nm; (ii) at least one cross-linkable polymer; and (iii) an aqueous solution comprising a cross-linker capable of forming with said cross-linkable polymer a water insoluble, water absorbed cross-linked polymer having embedded therein said liposomes.

Also provided herein is a method for removal of non-encapsulated active agent from a composition of matter comprising liposomes encapsulating in their intraliposomal aqueous compartment at least one such active agent, the liposomes having a diameter of at least 200 nm and being embedded in a cross-linked water insoluble and water absorbed polymeric matrix, the composition of matter being held in an aqueous medium, the method comprising decanting at least part of said aqueous medium from said composition of matter, thereby removing from said composition of matter at least part of non-encapsulated active agent. This method is applicable both for removing non-encapsulated material, e.g. following preparation, as well as removal of any material that has leaked from the composition of matter, e.g. during or following storage. As shown hereinbelow, after a period of three months storage leakage has been significantly reduced as compared to the same liposomes which have not been embedded in a polymeric matrix.

The present disclosure also provide a composition of matter prepared by any of the above recited methods. In one embodiment, once the aqueous medium is decanted, the composition of matter comprises less than 10% non-encapsulated (free) active agent.

The present disclosure also provides pharmaceutical composition comprising as an active ingredient a composition of matter as disclosed herein as well as the use of the composition of matter as disclosed herein for the preparation of a pharmaceutical composition.

Finally, the present disclosure provides methods for providing prolonged delivery of a active agent to a subject in need thereof, the method comprising administering to said subject said composition of matter or a pharmaceutical composition comprising the same. Of particular interest it the method for providing prolonged analgesia. In this embodiment, the active agent is an analgesic drug.

Finally, the present disclosure provides a package (or kit) comprising at least one container comprising an aqueous medium holding a composition of matter as disclosed herein or a pharmaceutical composition comprising the same and instructions for decanting said aqueous medium prior to use of said composition of matter to form, e.g. an administrable composition of matter.

BRIEF DESCRIPTION OF THE DRAWINGS

In order to understand the invention and to see how it may be carried out in practice, embodiments will now be described, by way of non-limiting example only, with reference to the accompanying drawings, in which:

(FIG. 1A) or at 37° C. (FIG. 1B), from large multivesicular vesicles (LMVV) of different lipid compositions (BUP to phospholipid mole ratio of each is given) which have been loaded with BUP using remote loading driven by trans-membrane ammonium sulphate (AS) gradient.

FIGS. 2A-2B are graphs showing the release of Bupivacaine (BUP), during storage at 4° C. (FIG. 2A) or at 37° C. (FIG. 2B), from large multivesicular vesicles (LMVV) of different lipid compositions (BUP to phospholipid mole ratio of each is given) which have been loaded with BUP using remote loading driven by trans-membrane calcium acetate (CA) gradient.

FIGS. 3A-3B are graphs showing the release of Bupivacaine (BUP), during storage at 4° C. (FIG. 3A) or at 37° C. (FIG. 3B), from LMVV of different lipid compositions (HSPC/CHOL 6/4 mole ratio; HSPC/C16SPM/CHOL 3/3/4 mole ratio; and HSPC100/CHOL 6/4 mole ratio, BUP to phospholipid mole ratio of each composition is given) which have been loaded with BUP using the passive loading approach.

FIG. 5B showing the effect of 5 different LMVV formulations, the amount of BUP being constant 3 mg; and FIG. 5C which describes a comparison of the eight different LMVV formulations (Table 8) at a dose of 3 mg/mouse.

FIG. 6A comparing the effect of lip 2 (3 and 6 mg BUP/mouse), FIG. 6B comparing the effect of lip 3 (3 and 6 mg BUP/mouse), FIG. 6C comparing the effect of lip 4 (3 and 4.5 mg BUP/mouse), FIG. 6D comparing the effect of lip 5 (3 and 6 mg BUP), FIG. 6E comparing the effect of lip 8 (3 and 6 mg BUP/mouse), and FIG. 6F comparing the effect of free (non liposomal) BUP at 0.375 mg/mouse using two volumes (150 and 300 μl) and 0.75 mg/mouse at a volume of 150 μl.

FIGS. 9A-9B shows the average effect of storage (6 months) in saline, 0.2%, 0.5%, or 2.0% Bup solutions (average of different batches of ALG-Beads produced according to the methods of the invention). FIG. 9C shows the average effect of storage (3 months) in saline 0.5%, 2.0% Bup solutions. FIGS. 9D to 9F describe and compare the change in level of free Bup (% free Bup in the different storage media) during storage at 4° C. of the different batches (herein denoted as A, B, C, D, E and an average plot) of LMVV (HSPC100/C16SPM/CHOL having 3/3/4 mole ratio) loaded with Bup using AS trans-membrane gradient embedded in Ca-crosslinked alginate hydrogel when stored in various storage media, during 3 months: saline (FIG. 9D), 0.5% BUP (FIG. 9E) and 2.0% BUP (FIG. 9F). FIGS. 9G-9K describe and compare the change in level of free Bup (% of free Bup in the different storage media) during storage at 4° C. of the different batches (herein denoted as A, B, C, D, E and an average plot) LMVV (HSPC100/C16SPM/CHOL having 3/3/4 mole ratio) loaded with Bup using AS trans-membrane gradient embedded in Ca-crosslinked alginate hydrogel when stored in various storage media, during 3 months in: saline (FIG. 9G), in 0.2% BUP (FIG. 9H), in 0.5% BUP (FIG. 9I) or in 2.0% BUP (FIG. 9J). FIG. 9K describes the average effect of storage (3 months) in saline, 0.2%, 0.5%, or 2.0% Bup solutions (average of different batches of ALG-Beads described in FIG. 9G to 9J). FIG. 9L shows the average effect of storage (2 months) in saline 0.5%, 2.0% Bup solutions. (FIGS. 9M, 9N and 9O in saline, 0.5%, or 2.0% Bup solutions and FIG. 9P in saline, 0.2%, 0.5%, or 2.0% Bup solutions). FIG. 9Q describes a separate experiment of 2 months follow-up upon storage in saline without hydrogel. All storage media in FIGS. 9A-9Q were brought to 285 mOsmole by addition of NaCl solution to retain iso-tonicity FIG. 10A-10D describe the change in level of free Bup (% of free Bup in storage media) in different storage media of LMVV (HSPC100/C16SPM/CHOL3/3/4 mole ratio) loaded with Bup via trans-membrane AS gradient and embedded in Ca cross-linked alginate. Three storage media were used (saline, 0.5% Bup, and 2.0% Bup, all storage media were brought to iso-tonicity of 285 mOsmole with NaCl solution). These were stored for 40 days at 4° C. and than used in the experiments described in FIG. 10A-10D). FIGS. 10A and 10B describe release of Bup after the removal of storage media by washing with saline followed by 30 hours of incubation at 37° C. throughout this time amount of drug in the hydrogel media (saline) was measured (FIG. 10A) and also described as % Bup released (FIG. 10B). FIG. 10E shows the change in Bup concentration in 0.5% Bup, and 2.0% Bup storage media of the above described Bup loaded LMVV after incubation at a temperature of 25° C. for 20 days.

FIG. 11E summarizes the changes in Bup concentration over a storage period of 3 months at 4° C., in different liquid storage media of CHT-LMVV-BUP (HSPC100/C16SPM/CHOL 3/3/4 mole ratio), remote loaded by trans-membrane AS gradient. The storage media used were: Saline, 0.2% BUP, 0.5% BUP, and 2.0% BUP.

DETAILED DESCRIPTION OF SOME NON-LIMITING EMBODIMENTS

Figure 1A:
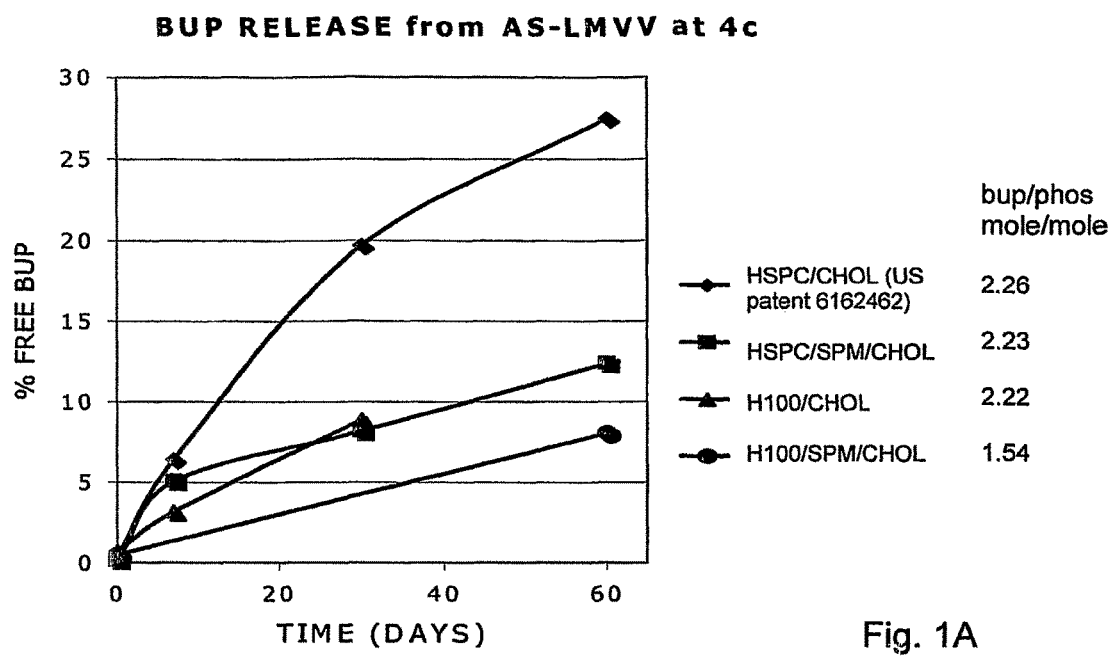
FIGS. 1A-1B are graphs showing the release of Bupivacaine (BUP), during storage at 4° C.

The present invention is based on the understanding that existing bupivacaine liposomal formulations such as those described in U.S. Pat. No. 6,162,462 and by Grant et al. [Grant et al. 2004, ibid.] have a tendency to leak drug during long term storage at low temperatures which may impose a risk of toxicity when administered to subjects in need of the drug. These bupivacaine liposomal formulations contained high drug to phospholipid (drug/PL) ratio (>0.5 mole/mole) in large multivesicular vesicle (LMVV, referred to in U.S. Pat. No. 6,162,462 as giant multivesicular vesicles, GMV), albeit, following storage, a substantial amount of the a priori encapsulated drug was found to be in the external medium. Thus, a novel composition of matter was designed to allow the easy removal of any non-encapsulated drug from a composition of matter, in case such leakage took place following storage of the composition of matter.

Specifically, it has been found that large liposomes, having a diameter of at least 200 nm (such as large multivesicular vesicles, LMVV) and being embedded in a cross-linked, water insoluble, water absorbed polymeric matrix, can be stored in an aqueous medium; and following storage (e.g. just before use) any leaked drug (which is thus dissolved in the aqueous storage medium), can be removed from the composition of matter by simple decanting (e.g. pouring, withdrawing, e.g. with a pipette, or funnel) the aqueous storage medium from the composition of matter. Without being bound by theory, it is believed that due to the size of the liposomes and their stable entrapment (capture) of the liposome loaded agent in the cross linked polymeric matrix, while the non-encapsulated drug, freely dissolved in the storage aqueous medium may be (almost fully) removed from the composition of matter once the aqueous medium, or at least a portion thereof, is withdrawn from the composition of matter.

Thus, in accordance with a first of its aspects, the present invention provides a composition of matter comprising liposomes encapsulating in their intraliposomal aqueous compartment at least one active agent, the liposomes having a diameter of at least 200 nm and being embedded in a water insoluble, water absorbed cross-linked polymeric matrix. As will be shown herein, the polymeric matrix is typically a hydrogel.

Two unique features are provided by the present invention. First, the embedment of liposomes in a hydrogel or hydrogel like matrix (cross-linked water absorbed and water insoluble polymeric matrix as defined herein) reduces dramatically the leakage of active agent (e.g. drug) from the liposome and also prevents a change in the agent to phospholipid ratio in the liposomal formulation per se.

In one embodiment, the composition of matter is held in an aqueous medium. Such composition of matter held in the aqueous medium (having characteristics as defined herein) is suitable and ready for long term storage, as will be further described below. It is important to note that the amount of aqueous medium is such that when in a container, the aqueous medium preferably totally covers the water absorbed polymeric matrix, i.e. it is in excess compared to the water absorbed polymeric matrix. In fact, when viewing the container it appears to have two phases, one of the water absorbed polymeric matrix and the other of the aqueous medium covering it.

As used herein, the term "liposomes" denotes a system comprising an organized collection of lipids forming at least one type of liposomes, and enclosing at least one intraliposomal aqueous compartment.

As used herein, the term "composition of matter" encompasses at least the combination of liposomes having a size of at least 200 nm and being embedded in a matrix composed of at least one cross-linked (partially or fully) water immiscible, water absorbed polymer.

The liposomes within the composition of matter comprise at least one liposome forming lipid, which forms the liposomes' membrane. The liposomes' membrane is a bilayer membrane and may be prepared to include a variety of physiologically acceptable liposome forming lipids and, as further detailed below, non-liposome forming lipids (at the mole ratio which support the formation and maintenance of stable liposomes.

As used herein, the term "liposome forming lipids" is used to denote primarily glycerophospholipids and sphingomyelins which when dispersed in aqueous media by itself at a temperature above their solid ordered to liquid disordered phase transition temperature will form stable liposomes. The glycerophospholipids have a glycerol backbone wherein at least one, preferably two, of the hydroxyl groups at the head group is substituted by one or two of an acyl, alkyl or alkenyl chain, and the third hydroxyl group is substituted by a phosphate (phosphatidic acid) or a phosphoestar such as phosphocholine group (as exemplified in phosphatidylcholine), being the polar head group of the glycerophospholipid or combination of any of the above, and/or derivatives of same and may contain a chemically reactive group (such as an amine, acid, ester, aldehyde or alcohol). The sphingomyelins consists of a ceramide (N-acyl sphingosine) unit having a phosphocholine moiety attached to position 1 as the polar head group.

In the liposome forming lipids, which form the matrix of the liposome membrane the acyl chain(s) are typically between 14 to about 24 carbon atoms in length, and have varying degrees of unsaturation or being fully saturated being fully, partially or non-hydrogenated lipids. Further, the lipid matrix may be of natural source (e.g. naturally occurring phospholipids), semi-synthetic or fully synthetic lipid, as well as electrically neutral, negatively or positively charged.

Examples of liposome forming glycerophospholipids include, without being limited thereto, glycerophospholipid. phosphatidylglycerols (PG) including dimyristoyl phosphatidylglycerol (DMPG); phosphatidylcholine (PC), including egg yolk phosphatidylcholine, dimyristoyl phosphatidylcholine (DMPC), 1-palmitoyl-2-oleoylphosphatidyl choline (POPC), hydrogenated soy phosphatidylcholine (HSPC), distearoylphosphatidylcholine (DSPC); phosphatidic acid (PA), phosphatidylinositol (PI), phosphatidylserine (PS).

As appreciated, the liposome forming lipids may also include cationic lipids (monocationic or polycationic lipids). Cationic lipids typically consist of a lipophilic moiety, such as a sterol or the same glycerol backbone to which two acyl or two alkyl, or one acyl and one alkyl chain contribute the hydrophobic region of the amphipathic molecule, to form a lipid having an overall net positive charge. In cationic lipids, the headgroup of the lipid carries the positive charge.

Monocationic lipids may include, for example, 1,2-dimyristoyl-3-trimethylammonium propane (DMTAP) 1,2-dioleyloxy-3-(trimethylamino) propane (DOTAP); N-[1-(2,3-ditetradecyloxy)propyl]-N,N-dimethyl-N-hydroxyethylammonium bromide (DMRIE); N-[1-(2,3-dioleyloxy)propyl]-N,N-dimethyl-N-hydroxy ethyl-ammonium bromide (DORIE); N-[1-(2,3-dioleyloxy)propyl]-N,N,N-trimethylammonium chloride (DOTMA); 3β[N—(N',N'-dimethylaminoethane) carbamoly] cholesterol (DC-Chol); and dimethyl-dioctadecylammonium (DDAB).

Polycationic lipids due to their large polycationic head group are not liposome forming lipids but rather they form micelle. However, when mixed with other lipids such as cholesterol and various phospholipids at suitable mole ratio the mixtures will form liposomes. The polycationic lipids include a similar lipophilic moiety as with the mono cationic lipids, to which polycationic head groups are covalently attached such as the polyalkyamines spermine or spermidine. The polycationic lipids include, without being limited thereto, N-[2-[[2,5-bis[3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS). The cationic lipids may form part of a derivatized phospholipids such as the neutral lipid dioleoyl-phosphatidyl ethanolamine (DOPE) derivatized with polylysine to form a cationic lipopolymer.

In one embodiment, the liposomes in the composition of matter comprise at least sphingomyelin. The term "sphingomyelin" or "SPM" as used herein denotes any N-acetyl sphingosine conjugated to a phosphocholine group, the later forming the polar head group of the sphingomyelin (N-acyl sphingosyl phosphocholines). The acyl chain bound to the primary amino group of the sphingosine (to form the ceramide) may be saturated or unsaturated, branched or unbranded. In one embodiment, the acyl chain comprises between 12 to 24 carbon atoms (C12-C24), at times between 14 to 20 carbon atoms. In some preferred embodiments, the SPM is a 06:0 or C18:0 sphingomyelin, namely, saturated C16 or C18 SPM. The SPM is preferably a synthetic or semi-synthetic SPM, i.e. a derivative of a naturally occurring SPM and may include the D-erythro (2S,3R) as well as the L-threo (2S,3S) isomers, although the former is preferable. In addition, in the context of the present disclosure, the sphingomyelin is also the corresponding dihydro species in which, typically, although not exclusively, the trans double bond between C4 to C5 of the sphingosine is hydrogenated to form dihydrosphingosine), namely, any dihydrosphingomyelins (DHSM) corresponding to the SPM defined herein above. In yet a further embodiment, the mole ratio between the liposome forming lipids other than SPM and said SPM is typically in the range of 1:1 to 2:1, irrespective of the SPM used in accordance with the present disclosure.

Interestingly, it has been found that when the liposomes comprise in their bilayer SPM at the amount of up to 75% of the total lipids forming the liposome's bilayer, a decrease in the amount of drug leakage is obtained without compromising the rate of drug release from the liposomes at 37° C. and further without compromising the high loading of the drug into the liposomes. Thus, in one particular embodiment, the composition of matter comprises SPM content in the liposomes membrane in an amount between 25 to 75 mole % of the total phospholipids (liposome forming lipids) in said membrane, or about 50 mole % of the total lipids when including cholesterol in the membrane.

Further, interestingly, it has been found and also shown herein below that the combination of hydrogenated soy phosphatidyl choline (HSPC) having a solid ordered (SO) to liquid disordered (LD) phase transition, characterized by a temperature $T_m$ (a temperature in which the maximal change in heat capacity occurs during the phase transition) of ~53° C., with C16SPM having its $T_m$ at ~41.4° C. led to the formation of a stable composition of matter, i.e. reduced drug leakage during 4° C. storage, as compared to a composition of matter lacking C16SPM (which was less stable, namely, showing higher rate of drug leakage during 4° C. storage (i.e. same storing conditions)).

As mentioned above, the liposomes may also comprise other lipids typically used in the formation of liposomes, e.g. for stabilization, for affecting surface charge, membrane fluidity and/or assist in the loading of the active agents into the liposomes. Examples of such lipids, may include sterols such as cholesterol (CHOL), cholesteryl hemisuccinate, cholesteryl sulfate, or any other derivatives of cholesterol.

The liposomes may further comprise lipopolymers. The term "lipopolymer" is used herein to denote a lipid substance modified by inclusion in its polar headgroup a hydrophilic polymer. The polymer headgroup of a lipopolymer is typically water-soluble. Typically, the hydrophilic polymer has a molecular weight equal or above 750 Da. Lipopolymers such as those that may be employed according to the present disclosure are known to be effective for forming long-circulating liposomes. There are numerous polymers which may be attached to lipids to form such lipopolymers, such as, without being limited thereto, polyethylene glycol (PEG), polysialic acid, polylactic (also termed polylactide), polyglycolic acid (also termed polyglycolide), apolylactic-polyglycolic acid, polyvinyl alcohol, polyvinylpyrrolidone, polymethoxazoline, poly ethyloxazoline, polyhydroxyethyl-oxazoline, polyhydroxypropyloxazoline, polyaspartamide, polyhydroxypropyl methacrylamide, polymethacrylamide, poly dimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers. The lipids derivatized into lipopolymers may be neutral, negatively charged, as well as positively charged. The most commonly used and commercially available lipids derivatized into lipopolymers are those based on phosphatidyl ethanolamine (PE), usually, distearoylphosphatidylethanolamine (DSPE).

One particular family of lipopolymers that may be employed according to the present disclosure are the monomethylated PEG attached to DSPE (with different lengths of PEG chains, in which the PEG polymer is linked to the lipid via a carbamate linkage resulting in a negatively charged lipopolymer, or the neutral methyl polyethylenegly-col distearoylglycerol (mPEG-DSG) and the neutral methyl poly ethyleneglycoloxy carbonyl-3-amino-1,2-propanediol distearoylester (mPEG-DS) [Garbuzenko O. et al., Langmuir. 21:2560-2568 (2005)]. Another lipopolymer is the phosphatidic acid PEG (PA-PEG).

The PEG moiety has a molecular weight of the head group is from about 750 Da to about 20,000 Da, at times, from about 750 Da to about 12,000 Da and typically between about 1,000 Da to about 5,000 Da. One specific PEG-DSPE commonly employed in liposomes is that wherein PEG has a molecular weight of 2000 Da, designated herein $^{2000}$PEG-DSPE or $^{2k}$PEG-DSPE.

The liposomes are embedded in a polymeric matrix. The polymeric matrix comprises at least one water insoluble, water absorbent polymer. Such polymeric matrix are known to form in an aqueous environment a hydrogel. The polymeric matrix is, preferably, biocompatible polymer. As used herein, the term "matrix" denotes any network or network like structure that may be formed from a fully cross-linked or partially cross-linked polymer. Thus, it is to be understood that hereinabove and below, when referring to a polymer, it also encompass more than one polymer forming the matrix.

The cross-linked polymer forms a water insoluble (water immiscible) matrix. The term "water insoluble" is used to denote than upon contact with water or a water containing fluid the cross-linked polymer(s) does not dissolve or disintegrates.

Further, in the context of the present disclosure, the cross-linked polymer forming the matrix is biocompatible, i.e. is inert to body tissue, such that upon administration to a body, it will not be toxic, injurious, physiologically reactive or cause any immunological rejection of the composition of matter.

The cross-linked polymeric matrix is also a water absorbing matrix and in the composition of matter in the context of the present disclosure is absorbed with water. As used herein, the term "water absorbing" or "water absorbed" is used to denote that the polymer, once cross linked, is capable of absorbing water in an amount that is at least 4 times, at times 10-50 times and even more of the polymer's or polymers' own weight thereby forming a gel. In the composition of matter of the present disclosure, the cross-linked polymeric matrix is soaked with water thereby forming a hydrogel.

Water absorbing cross-linked polymers generally fall into three classes, namely, starch graft copolymers, cross-linked carboxymethylcellulose derivatives, and modified hydrophilic polyacrylates. Examples of such absorbent polymers are hydrolyzed starch-acrylonitrile graft copolymer; a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer.

In one preferred embodiment, the matrix is a "hydrogel". The term "hydrogel" as used herein has the meaning acceptable in the art. Generally, the term refers to a class of highly hydratable polymer materials typically composed of hydrophilic polymer chains, which may be naturally occurring, synthetic or semi synthetic and crossed linked (fully or partially).

Synthetic polymers that are known to form hydrogels include, without being limited thereto, poly(ethylene oxide) (PEO), poly(vinyl alcohol) (PVA), poly(acrylic acid) (PAA), poly(propylene fumarate-co-ethylene glycol) (P(PF-co-EG)), and polypeptides. Representative naturally occurring, hydrogel forming polymers include, without being limited thereto, agarose, alginate, chitosan, collagen, fibrin, gelatin, and hyaluronic acid (HA). A subset of these hydrogels include PEO, PVA, P(PF-co-EG), alginate, hyaluronate (HA), chitosan, and collagen.

In one particular embodiment of the invention, the polymeric matrix comprises alginate, such as, and at times preferably, low viscosity (LV) alginate (molecular weight of the polycarbohydrate ~100,000), or very low viscosity (VLV) alginate (molecular weight of the polycarbohydrate ~30,000). As also exemplified herein, the alginate was cross linked by Ca ions to from Ca-alginate cross-linked hydrogel. The cross-linked alginate is a water absorbing polymer, forming in the presence of water a hydrogel.

In one further embodiment, the polymer forming the matrix is biodegradable. The term "biodegradable" refers to the degradation of the polymer by one or more of hydrolysis, enzymatic cleavage, and dissolution. In this connection, when the matrix is a hydrogel comprising synthetic polymer, degradation typically is based on hydrolysis of ester linkages, although not exclusively. As hydrolysis typically occurs at a constant rate in vivo and in vitro, the degradation rate of hydrolytically labile gels (e.g. PEG-PLA copolymer) can be manipulated by the composition of the matrix. Synthetic linkages have also been introduced into PEO to render it susceptible to enzymatic degradation. The rate of enzymatic degradation typically depends both on the number of cleavage sites in the polymer and the amount of available enzymes in the environment. Ionic cross-linked alginate and chitosan normally undergoes de-crosslinking and dissolution but can also undergo controlled hydrolysis after partial oxidization. The rate of dissolution of ionic crosslinked alginate and chitosan depends on the ionic environment in which the matrix is placed. As will be illustrated below by one embodiment it is possible to use cross-linked polymer and control the rate of degradation by addition at a desired time and a desired amount of a de-crosslinker.

Specific examples of control of the cross-linking and de-crosslinking may include cross-linking the cationic chitosan with the di-carboxylic acid oxalate (OA) and de-cross-linking by the divalent cation calcium; and cross-linking the anionic alginate with the divalent cation calcium and de-crosslinking by either di-carboxylic acid such as oxalate (OA) or by chelating agents such as EDTA. Thus, at times, the composition of matter may be subjected to de cross linking.

The polymeric matrix may be present in the composition of matter in the form of individual particles, e.g. beads, each particle embedding liposomes, or in the form of a continuous matrix. The particles may be spherical or asymmetrical particles, as appreciated by those versed in the art of hydrogels.

The cross linked polymeric matrix are required to hold the liposomes. As appreciated, liposomes in general may have various shapes and sizes. The liposomes employed in the context of the present disclosure, may be multilamellar large vesicles (MLV) or multivesiclular vesicles (MVV).

MVV liposomes are known to have the form of numerous concentric or non-concentric, closely packed internal aqueous chambers separated by a network of lipid membranes and enclosed in a large lipid vesicle. In the context of the present disclosure, in order to be retained in the matrix, the liposomes have a diameter that is at least 200 nm. Thus, in one embodiment, the MVV are typically large multivesicular vesicles (LMVV), also known in the art by the term giant multivesicular vesicles (GMV). In accordance with one embodiment, the LMVV typically have a diameter in the range of about 200 nm and 25 μm, at times between about 250 nm and 25 μm.

When the liposomes MVV, it is to be understood that the loading of the active agent includes containment in more than one aqueous compartment formed by the lipid membranes, and typically also in the aqueous environment surrounding the non-concentric.

The liposomes of the composition of matter encapsulate at least one active agent. Encapsulation includes the entrapment/enclosure, in the intraliposomal phase, of at least one active agent. The entrapment is a non-covalent entrapment, namely in the liposomal aqueous phase the active agent is freely dispersed and may, under appropriate conditions, be released from the liposomes in a controlled manner.

The active agent may be a small molecular weight compound as well as a polymer (e.g. peptide, protein, nucleic acid sequence etc.). The term "active agent" is used to denote that the encapsulated agent, once administered has a beneficial effect, e.g. as a therapeutic, as a contrasting agent (e.g. radionuclei dyes or dye-conjugates to carrier, chromophor or fluorophor producing agent etc.), as a nutraceutical compound etc. The active agent may be a water soluble, hydrophilic compound as well as an amphipathic compound.

In one embodiment, the active agent is an amphipathic compound. The term "amphipathic compound" is used to denote a compound possessing both hydrophilic and lipophilic properties. There are various functional amphipathic compounds known in the art. One example includes the anti cancer compound doxorubicin. The loading of doxorubicin (e.g., DOXIL™) into preformed liposomes is driven by transmembrane ammonium sulfate gradient (U.S. Pat. No. 5,192,549, U.S. Pat. No. 5,316,771 and Haran et al., [Haran G, et al. (1993) *Transmembrane ammonium sulfate gradients in liposomes produce efficient and stable entrapment of amphipathic weak bases*. Biochim Biophys Acta. 1151(2): 201-15].

In one other embodiment, the amphipathic active agent is an analgesic drug. The analgesic drug would typically be for local analgesic. A non-limiting group of analgesic drugs are selected from the group consisting of benzocaine, chloroprocaine, cocaine, cyclomethycaine, dimethocaine, propoxycaine, procaine, proparacaine, tetracaine, articaine, bupivacaine, carticaine, cinchocaine, etidocaine, levobupivacaine, lidocaine, mepivacaine, piperocaine, prilocaine, ropivacaine, trimecaine, saxitoxin and tetrodotoxin. A preferred group of analgesic drugs include, without being limited thereof, bupivacaine. lidocaine, ropivacaine, levobupivacaine, procaine, chloroprocaine, benzocaine, etidocaine, mepivacaine, prilocaine, ciprocaine, tetracaine, dibucaine, heptacaine, mesocaine, propanocaine, carbisocaine, and butacaine. A specific analgesic drug according to the present disclosure is bupivacaine (hereinafter referred to, at times, as "BUP" or "bup").

In another embodiment, the active agent is a water soluble molecule such as water soluble steroid prodrugs, non steroidal anti inflammatory drug (NSAID), a peptide, protein or nucleic acid sequences, including, for example, cytokines, antibodies, immunostimulating oligonucleotides (ISS-ODN), siRNA etc.

The composition of matter disclosed herein is characterized by a high agent to phospholipid (agent/PL) mole ratio, namely, high loading of the agent per liposome. Although not exclusively, the high loading would typically depend on the type of liposomes used, their size, the loading approach etc. In one embodiment, a high loading is achieved by active (remote) loading approaches (see below) of the active agent into LMVV. In the context of the present disclosure, high loading is used to denote a loading with a active agent to lipid ratio in the resulting composition of matter of at least about 0.5 mole drug per mole liposome phospholipid (mole/mole) (this being characteristic of the LMVV according to the present disclosure).

Loading of the active agent into the liposomes may be by any technique known in the art. Such techniques typically include passive loading or active loading of agents into the liposomes.

Passive loading techniques of encapsulating agents into liposomes typically involve loading of the agent during preparation of the liposomes, e.g. by hydrating dry lipid mixture used to prepare liposomes with a solution of the active agent. By passive loading the agent may be associated to the liposomal membrane or encapsulated within the liposomes' aqueous core. One method for passive loading was described by Bangham, et al., [Bangham A D, Standish M M, Watkins J C (1965) *Diffusion of univalent ions across the lamellae of swollen phospholipids*. J Mol Biol. 13(1): 238-52], where an aqueous phase containing the agent of interest is put into contact with a film of dried liposomes-forming lipids deposited on the walls of a reaction vessel. Upon agitation by mechanical means, swelling of the lipids occurs and multilamellar vesicles (MLV) encapsulating the agent dissolved in the hydration medium are thus formed. A further method for passive loading is the Reverse Phase Evaporation (REV) method described by Szoka and Papahadjopoulos, [Szoka F. C. Jr, Papahadjopoulos D. (1978) *Procedure for preparation of liposomes with large internal aqueous space and high capture by reverse phase evaporation*. Proc Natl. Acad. Sci. USA. 75(9):4194-8.], according to which a solution of lipids in a water insoluble organic solvent is emulsified in an aqueous carrier phase and the organic solvent is subsequently removed under reduced pressure. Other methods of passive loading include subjecting liposomes to successive dehydration and rehydration treatment, or freezing and thawing. Dehydration is carried out by evaporation or freeze-drying [Kirby C and Gregoriadis G (1984) *Dehydration-Rehydration Vesicles: A Simple Method for High Yield Drug Entrapment in Liposomes*. Nat. Biotechnol. 2, 979-984], or mixing liposomes prepared by ultra-sonic irradiation in aqueous solution with the solute to be encapsulated, and the mixture is dried under nitrogen in a rotating flask. Upon rehydration, large liposomes are produced in which a significant fraction of the solute has been encapsulated [Shew R L, Deamer D W. (1985) A novel method for encapsulation of macromolecules in liposomes. Biochim Biophys Acta. 816(1):1-8]. Loading may be improved co-lyophilizing the active agent with the dried liposome forming lipids [International Patent Application Publication No. WO03000227]

Active (remote) loading techniques are also used. For example, drug loading into pre-formed liposomes may achieved using a transmembrane ion gradient or pH gradient. Loading using a pH and ion gradients may be carried out according to methods described in U.S. Pat. Nos. 5,616,341, 5,736,155 and 5,785,987, U.S. Pat. No. 5,192,549, U.S. Pat. No. 5,316,771 and Haran et al., [Haran G, et al. (1993) *Transmembrane ammonium sulfate gradients in liposomes produce efficient and stable entrapment of amphipathic weak bases*. Biochim Biophys Acta. 1151(2):201-15], incorporated herein by reference. The pH gradient may be achieved using calcium citrate-based buffers having extra-liposome high pH and intra-liposome low pH. Intra-liposome high/extra-liposome low ammonium sulphate-based gradient combines the ammonium ion gradient with the pH gradient [Haran et al., 1993, ibid.].

In one embodiment, the composition of matter is held in an aqueous medium. The aqueous medium is any water based buffer solution having a desired osmolality and ion composition and concentration and it is to be understood as encompassing a variety of physiologically acceptable buffers. The buffer system is generally a mixture of a weak acid and a soluble salt thereof, e. g., sodium citrate/citric acid; or the monocation or dication salt of a dibasic acid, e. g., potassium hydrogen tartrate; sodium hydrogen tartrate, phosphoric acid/potassium dihydrogen phosphate, and phosphoric acid/disodium hydrogen phosphate. A weak acid buffer is a buffer solution with constant pH values of between 4 and 7 and a weak base buffer is a buffer solution with constant pH values between 7 and 10. Some non-limiting examples of buffers that may be used for producing the aqueous medium in accordance with the present disclosure include physiological saline (0.9% NaCl), phosphate buffered saline (PBS), citrate phosphate buffer, sucrose histidine buffer, histidine buffer etc., set at a pH of between about 4 to 8, or between 5.5 to 7 (as typically used in liposomal drug delivery systems).

In one embodiment, the aqueous medium is in iso-osmotic equilibrium with the intraliposomal aqueous compartment of the liposomes within the polymeric matrix. When referring to iso-osmotic equilibrium, it is to be understood as meaning that the aqueous medium and the medium of the intraliposomal aqueous compartment have similar osmolalities, the similarity being defined by a difference in osmolality of not more than 50 mOsmole. In accordance with one embodiment, the osmolality of the aqueous medium and of the liposomal aqueous phase are in the range of about 50 to about RCE and Amendment in Response to Jul. 29, 2013 Final Office Action 600 mOsm/kg, or even between about 250 to about 550 mOsm/kg. The iso-osmotic equilibrium may be obtained by holding the composition of matter comprising the polymeric matrix carrying the liposomes, with the buffer solution having an osmolality similar to that of the intraliposomal aqueous compartment.

In one further embodiment, the equilibrium is achieved by using an aqueous medium comprising an amount of free active agent. The amount of free active agent is determined so as to form said iso-osmotic equilibrium. As shown in the examples herein, the presence of the free agent (e.g. BUP in amounts of 0.2%, 0.5% or 2.0%) in the aqueous medium, reduced the leakage of the agent from the liposomes (this being comparable the same formulation without free drug in the aqueous medium).

Interestingly, it has been found that the presence of free active agent in the aqueous medium not only reduced leakage from the liposomes, but also increased the agent to phospholipid ratio in the liposomes (see results below).

As indicated above, the composition of matter may be in the form of particles, e.g. aggregates, beads, such as chitosan or alginate based beads, or any other type of discrete polymeric assemblies or may comprise a continuous polymeric matrix. When the matrix comprises polymeric particles, the latter may be dispersed or suspended in the aqueous medium.

The composition of matter is retained in the aqueous medium during storage. It has been envisages that even if during storage active agent leaks from the liposomes embedded in the matrix into the aqueous medium, upon need, e.g. before use, the storing aqueous medium may be decanted from the container holding the medium, thereby removing dissolved (non-encapsulated) agent from the composition of matter. Decanting the aqueous medium does not affect the liposomes entrapped within the matrix (entrapment being a result of the size of the liposomes). In other words, the encapsulated active agent are retained in place with the liposomes entrapped by the polymeric matrix (e.g. hydrogel). Thus, by simple decanting or replacing the aqueous medium used during storage, it is possible to reduce risks of administering to a subject drug leaked from liposomes during storage.

In the context of the present disclosure, the stability of the liposomes means that the liposomes are chemically and physically unaltered when stored at 4° C. and for a period of at least 3 months. The stability is determined, for example, by measuring the amount of active agent free in the aqueous medium carrying the liposomes, i.e. non-encapsulated active agent, the amount indicative of stability being less than 30%, 20% and at times even less than 10% from the total amount of active agent in the composition of matter (the total amount including encapsulated and non-encapsulated agent).

While at minimum stable storage is for a period of 3 months, as will be shown in the following non-limiting examples, stable storage was also obtained for a period of four months (120 days), 4.5 months and even up to 6 months storing at 4° C. However, as indicated above, the stability would be retained at any other temperature that is lower than the physiological temperature of the body, namely, below 37° C. When referring to lower temperatures it is to be understood that the reasonable storage temperature should be at least 15° C. below body core temperature, i.e. below 22° C. According to one embodiment, storing is at a temperature between about 2° C. to 8° C.

The present invention also provides a method of preparing a composition of matter comprising liposomes encapsulating in their intraliposomal aqueous compartment at least one active agent, the liposomes having a diameter of at least 200 nm and being embedded in a cross-linked water insoluble and water absorbed polymeric matrix, the method comprising mixing (i) liposomes encapsulating in their intraliposomal aqueous compartment at least one active agent, the liposomes having a diameter of at least 200 nm; (ii) at least one cross-linkable polymer; and (iii) an aqueous solution comprising a cross-linker capable of forming with said cross-linkable polymer a water insoluble, water absorbed cross-linked polymer having embedded therein said liposomes.

The cross linker in the context of the present disclosure is any agent capable of cross linking polymers which as a result form a polymeric matrix that is water insoluble. The cross linker may form any type of bond, including covalent bond, ionic bonds etc. with the polymer. Examples of cross linkers are provided hereinbelow. The selection of a cross linker will depend on the type of polymer used for forming the matrix, and the functional groups on the polymer. The cross-linker is at least a bi-functional compound, at times a multifunctional compound, i.e. having two or more moieties capable of linking with two or more polymers.

In accordance with this aspect, the method also comprises adding to said composition of matter an aqueous medium having an osmolality corresponding to that of the intraliposomal aqueous compartment of said liposomes (namely, the osmolality of the aqueous medium is adapted to be essentially the same as that in the liposomes). When referred to a corresponding osmolality it is meant that the aqueous medium has an osmolality that has no more than 50 mOsmole with the osmolality of the intraliposomal aqueous core of the liposomes within the matrix. The osmolality in the intraliposomal aqueous core may be pre-established by the conditions at which the liposomes encapsulating the agent are formed, or it may be determined by techniques known in the art, all being in line with the biochemists general knowledge in liposome technology. The amount of aqueous medium typically added to the competition of matter is such that the composition of matter is entirely contained in the medium.

Also provided by the present disclosure is a method for removal of non-encapsulated active agent from a composition of matter comprising liposomes encapsulating in their intraliposomal aqueous compartment at least one such active agent, the liposomes having a diameter of at least 200 nm and being embedded in a cross-linked water insoluble and water absorbed polymeric matrix, the composition of matter being held in an aqueous medium, the method comprising decanting at least part of said aqueous medium from said composition of matter, thereby removing from said composition of matter at least part of non-encapsulated active agent.

The aqueous medium may be partially withdrawn or substantially fully removed, to provide a composition of matter essentially free of non-encapsulated active agent. Essentially free of active agent denotes that the resulting composition of matter comprises at most 10%, at times, 7% of any non-encapsulated active agent (free active agent). It is noted that even if all aqueous medium is removed from the system, due to the characteristics of the cross-linked polymeric matrix, namely, being absorbed with a high content of water, the compression of matter remains in a hydrogel form.

As may be appreciated by those reading the current disclosure, the above removal method is of particular advantage for compositions of matter after long term storage. As discussed above, during long term storage (several months and more) liposome encapsulated agents tend to leak from the liposomes into the surrounding medium. Thus, once the liposomes are entrapped in a polymeric matrix held within a medium where the non-encapsulated agent (e.g. drug) is dissolved, the removal of the aqueous medium with the dissolved agent allows to reduce the risk involved in administering free active agent.

The present disclosure also provides a pharmaceutical composition comprising as an active ingredient the composition of matter as herein defined, or as obtained by the method disclosed herein. For instance, the present disclosure provides a pharmaceutical composition prepared by the removal method disclosed herein.

The present invention also provides the use of the composition of matter as defined hereinabove for the preparation of a pharmaceutical or diagnostic composition, for, respectively, treatment of a medical condition or for diagnostic purposes. The composition typically comprises, in addition to said composition of matter, at least one physiologically acceptable additive.

Further, the present invention provides a method for the treatment or diagnostic of a medical condition, the method comprising administering to a subject in need of said treatment or diagnostic an amount of the composition of matter as defined hereinabove or in combination with at least one physiologically acceptable additive comprising the same.

Without being bound by theory, it is believed that the administration of the liposomes embedded in the polymeric matrix would reduce uptake of the liposomes by macrophages, thereby increase the retention time of the composition of matter at the site of administration.

The composition of matter, alone (i.e. as is after removal of aqueous medium) or in combination with physiologically acceptable additives may be administered by any route acceptable in the art. According to one embodiment, the administration of the composition of matter is by parenteral injection or infusion. This would include, without being limited thereto, intravenous, intraarterial, intramuscular, intracerebral, intracerebroventricular, intracardiac, subcutaneous, intraosseous (into the bone marrow), intradermal, intrathecal, intraperitoneal, intravesical, and intracavernosal and epiduaral (peridural) injection or infusion. Pareneral administration may also include transdermal, e.g. by transdermal patches, transmucosal (e.g. by diffusion or injection into the peritoneum), inhalation and intravitreal (through the eye).

In one embodiment, the administration is by direct deposition of the composition of matter at the target site, e.g. by injection using a syringe, or by dip-coating an implant to be placed at a target site. The polymeric composition of matter may be placed at a site of injury such as bone, teeth, muscle, tendon, heart, etc.

One particular embodiment of the invention comprises administration of a composition of matter as defined herein to the bone or near a tooth to treat with an anti-bacterial, anti-fungal and/or anti-viral agent, in combination with growth factors so as to support both or teeth regeneration. Treatment of osteoarthritis is one particular embodiment of the present disclosure.

When the active agent is an analgesic drug, a preferred mode of administration is local administration at a desired site by any acceptable route, as can be determined by a medical doctor or any other appropriate physician. With respect to analgesia, the desired site may be, without being limited thereto, bone tendon, joints, GI tract, breast, prostate, reproductive tract, cardiovascular system or any internal organ such as the liver, kidneys, spleen, pancreas etc.

Further, when the active agent is an analgesic drug, the composition of matter may be used for local pain management and/or for treatment of local inflammatory reactions, optionally in combination with other therapies. A non-limiting application may include treatment of arthritis e.g. osteoarthritis or rheumatoid arthritis.

Further, in the context of the present disclosure, the desired site may also serve as a depot and as a reservoir for prolonged systemic release, such as for contraceptive, antibiotics, antiviral anti fungal anti parasite agents, immunosuppressants, hormones and growth factors, neurotransmitors, etc. and in such a case the administration route may be subcutaneous.

The amount of composition of matter administered, and thereby the amount of active agent encapsulated therein should be effective to achieve the desired effect by the active agent, at the target site. For example, if the active agent is a drug, the amount of the composition of matters should be determined so that at the target site the amount of the drug encapsulated therein is sufficient to achieve the desired therapeutic effect. Such desired therapeutic effect may include, without being limited thereto, amelioration of symptoms associated with a medical condition, prevention of the manifestation of symptoms associated with a medical condition, slow down of a progression state of a medical condition, enhance of onset of a remission period, prevent or slow down irreversible damage caused by the medical condition, lessen the severity of the medical condition, cure the medical condition or prevent it from developing, etc. The medical condition to be treated by the composition of matter may be any such condition treatable by the active agent encapsulated in the liposomes according to the present disclosure.

Further, if the active agent may be a diagnostic agent. To this end, the amount of the composition of matter should be such that it would be possible to image the marker at the target site.

The amount of the composition of matters will be determined by such considerations as may be known in the art, typically using appropriately designed clinical trials (dose range studies etc.).

Finally, the present disclosure provides a package (kit) comprising at least one container (e.g. syringe, vial) comprising an aqueous medium holding a composition of matter or a pharmaceutical composition as defined herein, and instructions for decanting said aqueous medium prior to use of said composition of matter. The instruction may include simple mechanical pouring of the aqueous medium, or when the composition of matter and aqueous medium are held in a syringe, the removal of the aqueous medium may include simple pressing out the aqueous medium from the syringe (having a lumen too thin to pull out therefrom the hydrogel).

As used herein, the forms "a", "an" and "the" include singular as well as plural references unless the context clearly dictates otherwise. For example, the term "a liposome forming lipid" includes one but also more lipids capable of forming by themselves a liposome when dispersed in aqueous medium.

Further, as used herein, the term "comprising" is intended to mean that the composition of matter include the recited constituents, i.e. the liposome forming lipid, and the active agent, but not excluding other elements, such as physiologically acceptable carriers and excipients as well as other active agents. The term "consisting essentially of" is used to define composition of matters which include the recited elements but exclude other elements that may have an essential significance on the effect to be achieved by the composition of matter. "Consisting of" shall thus mean excluding more than trace amounts of other elements. Embodiments defined by each of these transition terms are within the scope of this invention.

Further, all numerical values, e.g. when referring the amounts or ranges of the elements constituting the composition of matter comprising the elements recited, are approximations which are varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

DESCRIPTION OF SOME NON-LIMITING EXAMPLES

Materials
Drugs:
Bupivacaine hydrochloride (BUP) was supplied by Sigma St. Louis, Mo.
Methylprednisolone sodium succinate (MPS) was supplied by PHARMACIA NV/SA Puurs-Belgium.
Lipids:
Cholesterol (CHOL) was supplied by Sigma, St. Louis, Mo. (better than 99% pure, standard for chromatography grade).
Fully hydrogenated soy phosphatidylcholine (hereinafter "HSPC-100" or "H100"), Phospholipon® 100H batch no 50190 obtained from Phospholipids GmbH Nattermannallee l*D 50829 Koln, Germany.
Fully hydrogenated soy phosphatidylcholine (hereinafter "HSPC") was obtained from Lipoid Gmbh, Ludwigshafen, Germany.
Fully synthetic N-Palmitoyl-D-erythro-sphingosine-1-phosphocholine N-palmitoyl sphingomyelin, (hereinafter "C16SPM") >98% pure (lot no 546701) was obtained from Biolab Ltd., POB 34038 Jerusalem 91340.
Buffers and Salts:
Ammonium sulfate (AS) was obtained from MERCK.
Calcium acetate monohydrate (CA) was obtained from Aldrich.
Calcium chloride-dihydrate obtained from MERCK.
EDTA obtained from Sigma.
Water Insoluble, Aqueous Absorbent Polymers:
Alginic acid sodium salt (Alginate=ALG), from brown algae, viscosity of 2% solution at 25 c:250 cps LV-ALG (low viscosity) from SIGMA.
Sodium alginate pronova up VLVG-ALG (very low viscosity grade) batch #BP-0709-03 from NOVAMATRIX Sandvika, Norway, Was obtained from Sigma.
Preparation of Drug Loaded LMVV:
Preparation of Large Multi Vesicular Vesicles (LMVV)
Powder mixtures of lipids at the desired mole ratio, as specified in the various experiments hereinbelow, were dissolved in ethanol at 60-65° C. and added to an aqueous solution of ammonium sulfate (AS), calcium acetate (CA) or another buffer (as indicated below) to reach a final phospholipid (PL) concentration of 60 mM and final ethanol concentration of 10%.

The resulting solutions were mixed for 30 min at 65° C. to obtain multilamellar large vesicles (MLV). Alternative methods to prepare MLV can also be used (see for example: Barenholz & Crommelin, 1994, In: *Encyclopedia of Pharmaceutical Technology*. (Swarbrick, J. and Boylan, J. C., Eds.), Vol. 9, Marcel Dekker, N.Y. pp. 1-39).

LMVV were prepared from the MLV with the desired aqueous phase (for example: ammonium sulfate 250 mM or 127 mM, calcium acetate 250 mM, or 200 mM, or a desired buffer) from the MLV by exposing the MLV to 10 cycles of freezing in liquid nitrogen and thawing in a water bath at 60° C. thereby forming the LMVV. At each cycle, for each 1 ml of dispersed LMVV solution the frozen dispersion was kept at the liquid nitrogen for 1 minute. For example, a dispersion of 3 ml was kept in liquid nitrogen for 3 minutes.

Gradient Creation

Transmembrane AS or CA gradient were created by removal of AS or CA (respectively) from the extra liposome aqueous phase and replacing it with NaCl.

Three methods were used for creating the pH gradient:

(i) Centrifugation (Grant et al 2004, ibid.] for both AS and CA gradients at 1000 g, for 5 min at 4° C. Supernatant was removed and pellet was washed with saline at 4° C. The washing process was repeated 7 times.

(ii) Dialysis using MWCO 12-14000 Dalton dialysis tubing.

(iii) Diafiltrating using Midjet benchtop system with hollow fiber cartridge 500000 NMWC (GE Healthcare Bio-Sciences Corp. Westborough, Mass. 01581 USA).

Loading of Bupivacaine

LMVV were loaded with Bupivacaine (BUP) using two alternative approaches:

(i) Remote loading of preformed liposomes having a trans-membrane ammonium sulfate (AS) gradient (Haran et al., (1993), BBA, 1151 201-215), modified to fit the LMVV (Grant et al 2004, ibid.); Like in the remote loading od doxorubicin, this approach take advantage of the fact that BUP is an amphiphatic weak base; or remote loading into preformed LMVV having a trans-membrane calcium acetate (CA) gradient (Clerc & Barenholz. (1995), BBA, 1240, 65-257, Avnir et al (2008) *Arthritis & Rheumatism*, 58, 119-129). This method makes use of the fact that BUP, due to its tertiary amine is also an amphipathic weak acid (ii) Passive loading was performed by lipid hydration using aqueous solutions of BUP to form the BUP loaded MLV from which BUP loaded LMVV were prepared as described above (LMVV preparation).

In both approaches loading was performed at 60-65° C., which is above the HSPC and C16SPM solid-ordered (SO) to liquid-disordered (LD) phase transition temperature range (characterized by the relevant $T_m$). It is noted that HSPC and C16SPM are the liposome-forming lipids of the LMVV described here.

Remote loading was performed for 30 min. at 60-65° C. using 4.5%, 5.5%, or 5.7% BUP, which is equivalent to osmolarity of (saline=0.9% weight per volume), or 6% BUP in distilled water as the liposome external aqueous phase. An amount 0.5 ml of a wet LMVV pellet and 2 ml of BUP solution were used for the remote loading. The mixture was then cooled to 4° C. in which it was stored overnight followed by unloaded free drug removal (as described below).

Passive loading of BUP was performed by hydrating the ethanol lipid solution with aqueous solution of distilled water containing 4.5% (231 mOsm/kg), or 5.5% (285 mOsm/kg), or 6% (301 mOsm/kg) or 7% (346 mOsm/kg), or 8% (373 mOsm/kg) or 10% (454 mOsm/kg) BUP (W/V) at 65° C. for 30 min. For this process 0.5 ml ethanolic lipids solution containing 225 mg phospholipids and 77 mg CHOL were used. This solution was mixed with 5 ml of one of the above indicated BUP aqueous solutions. The suspension was processed by 10 repetitive freezing and thawing cycles (as described above) and than kept overnight in a cold room (4°-6° C.) followed by free drug removal (as described below).

Free Drug Removal

Non-encapsulated BUP was removed from LMVV by washing with saline (1 ml liposomes/4 ml saline) and centrifuging the dispersion at 1000 g for 5 min at 4-5° C. The washing process was repeated 7 times. The final medium (referred to herein as the "aqueous medium") used to replace extra-liposome from CA gradient loaded liposomes was PBS. The use of PBS was preferred over saline. AS and the medium used for passive loading of liposomes was replaced and LMVV were washed with un-buffered saline.

The LMVV was concentrated to a final solution of 2% BUP for the passive loading and AS gradient loading. For CA gradient loading LMVV with 1% BUP final concentration was used, due to the large volume of these LMVV. These concentrations were close to the highest concentrations used for mice injection with BUP in LMVV The stability of LMVV thus formed was measured with respect to the release rate of BUP from liposomes during storage at 4° C.

Bupivacaine Loading Under Iso-Osmotic Conditions

When referring to iso-osmotic conditions, it should be understood to mean that the osmolality of the intraliposomal aqueous core and the external medium inside and outside the liposomes are essentially identical or close, all as defined hereinabove.

Three osmomolar concentrations were tested:

(i) 280 mOsm/kg isoosmotic to physiological saline (0.9% NaCl) condition: the AS and CA gradient LMVV were prepared with ~20 mg/ml AS or CA solution adjusted by AS or CA solutions to 280 mOsm/kg. BUP loading concentration was 5.7% BUP in water or 4.5% BUP in NaCl solution to reach 280 mOsm/kg.

(ii) 550 mOsm/kg, isoosmotic to 250 mM AS: the washing solution for creating the AS gradient and the solution for removal of the free drug after loading was NaCl solution. adjusted to 550 mOsm/kg. The drug loading conc. was 4.5% BUP in NaCl solution, or 4.5% BUP in sucrose sol. to make 550 mOsm/kg.

(iii) 650 mOs, isoosmotic to 250 mM CA.

Methyl Prednisolone Hemisuccinate Sodium Salt (MPS) Loading

MPS is a water soluble amphiphatic weak acid glucocorticosteroid prodrug used in the treatment of inflammation and autoimmune diseases.

MPS was loaded into LMVV using remote loading into pre-formed LMVV having a trans membrane calcium acetate (CA) gradient [see loading in Clerc and Barenholz. (1995), BBA, 1240, 65-257, Avnir et al (2008) ARTHRITIS & RHEUMATISM, 58, 119-129)].

The loading was conducted under iso-osmotic conditions (0.5 ml LMVV incubated with 2 ml 25 mg/ml MPS plus sucrose to reach 280 mOsm). The osmotic concentration inside and outside the liposomes were identical to 280 mOsm/kg (similar to physiological saline).

LMVV Co-Loaded with BUP and MPS by Trans-Membrane CA Gradient

The procedure described above for BUP loading by CA gradient was used using a mixture of BUP and MPS under conditions that their mixture do not exceed iso-tonicity. Alternative active ingredients, such as other amphiphatic weak acid steroid prodrugs, e.g. beta methaosone hemisuccinate may also be used.

Preparation of $Ca^{++}$ Cross-Linked Alginate Gel Beads Containing Bup Loaded LMVV The homogeneous blend solution (400 μl) contained fresh and cold (4° C.) 2% (w/v) sodium alginate and BUP loaded LMVV (LMVV-BUP) 1:1 (V/V) was dripped through a 25G*⅝" (0.5 mm*16 mm) injection needle into 5 ml solution of cold calcium chloride having an Osmolarity of 280 mOs when LMVV prepared in 280 mOs were used or 550 mOs when LMVV prepared at 550 mOs were used, as specified in each experiment After 15 minutes of mechanical stirring at 4° C. smooth and spherical beads were formed. These beads were than washed with cold iso-osmotic NaCl solution (280 mOs when LMVV prepared in 280 mOs were used or 550 mOs, when LMVV prepared at 550 mOs were used).

Each 5 beads (as manually counted) were incubated for a short time (<30 minutes) with 50 µl iso-osmotic NaCl solution at 4° C.

When necessary to get de-crosslinking of the beads by Ca ions removal. small aliquot of 100 mM EDTA to be in excess to the Ca ions was added. [Meera George, T. Emilia Abraham, Journal of Controlled Release 114 (2006) 1-14].

Preparation of Oxalate Cross-Linked Chitosan Gel Beads Containing BUP Loaded LMVV LMVV loading was performed using transmembrane ammonium sulfate gradient. LMVV of two lipid compositions were used: (i) HSPC100/CHOL (60:40 mole ratio) and (ii) HSPC100/C16SPM/CHOL (30:30:40 mole ratio).

Equal volumes of 2% (weight per water volume) chitosan solution and BUP loaded LMVV (which were not washed from the intersticial BUP) were mixed at 4° C. The mixtures were dripped into 120 mM (280 mosmomolar) oxalate followed by washing in cold saline. The beads formed were stored at 0.2; 0.5; 1.0; or 2.0% bupivacaine solutions brought to 280 mOs with NaCl and stored in such storage media at 4° C. till their use. Then the supernatant of beads was disposed.

Alternative Procedure for Storage of Cross Linked Hydrogel Containing Drug Loaded LMVV:

The following alternative procedure was aimed to eliminate almost completely the issue of drug release during storage at 4° C.

To this end, LMVV were prepared and loaded with drug such as bupivacaine (without free drug removal) as described above. The LMVV were concentrated by one step centrifugation, the supernatant was removed and packed LMVV were encapsulated in cross linked Ca alginate or chitosan oxalate hydrogel as described above.

The excess solution of $CaCl_2$ was replaced with the supernatant (storage media contained bupivacaine such as 0.2; 0.5; 1.0; or 2.0% bupivacaine brought to 280 mOs with NaCl) and stored in such storage media at 4° C. till its use.

Prior to injection for pain reduction or other indications (i.e. inflammation) the excess storage medium was either removed or not removed as described in the specific experiment and the cross linked hydrogel was either used as is or after being washed by 280 mOs NaCl as described in the specific experiment.

Assays

Phospholipids (PL) determination: PL concentration was determined by the modified Bartlett method (Shmeeda et al., (2003), Method Enzymol. 367, 272-292).

Bupivacaine determination: free (non liposomal) or total (liposomal plus free) concentration of bupivacaine was measured by HPLC (Grant et al Parm. Res., 2001 18, N3, 336-343; Anesthesiology, 2004, 101, 133-137).

Drug/lipid ratio determination for hydrogel beads: The washed beads were injected through a 25G×⅝" (0.5 mm×16 mm) syringe needle to have homogenous dispersion and were diluted ×10 with saline:

- 50 μl and 100 μl used for PL. determination.
- 100 μl centrifuged 10' 2000 g at 4° C. and the supernatant diluted ×10 with isopropanol (IPA) to determine free bupivacaine.
- 100 or 200 μl heated in boiling water, than centrifuged 10' at 2000 g. The supernatant was diluted ×10 with IPA to determine total bupivacaine by HPLC.

All samples for bupivacaine determination were centrifuged for 2 min. at 5000 g (using Eppendof centrifuge) after dilution in IPA. The upper phase was removed and analyzed by HPLC.

It is noted that the different batches of the same experiment may vary in terms of the volume of storage medium and this difference may affect the absolute % of agent in the medium. However, as shown in the results, the general trend obtained from all batches is the same and thus the conclusion drawn from the various experiments is the same, namely, that the embedment of the liposomes in a hydrogel significantly reduces the agent leakage into the storage medium.

LMVV and MLV size distribution analysis: a particle size analyzer (Beckman Coulter LS 13 320) was used. This instrument combines two methods of size distribution analyses: multi-wave light diffraction and polarization intensity differential scattering (PIDS polarization of the light). This combination allows the determination of broad size distributions in the range of 40 nm to 2 mm and therefore it is more suitable for the size distribution analyses of large liposomes such as LMVV and large MLV.

Osmomolarity measurement: The osmomolarity of the solutions (storage media) was measured by ADVANCED INSTRUMENTS, Inc model 3320 osmometer (Norwood, Mass., USA).

Analgesic efficacy in male Swiss Webster mouse model: Testing for analgesia was done by electrical stimulation of mice skin as described elsewhere (G. J. Grant et al, Pharmaceutical Research, 18, no 3, 336-343, 2001). Pain as electrical stimulation at the desired intensity was inflicted to the skin of shaved mice abdomen. The current generator (model S48, Grass Instruments (W. Warwick, R.I. USA) was used. Mice (male Swiss-Webster, 26±3 gr (n=7 per group) were used. The mice were shaved the hair overlying the abdomen and tested prior to injection to determine the Individual vocalization threshold of each mice. Than the mice were injected with (0.3-0.4 ml of one of the following: free bupivacaine, or LMVV-BUP or various LMVV entrapped in Ca-alginate or chitosan-oxalate cross linked hydrogels through 30G needle. The analgesia duration was than followed as specified in the experiment itself. All experiments were approved and ratified by the HUJI ethic committee.

Analysis of the in vivo mice analgesia: A numerical score to the spreadsheet was introduced for the evaluation of the analgesic effect of various liposome preparations performance in vivo: For each time period (e.g. 4 hrs, 8 hrs etc) a numeric value to each mouse in the experiment was given. If the anesthesia was complete the numeric value given was 1.0; when analgesia was partial (incomplete) it received the numeric value of 10.0 in the Table 1 and in other Tables a score of 0.5 and for no anesthesia the numeric score was 0. The mean for each subgroup was calculated separately (i.e. 1% 300 μl, 2%150 μg).

Results

Example 1 Characterization of LMVV-BUP

Bupivacaine to Lipids Ratio

BUP was remote loaded into LMVV by AS gradient using three different of BUP to lipid v/v ratios:

(i) wet LMVV pellet to 5.7% BUP, using 1:4 vol/vol ratio.
(ii) wet LMVV pellet to 5.7% BUP, using 1:2 vol/vol ratio
(iii) wet LMVV pellet to 5.7% BUP using 1:1 vol/vol ratio.

The characteristics of the resulting LMVV are provided in Table 1:

TABLE 1

BUP loaded LMVV

| PL/CHOL ratio | Loading method | Mean size (μm) |
|---|---|---|
| SPM/CHOL 6/4 | CA gradient | 8.33 ± 4.71 |
| SPM/CHOL 6/4 | AS gradient | 5.7 ± 2.6 |
| HSPC/CHOL 6/4 | passive | 6.0 ± 3.2 | ratio) was obtained with the LMVV composed of HSPC100/C16SPM/CHOL, their lowest release rate of BUP from this particular formulation at 4° C. without compromising it release rate at 37° C. rendered this combination a preferred LMVV formulation.

The release rate from liposomes comprising HSPC100/C16SPM/CHOL 3/3/4 (either SUV or LMVV as indicated) employing the different loading techniques, different active agents (BUP or MPS, the "Drug") and different aqueous media (washing and storing buffer) were examined. The results are presented in Table 2.

TABLE 2

Drug to phospholipid (PL) mole ratio and loading method effect on stability (defined as drug release at 4° C.) of LMVV using liposomes (LMVV or SUV composed of HSPC100/C16SPM/CHOL 3/3/4).

| Liposome type | Loading technique | Aqueous medium | Drug/PL mole ratio | % free drug release at 4 c. | | | | | | | | |
|---|---|---|---|---|---|---|---|---|---|---|---|---|
| | | | | 17 d | 21 d | 35 d | 40 d | 76 d | 90 d | 120 d | 4.5 month | 6 month |
| LMVV-BUP | Passive by 4.5% bup | Saline 2% bup | 1.5 | | | 17.8 | | | | | | |
| LMVV-BUP | Passive by 5.5% bup | Saline 2% bup | 1.7 | | | 20.9 | | | 36.3 | | | |
| LMVV-BUP | Passive by 6% bup | Saline 2% bup | 1.7 | | | 23.5 | | | 36 | | | |
| LMVV-BUP | Passive by 7% bup | Saline 2% bup | 1.9 | | | 25.8 | | | 40.6 | | | |
| LMVV-BUP | 250 mM CA grad | PBS, 1% bup | 0.8 | | | | 11 | | | 19.9 | | 44 |
| LMVV-BUP | 107 mm CA grad | Saline 0.6% bup | 1.2 | | 9 | | | | | 36.2 | | |
| LMVV-BUP | 107 mm CA grad | Saline 0.7% bup | 1.1 | 7.5 | | | | | | 43 | | |
| LMVV-BUP | 250 mm AS grad | Saline 2% bup | 1.6 | | | | 8 | | | 11.1 | | 21 |
| LMVV-BUP | 250 mm AS grad | 1.75% NaCl | 1.4 | 2.5 | | | | | | 9.9 | 22 | |
| LMVV-BUP | 250 MM AS grad | 1.75% NaCl | 2 | | | 8 | | 9 | | | | |
| LMVV-BUP | 127 mm AS grad | Saline 0.9% bup | 2.3 | | 3 | | | | | 9.6 | 13 | |
| LMVV-BUP | 127 mm AS grad | Saline 0.7% bup | 1.5 | 2.8 | | | | | | 13.5 | | |
| LMVV-BUP | 127 mm AS grad | Saline | 1.5 | | | 3.3 | | 20 | | | | |
| LMVV-MPS | 107 mm CA grad | Saline | 0.6 | | 1.4 | | | | | | | |
| SUV-MPS | 250 mm CA grad | Saline | 0.3 | | | | | | | | | |
| LMVV-BUP 20 ml | 127 mm AS grad | Saline | 1.35 | | 5 | | 9 | 11.1 | | | | |
| LMVV-BUP (20 ml | 127 mm AS grad dialysis tube | Saline | 1.56 | | 3.3 | | | | | | | |
| LMVV-BUP 10 ml | 127 mm AS grad diafiltration | Saline | 1.17 | | | | | | | | | |

Figure 1B:
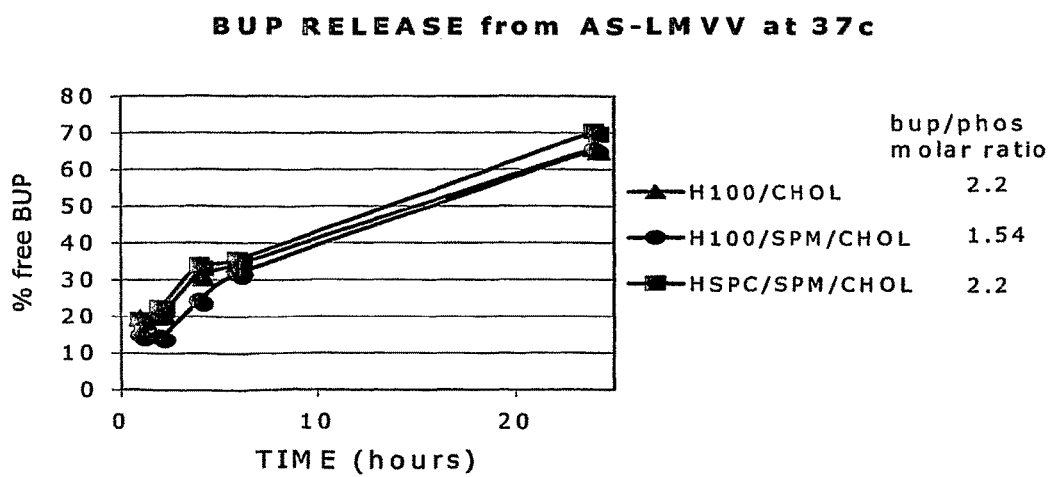

FIGS. 1A-1B describe the release of Bupivacaine (BUP), during storage at 4° C. Specifically, in FIG. 1A LMVV is composed of HSPC/CHOL (as described in U.S. Pat. No. 6,162,462); HSPC/C16SPM/CHOL (3/3/4); HSPC100/CHOL (6/4) an HSPC100/C16SPM/CHOL (3/3/4) all ratios are mole per mole. Also shown, is the release of BUP at 37° C. (FIG. 1B) where LMVV is composed of HSPC100/CHOL (6/4); HSPC100/C16SPM/CHOL (3/3/4), or, HSPC/C16SPM/CHOL (3/3/4), again, all ratios are mole ratio, All LMVV used have been loaded with BUP using an remote loading driven by transmembrane ammonium sulphate (AS) gradient.

The data presented in FIG. 1A show that the release rates of BUP during 60 days storage at 4° C. of the HSPC/CHOL LMVV (an identical formulation described in U.S. Pat. No. 6,162,462) was the highest, followed by the release rate from HSPC100/CHOL liposomes. The lowest release rate was achieved when HSPC100/C16SPM/CHOL LMVV were used. FIG. 1B shows that in 24 hours, the release at 37° C. of LMVV of the 3 compositions is almost identical and reached the level of 65% to 70% of the LMVV BUP—still without reaching a plateau. It was thus concluded that although a slight lower loading of BUP (lower BUP/PL FIGS. 2A and 2B demonstrate the release rate at 4° C. (FIG. 2A) and 37° C. (FIG. 2B) of BUP from LMVV having the same lipid compositions as used in FIGS. 1A and 1B, wherein BUP was remotely loaded using Ca acetate gradient. The SPM used was C16 SPM.

The ratio BUP/PL obtained by the CA gradient remote loading was lower than that obtained for the AS gradient remote loading. Stability assessed from the BUP release at 4° C. was lower than for the LMVV of the same lipid composition remote loaded by AS gradient (release rate was higher) (Compare FIGS. 1A and 2A). At 37° C. the release rates are similar to those of the LMVV loaded with BUP by AS gradient, except that rate of release is faster at the first 10 hours followed by an almost plateau (compare FIGS. 1B and 2B). It is apparent from FIG. 2A that the HSPC100 LMVV has best stability (i.e. lowest leakage at 4° C.) than HSPC based LMVV, and that C16SPM effect on improving stability is much greater than the difference between the two HSPC preparations. C16SPM also reduces leakage rate for both HSPC and HSPC100 compositions by a similar extent.

FIGS. 3A and 3B demonstrate the release rate at 4° C. (FIG. 3A) and 37° C. (FIG. 3B) of BUP loaded LMVV of the same lipid compositions used in FIGS. 1A and 1B, wherein LMVV were passively loaded with BUP. The SPM used is C16SPM, and a comparison of HSPC/SPM/CHOL and HSPC100/SPM/CHOL was also made at 4° C.

In general, release rates at 4° C. for passively loaded LMVV of the 3 liposomal compositions used, were higher than for the remote loading via CA gradient and much higher when compared with BUP AS remote loaded LMVV.

However the effect of LMVV lipid composition on release rates at 4° C. and 37° C. were similar (but larger in magnitude) to that observed for the remote loading driven by AS or CA gradient, thus indicating that the ion gradient driven remote loading increases LMVV loading stability at 4° C.

LMVV Optimization

Various LMVV formulations with different mole ratio of HSPC100 to C16SPM were prepared in order to determined the optimal mole ratio between these two constituents. The different formulations are provided in Tables 3A and 3B.

TABLE 3A

Effect of HSPC100:C16SPM mole ratio in HSPC100/C16SPM/CHOL LMVV formed by active loading with AS gradient

| % BUP loading | SPM/HSPC100 mole ratio | BUP/PL mole ratio | % drug release at 4° C. at the specified times | | | | | |
|---|---|---|---|---|---|---|---|---|
| | | | 8 d | 22 d | 30 d | 38 d | 2 month | 3.5 month |
| 4.5 | 0/1 | 2.2 | 2.5 | | 8.2 | | | 18.9 |
| 4.5 | 1/0 | 1.8 | 4 | | 9.5 | | | 15.5 |
| 4.5 | 1/1 | 1.68 | | | | | 8 | |
| 5.7 | 1/1 | 1.96 | | 7.5 | | 8.7 | | |
| 5.7 | 5/4 | 2.03 | | 5.2 | | 7 | | |
| 5.7 | 2/1 | 1.5 | | 5.8 | | 7.8 | | |
| 5.7 | 7/2 | 1.6 | | 5.3 | | 7.5 | | |
| 5.7 | 0/1 | 1.8 | 4.3 | | | | | |
| 5.7 | 1/1 | 1.55 | 2.6 | | | | | |
| 5.7 | 2/1 | 1.44 | 2.4 | | | | | |

TABLE 3B

Effect of HSPC100 to C16SPM mole ratio in HSPC100/C16SPM/CHOL LMVV formed by active loading with CA gradient.

| % BUP loading | SPM/HSPC100 mole ratio | BUP/PL mole ratio | % drug release at 4° C at the specified times | | | | | |
|---|---|---|---|---|---|---|---|---|
| | | | 8 d | 22 d | 30 d | 38 d | 2 month | 3.5 month |
| 4.5 | 0/1 | 1.7 | 2 | | 19.2 | | | 41.2 |
| 4.5 | 1/0 | 1.45 | 7.4 | | | 8.8 | | 20.8 |
| 4.5 | 1/1 | 1.77 | | | | | 15 | |
| 4.5 | 0/1* | 1.16 | 2 | | 25.8 | | | |
| 4.5 | 1/1* | 1.5 | 3 | | | 12.6 | | 34 |
| 4.5 | 1/3* | 1.5 | 3.7 | | | 16 | | 41 |

*HSPC and not HSPC100

Further, pre-formed LMVV were centrifuged for 5 min at 4° C. at 2000 g to give packed LMVV. For remote loading the packed LMVV were suspended in various volumes of 5.7% BUP. The volume ratio of BUP to LMVV or PL is given in Table 4.

TABLE 4

Optimization of passive loading to the volume ratio of 5.7% BUP to packed LMVV (during loading).

| BUP/LMVV volume ratio* | BUP/PL mole ratio | % free BUP t = 0 |
|---|---|---|
| 4 | 1.17 | 0.4 |
| 2 | 1.23 | 0.6 |
| 1 | 1.13 | 2.8 |

Percent of BUP release from various LMVV formulations with or without C16SPM is also presented in FIGS. 7A to 7E. In these figures, the percent of free BUP storage media at 4° C. or 37° C. is presented (1% is equivalent to 10 mg/ml).

Percent of BUP release from various LMVV formulations with or without C16SPM is also presented in FIGS. 7A to 7E. In these figures, the percent of free BUP storage media at 4° C. or 37° C. is presented (1% is equivalent to 10 mg/ml).

(B) Characterization of Alginate Gel Beads Encapsulated Bupivacaine Loaded LMVV (ALG-LMVV-BUP)

Table 5 below provides characterization of the alginate beads embedding LMVV-BUP-using LMVV composed of HSPC100/C16SPM/CHOL 3/3/4 (mole ratio). It is noted that compositions comprising MPS were prepared in a similar manner using CA transmembrane gradient.

TABLE 5

Characterization of low viscosity alginate beads encapsulating bupivacaine remote loaded LMVV (by ammonium sulfate transmembrane gradient)

| | LMVV-BUP beads | EMPTY beads |
|---|---|---|
| WEIGHT | | |
| (mg/bead) | 4.27 ± 0.6 | 3.3 |
| WATER | | |
| mg/bead | 3.085 ± 0.21 | 2.54 |
| mg/mg bead | 0.903 | 0.762 |
| $Ca^{++}$ | | |
| µg/bead | 3.906 ± 0.06 | 4.35 |
| µg/mg beads | 1.33 | 1.64 |
| Phospholipids | | |
| nmole/bead | 51.34 ± 0.93 | 0 |
| nmole/mg beads | 14.88 | |
| Alginate | | |
| µg/bead | 22.7 ± 0.5 | |
| Bupivacaine | | |
| nmole/bead | 68.06 ± 9.7 | 0 |
| µg/bead | 22.66 ± 3.3 | |

In addition, the kinetics of drug release (BUP or MPS) from the system were determined. For this the storage medium of Ca alginate hydrogel were collected and the level of either BUP (as describes in Grant et al 2004 ibid) or for MPS (as described in Avnir et al 2008 ibid) were determined using HPLC methods. The results are shown in Table 6.

TABLE 6

The kinetics of drugs (BUP or MPS) release from alginate encapsulated LMVV (HSPC100/C16SPM/CHOL 3/3/4) beads.

| Sample | LMVV loading process | % Free drug release at 4° C.*** | | | | | |
|---|---|---|---|---|---|---|---|
| | | 16 d | 22 d | 39 d | 60 d | 74 d | 100 d |
| BUP-LMVV bead* | Passive 4.5% | | 9.4 | | | 18.1 | |
| BUP-LMVV bead* | Passive 5.5% | | 9.3 | | | 18.7 | |

TABLE 6-continued

The kinetics of drugs (BUP or MPS) release from alginate encapsulated LMVV (HSPC100/C16SPM/CHOL 3/3/4) beads.

| Sample | LMVV loading process | \% Free drug release at 4° C.*** | | | | | |
|---|---|---|---|---|---|---|---|
| | | 16 d | 22 d | 39 d | 60 d | 74 d | 100 d |
| BUP-LMVV bead* | Passive 6% | | 17.0 | | | 22.2 | |
| BUP-LMVV bead* | Passive 7% | | 12.4 | | | 21 | |
| BUP-LMVV bead* | 250 mM CA grad | | | 10.0 | | | 15.8 |
| BUP-LMVV bead* | 250 mM AS grad | | | 11.8 | | | 15.6 |
| BUP-LMVV bead* | 127 mM AS grad | 1.6 | | | 7.6 | | |
| BUP-LMVV bead* | 127 mM AS grad | 2.8 | | | 7.3 | | |
| BUP-LMVV bead* | 250 mM AS grad | 7.2 | | | 11.5 | | |
| BUP-LMVV bead* | 250 mM AS grad | 2.7 | | | 13.1 | | |
| BUP-LMVV bead* | 127 mM AS grad | | | | | 18 | |
| MPS-LMVV bead* | 107 mM CA grad | | 3.3 | | | | |
| MPS-SUV bead* | 107 mM CA grad | | 1.1 | | | | |
| BUP-LMVV bead** | 127 mM AS grad | 1.5 | | | 8.5 | | |

*low viscosity alginate (LV ALG)
**very low viscosity alginate (VLG ALG)
***only free drug release from the ALG-LMVV beads (the phospholipid determination in the liquid on the top of the beads was 0, below detection limits).

Figure 4A:
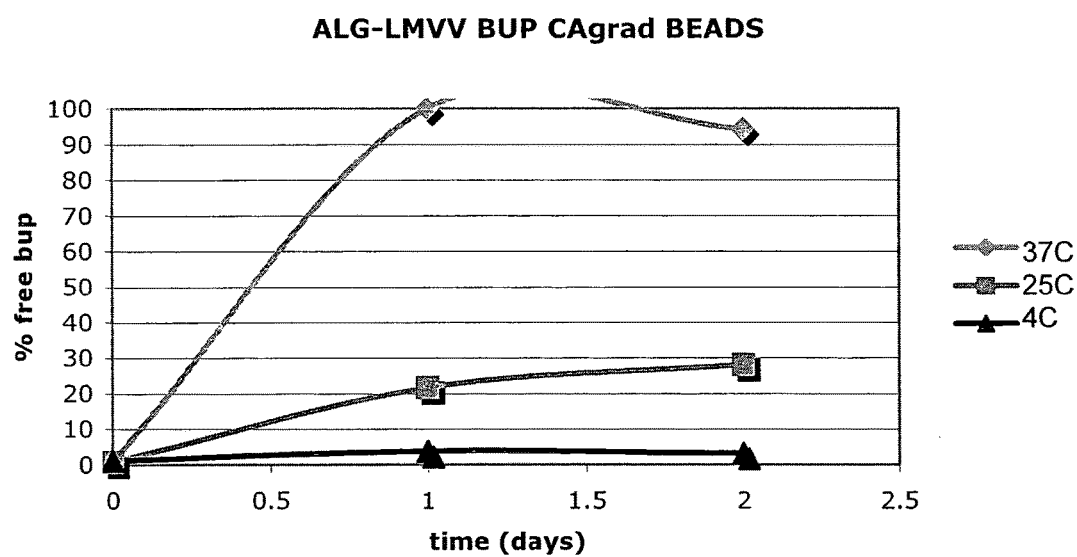
FIGS. 4A-4B are graphs showing the temperature dependent % release of BUP from alginate beads embedding LMVV (HSPC/C16SPM/CHOL 3/3/4 mole ratio)-encapsulated BUP, where the LMVV have been loaded with BUP by remote loading using calcium acetate) gradient (CAgrad, FIG. 4A) or ammonium sulfate gradient (ASgrad, FIG. 4B).
Figure 4B:
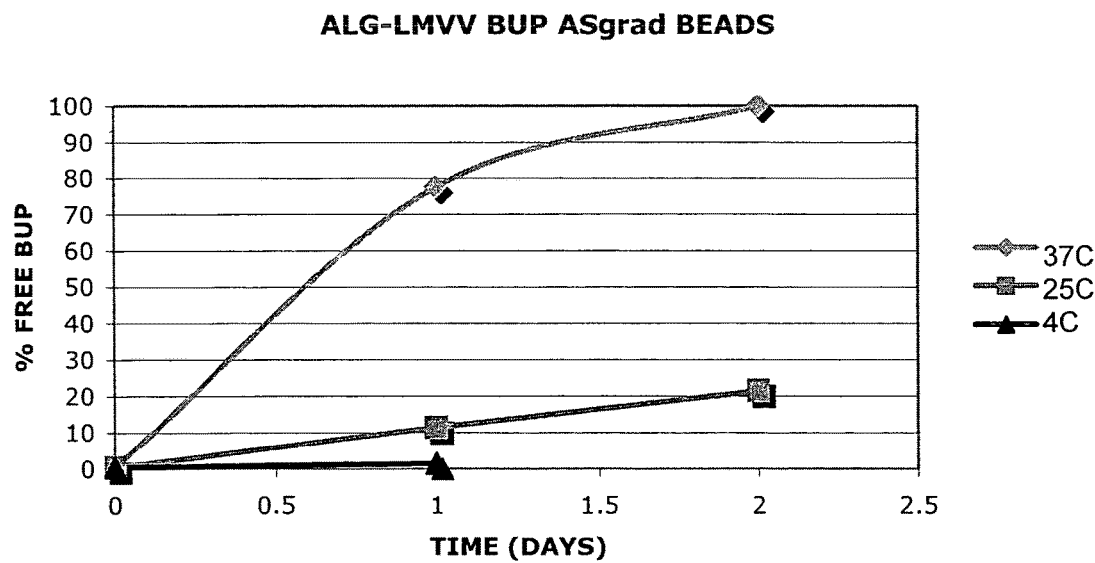
Figure 5A:
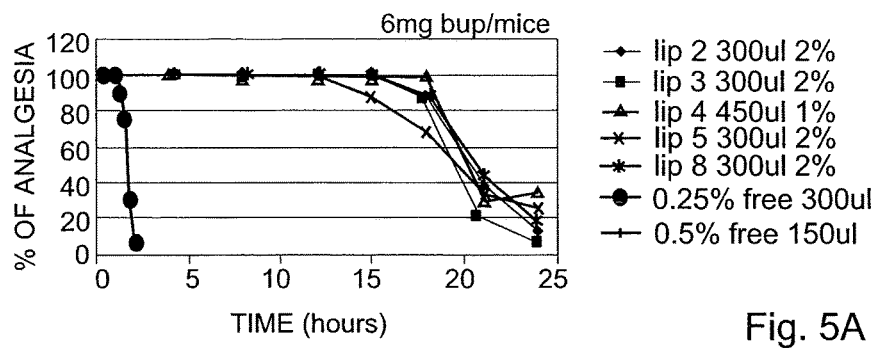
FIGS. 5A-5C are graphs showing the duration of analgesia in mice using various liposomal systems identified in Table 8 as formulations 1 to 8 (identified in the Figures with in the corresponding formulation number "x" as "lip x"), FIG. 5A showing the effect of injected volume of liposomal BUP or in free form, the amount of BUP being constant 6 mg/mouse.
Figure 5B:
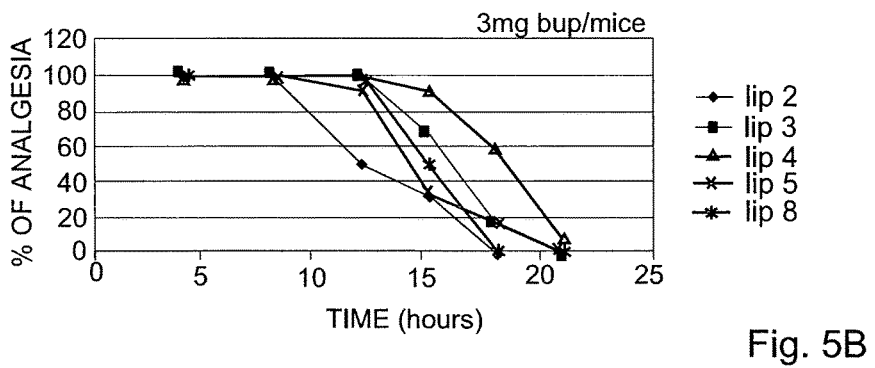
Figure 5C:
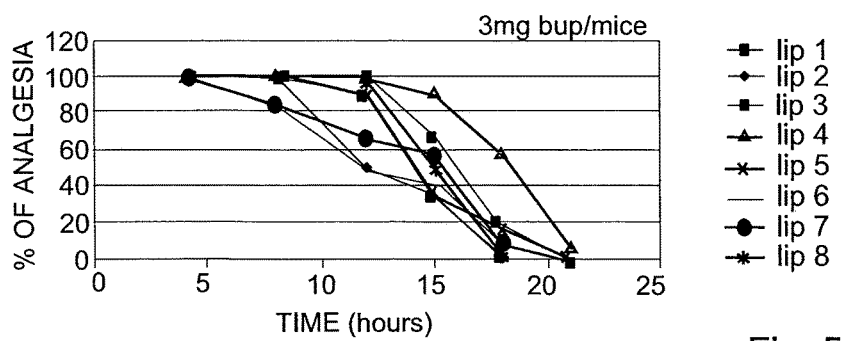
Figure 6A:
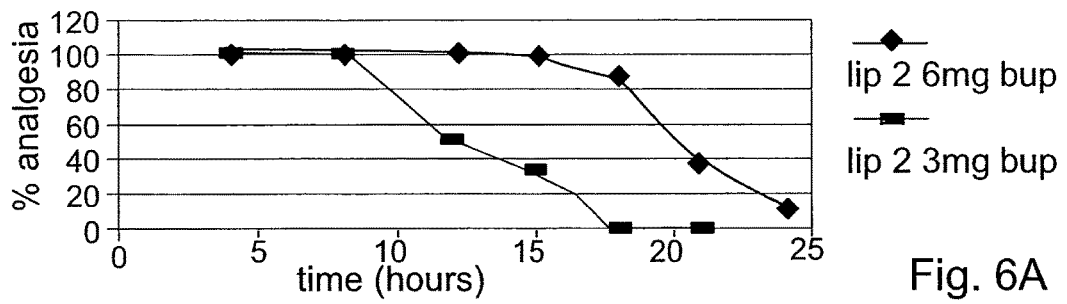
FIGS. 6A-6F are graphs comparing analgesia duration of two different doses of BUP (3 mg/mouse and 6 mg/mouse) for the five different LMVV formulations identified in Table 8 ("lip x" in FIGS. 6A-6E) and 2 different amounts (0.375 and 0.75 mg/mouse) of non-encapsulated (free) BUP (in FIG. 6F)
Figure 6B:
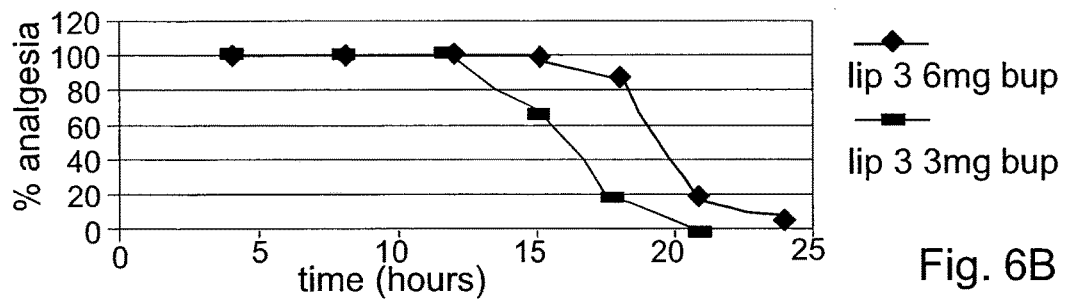
Figure 6C:
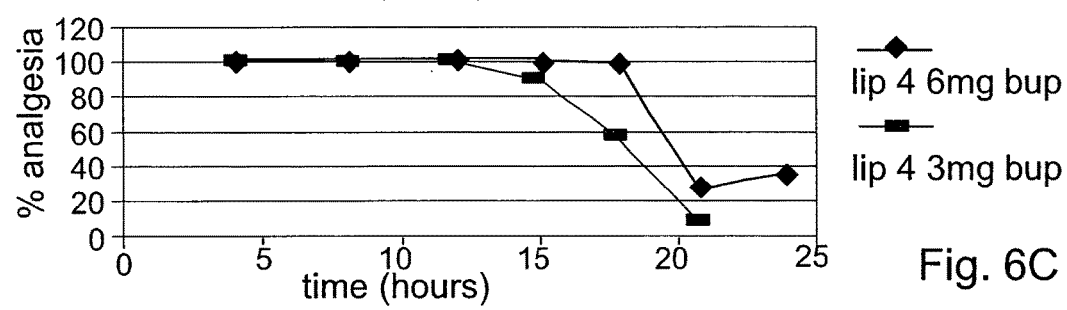
Figure 6D:
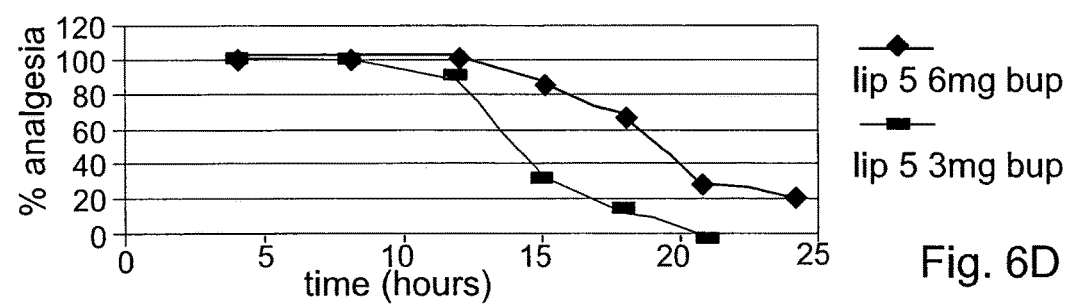
Figure 6E:
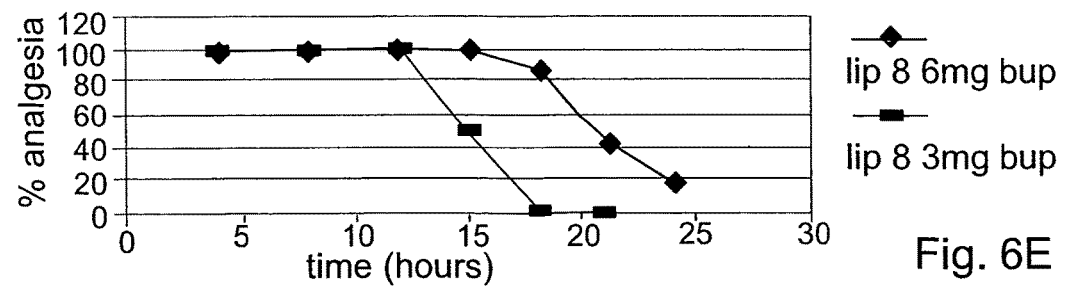
Figure 6F:
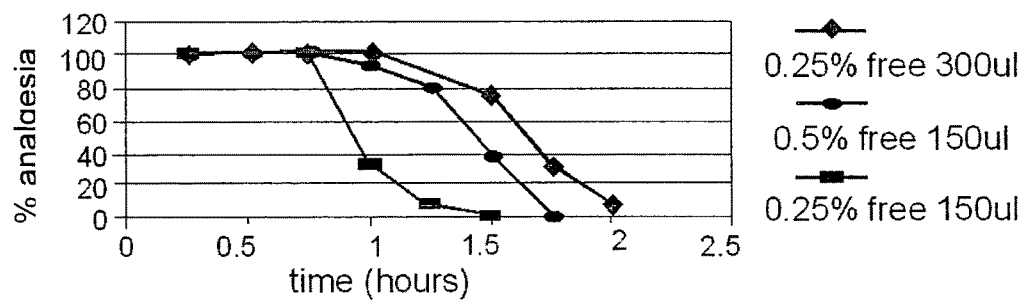

Similar results are also presented in FIGS. 4A-4B showing the kinetics of BUP release from LV-ALG encapsulated LMVV (HSPC100/C16SPM/CHOL 3/3/4) beads at 4° C., 25° C. and 37° C. Specifically, FIGS. 4A and 4B show that the release rate of BUP from the LMVV embedded in ALG beads at 37° C. reaches plateau after about 24 hours. The of BUP release rates of ALG-LMVV-BUP are similar to those of the LMVV loaded BUP (FIGS. 1A, 1B; 2A, 2B and 3A, 3B), suggesting that at physiological temperature of 37° C. the encapsulation of the LMVV-BUP in the cross linked Ca alginate hydrogel did not affect BUP release rate namely, it would not reduce the efficacy of the formulation at use. Further, ALG-LMVV-BUP system based on LMVV composed of HSPC100/C16SPM/CHOL 3/3/4 (mole ratio) exhibited low release rates at 4° C. Thus, the LMVV-BUP was stable during 4° C. storage.

Further, MPS release from LV-ALG embedded LMVV (HSPC100/SPM/CHOL 3/3/4) or LV-ALG embedded SUV (HSPC/CHOL/PEG) at 37° C., into the aqueous storage medium, was examined. Specifically, the following results were obtained:

(I) ALG-LMVV-MPS beads: the release rate of free MPS (free form) from ALG after 1 week storage at 37° C. was 70%. This rate is slower from that achieved for ALG-LMVV-BUP beads (without being bound by theory, this probably related to the higher octanol to buffer distribution coefficient or log D). These results are also comparable with the values obtained with the BUP formulation described elsewhere (FIG. 1, in Grant et al 2001, Pharma Res. 18 336-343), and with the values for MPS (described in Table 1 in Avnir et al 2008 ibid) which enables its faster trans-membrane diffusion.

(II) ALG-SUV-MPS beads: This system showed a very different behavior from the ALG systems encapsulated LMVV as it demonstrate the release of intact SUV-MPS and not free MPS. This was measured by the release of MPS and phospholipid together. This is very different from the situation when LMVV-drug is used where only drug is released into the storage medium and not any phospholipid (see above) During incubation on ALG-SUV-MPS at 37° C. 8.7% of SUV-MPS were released to the storage medium after 24 hours and 75% SUV-MPS was released after 1 week.

These results show that there is a size limitation for retaining the liposomes within the Ca alginate cross linked hydrogel. While SUV-MPS were released from the hydrogel, LMVV were safely retained therein.

It should be noted that disposal of the aqueous storage medium in which the LV-ALG embedded LMVV or LV-ALG embedded SUV was stored and addition of fresh storage medium did not lead to substantial further release of MPS to the storing medium, i.e. the level of free MPS in the fresh medium was almost zero.

FIG. 7, FIGS. 9A-9Q, FIGS. 10A-10E and FIG. 11A-11E describe the basic relevant features of the ALG-LMVV-BUP system.

Figure 7:
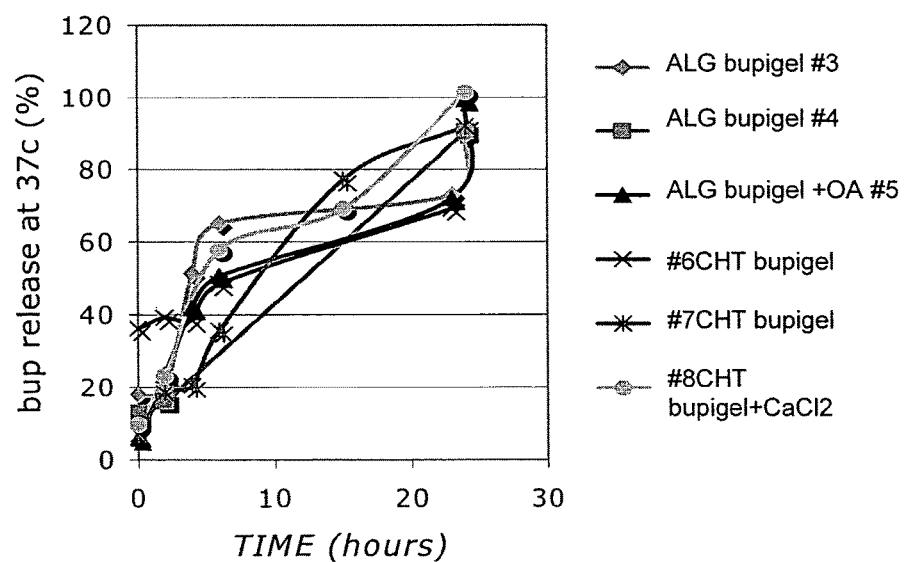
FIG. 7 shows the kinetics of bupivacaine release at 37° C. from LMMV composed of HSPC100/C16SPM/CHOL (3/3/4 mole ratio) embedded in: alginate hydrogel (ALG) cross-linked with $Ca^{++}$ ions (referred to as ALG bupigel #3 and #4, as defined in Example 2 hereinbelow), ALG bupigel de-crosslinked with oxalic acid (ALG bupigel+OA, #5 as defined in Example 2 hereinbelow), chitosan (CHT) cross-linked with oxalate (referred to as CHT bupigel #6 or #7 as defined in Example 2 hereinbelow) and CHT bupigel de-crosslinked with $CaCl_2$ (#8 CHT bupigel+$CaCl_2$ as defined in Example 2 hereinbelow).
Figure 8:
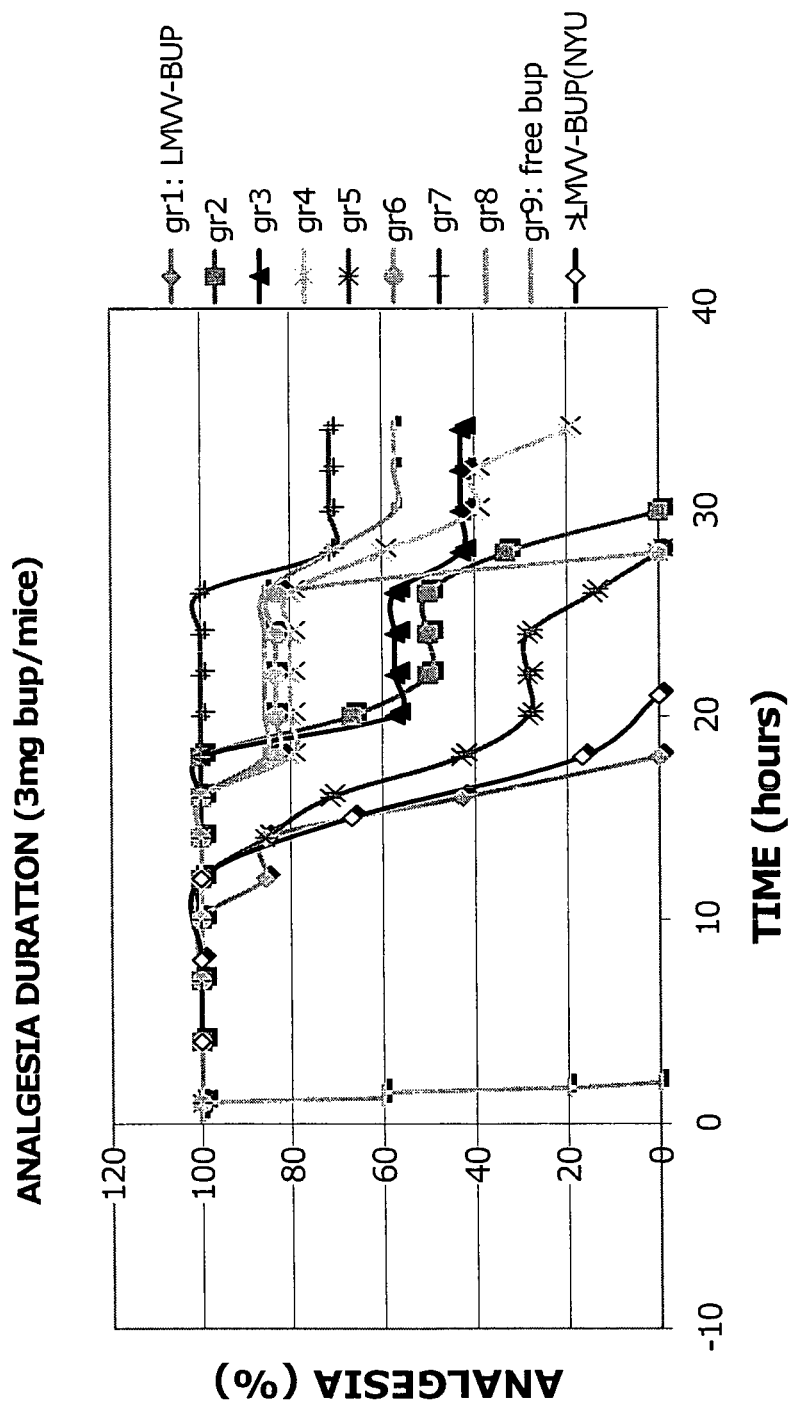
FIG. 8 describes the in vivo analgesia duration achieved for LMVV (composed of HSPC100/C16SPM/CHOL having a 3/3/4 mole ratio) loaded with BUP via trans-membrane AS gradient and embedded in: alginate-Ca hydrogel (groups 2-5, as defined in Example 2 hereinbelow), chitosan-oxalate (groups 6-8, as defined in Example 2 hereinbelow); un-embedded Bup loaded LMVV (group 1) and control group (group 9, as defined in Example 2 hereinbelow) of free Bup.
Figure 9A:
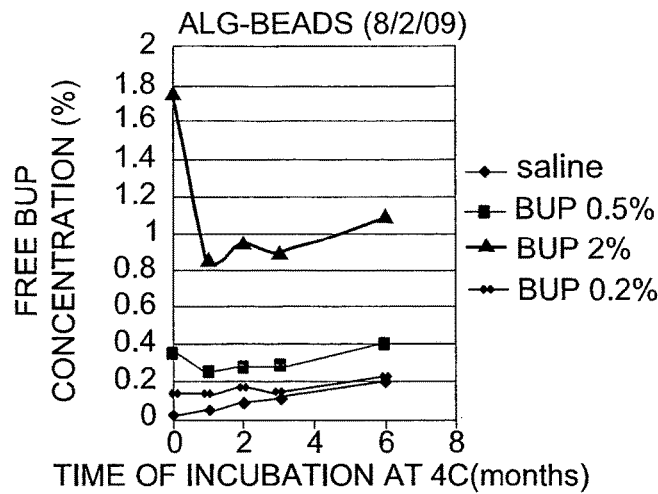
FIGS. 9A-9L describe and compare the change in level of free Bup (% of free Bup in storage media) during storage at 4° C. of LMVV (HSPC100/C16SPM/CHOL having 3/3/4 mole ratio) loaded with Bup using AS trans-membrane gradient embedded in Ca-crosslinked alginate hydrogel (ALG-Beads) when stored in various storage media.
Figure 9B:
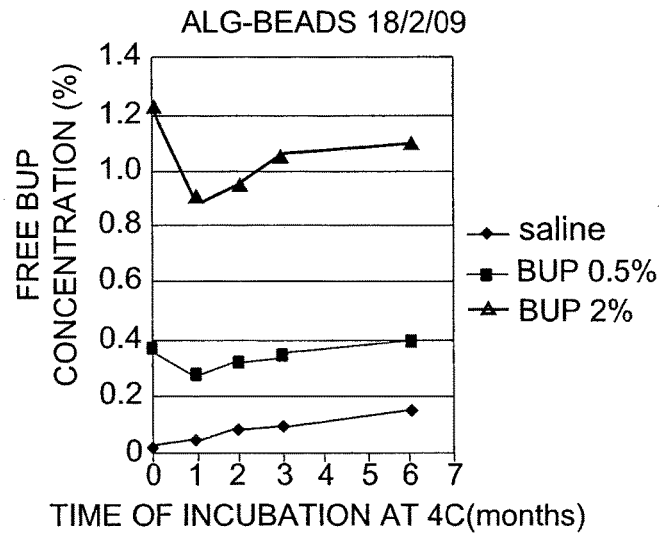
Figure 9C:
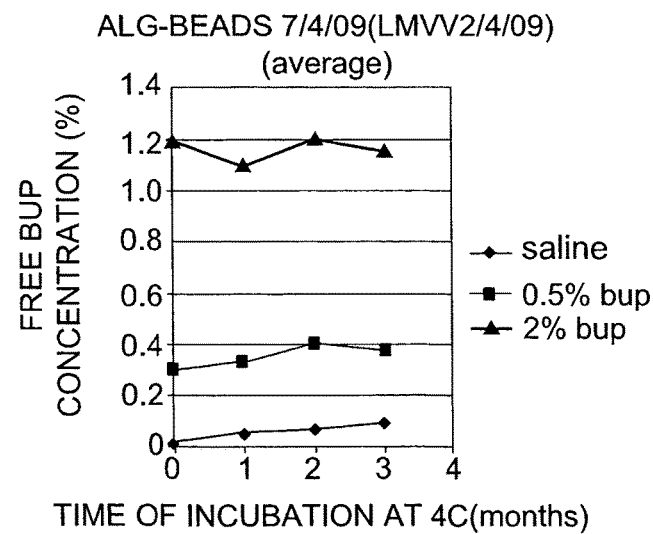
Figure 9D:
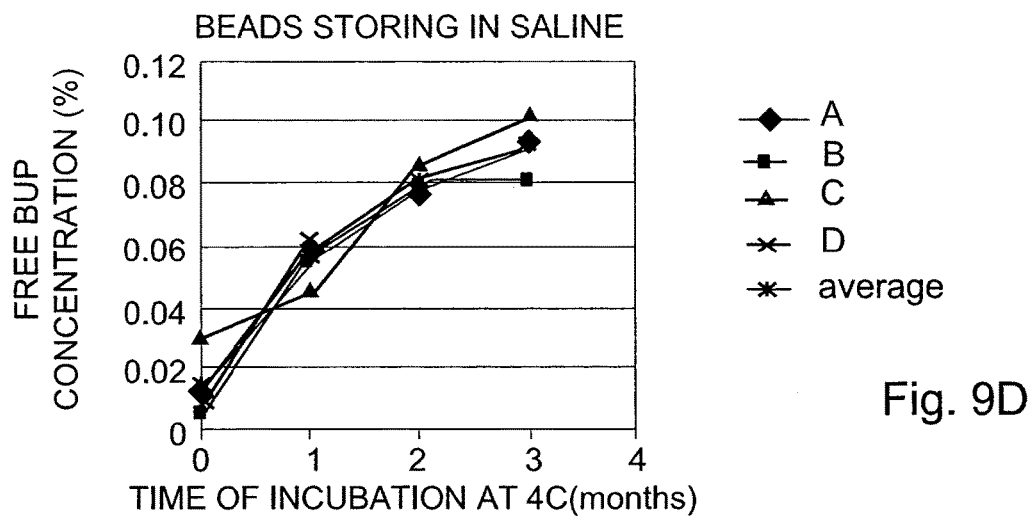
Figure 9E:
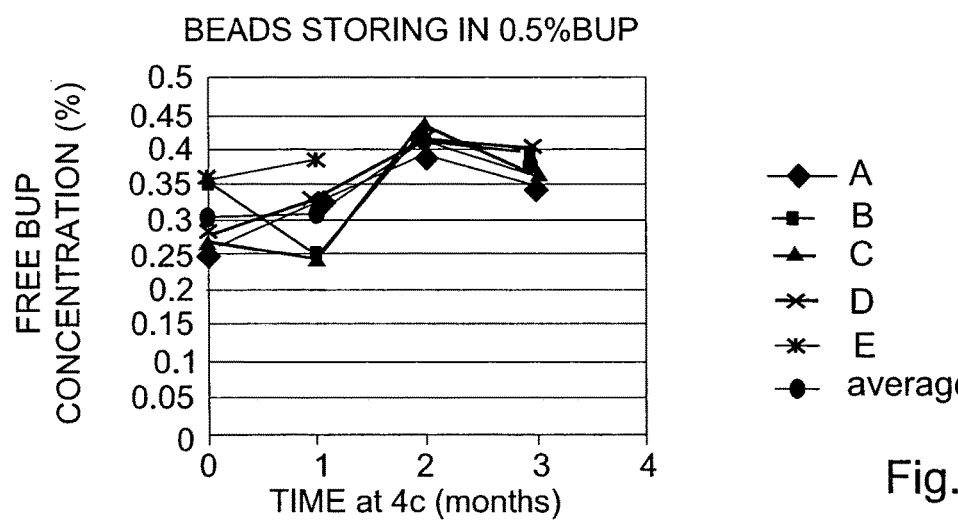
Figure 9F:
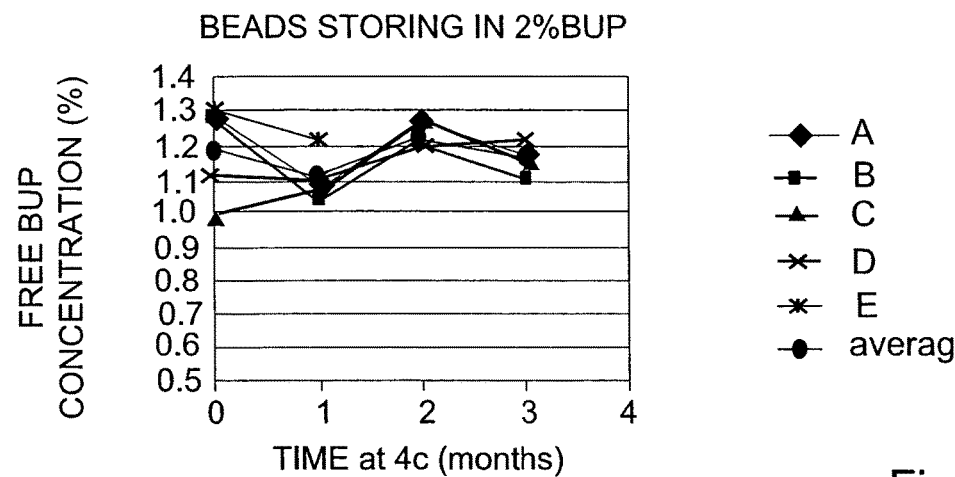
Figure 9G:
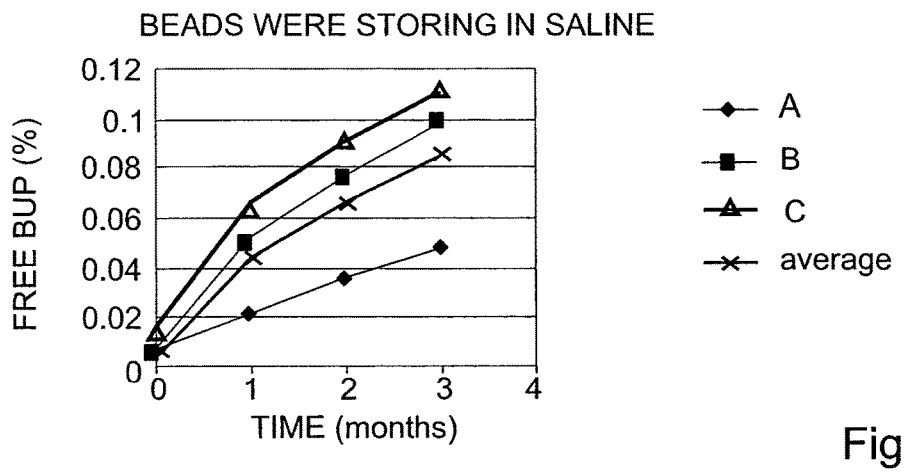
Figure 9H:
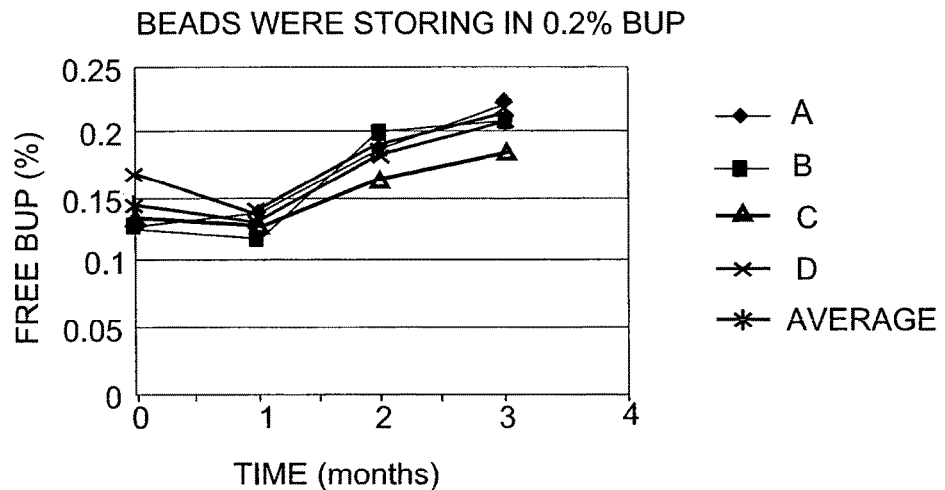
Figure 9I:
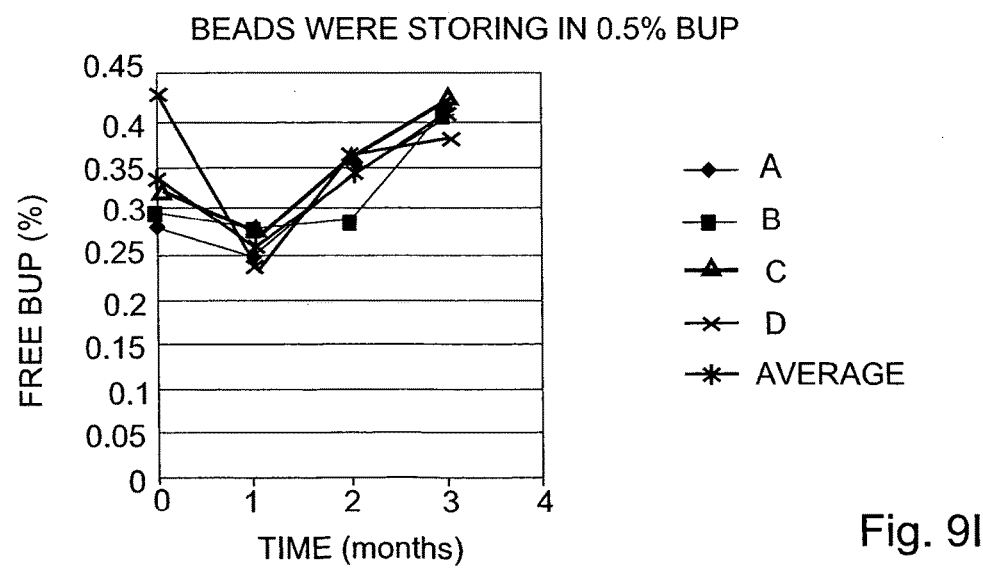
Figure 9J:
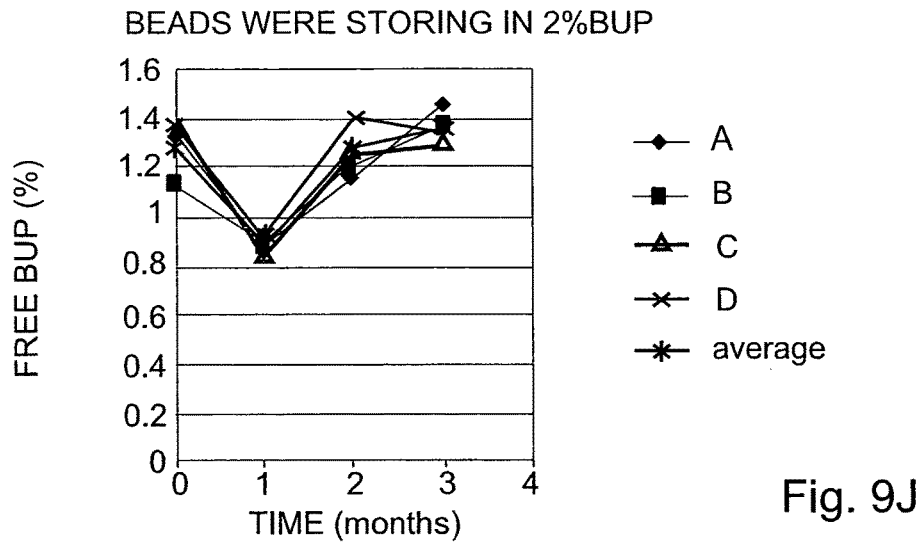
Figure 9K:
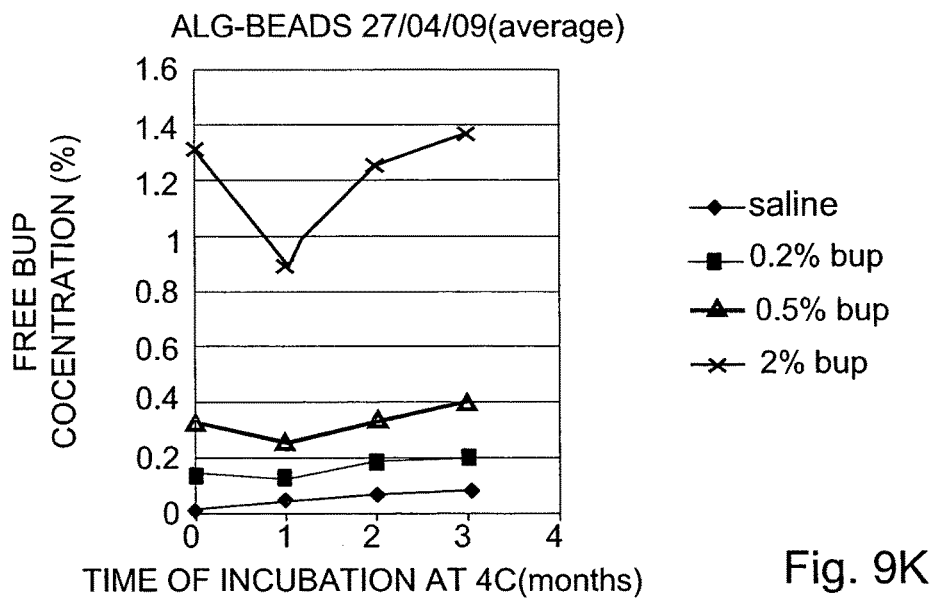
Figure 9L:
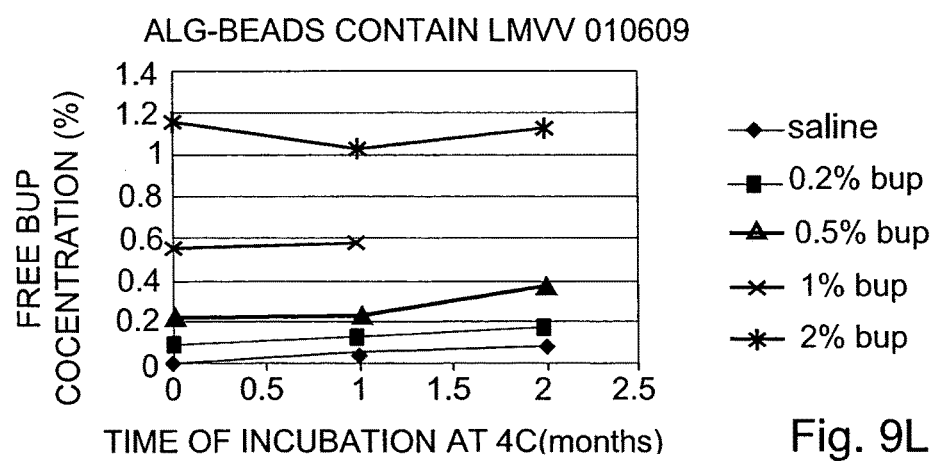
Figure 9M:
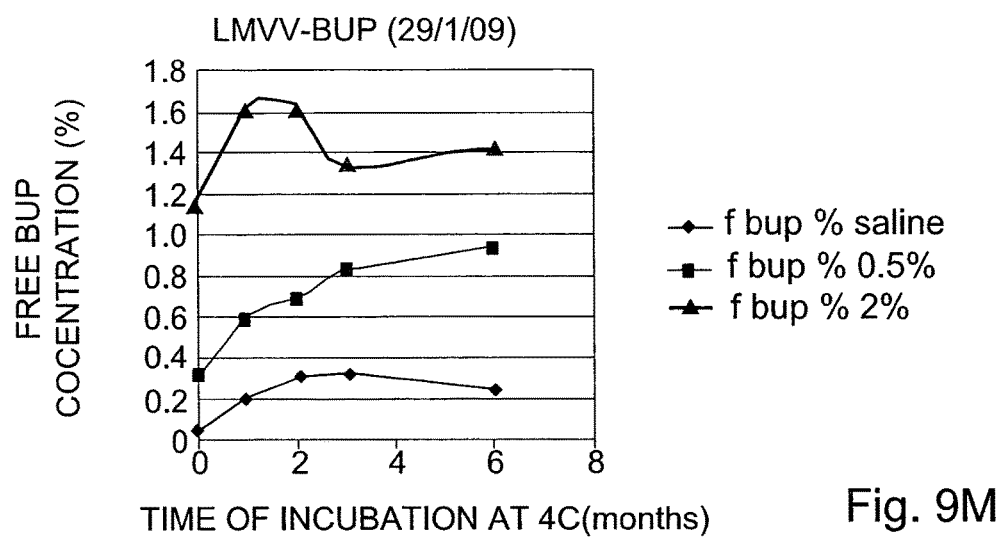
FIGS. 9M-9Q describe and compare the change in level of free bupivacaine (% of free Bup in storage medium) of LMVV (HSPC100/C16SPM/CHOL having 3/3/4 mole ratio) loaded with Bup via the AS trans-membrane not embedded in hydrogels when stored in various storage media at 4° C.
Figure 9N:
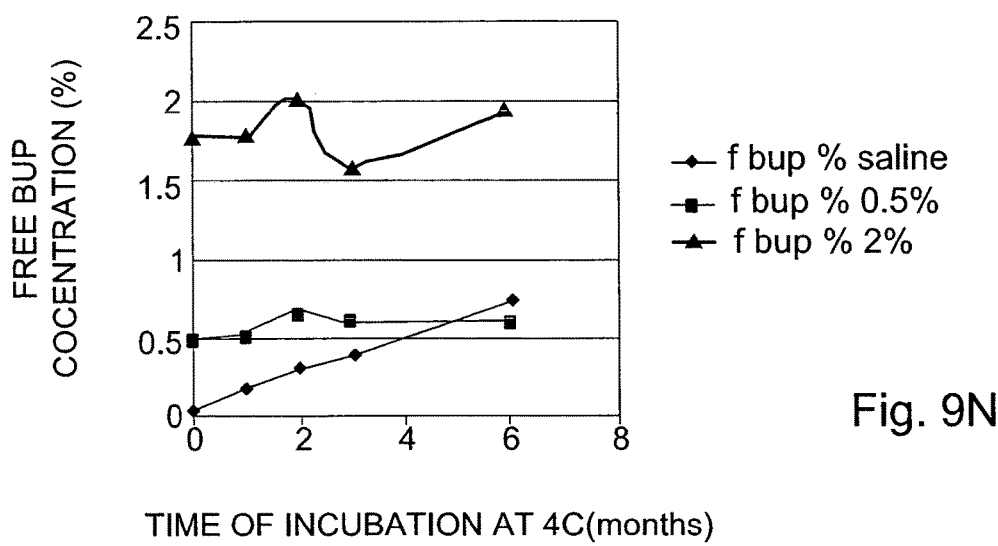
Figure 9O:
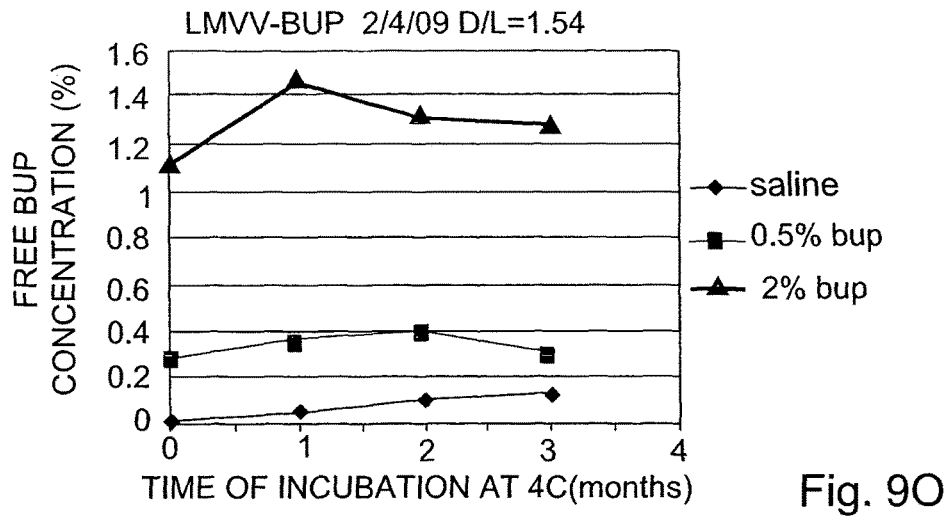
Figure 9P:
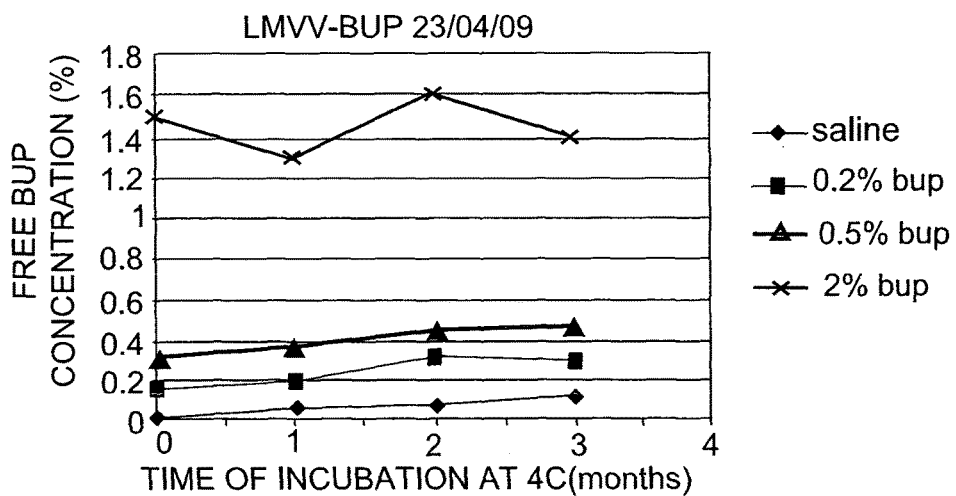
Figure 9Q:
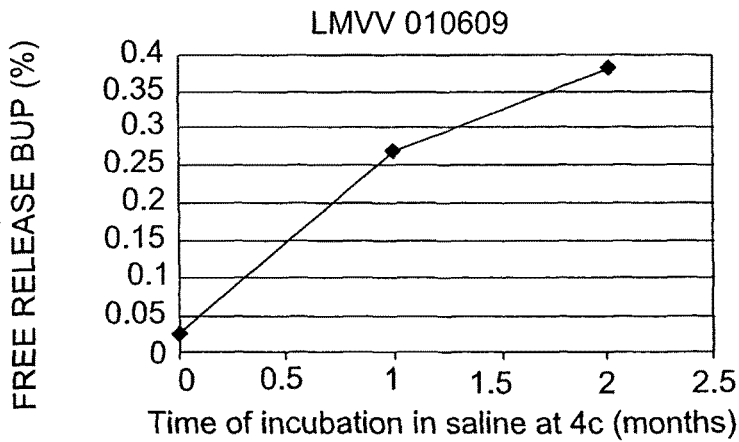
Figure 10C:
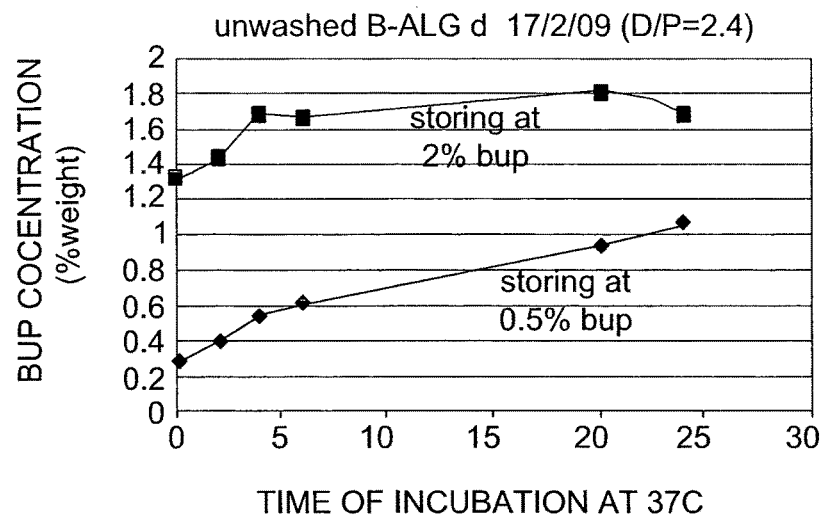
FIG. 10C describes the change in Bup level in the storage media of the preparations incubated in their original storage media (0.5 and 2.0% Bup) at 37° C. for 25 hours.
Figure 10D:
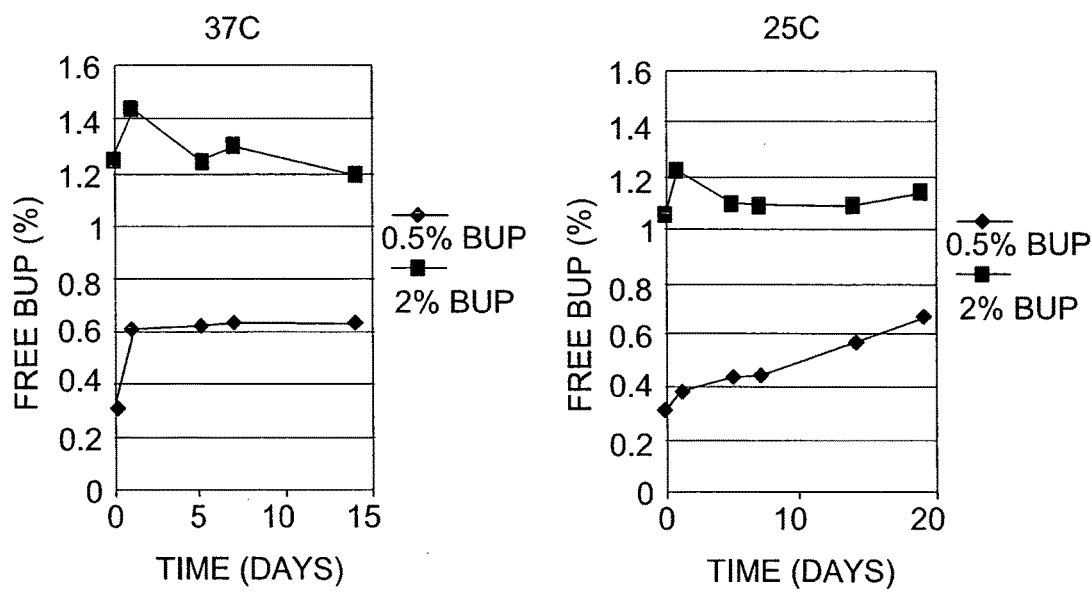
FIG. 10D is an extension of data from FIG. 10C to 15 days of incubation.

Specifically, FIG. 7 shows the kinetics of bupivacaine release at 37° C. from LMMV composed of HSPC100/C16SPM/CHOL (3/3/4 mole ratio) embedded in: alginate hydrogel (ALG) cross-linked with $Ca^{++}$ ions (referred to as ALG bupigel #3 and #4, as defined in Example 2 hereinbelow), ALG bupigel de-crosslinked with oxalic acid (ALG bupigel+OA, #5 as defined in Example 2 hereinbelow), chitosan (CHT) cross-linked with oxalate (referred to as CHT bupigel #6 or #7 as defined in Example 2 hereinbelow) and CHT bupigel de-crosslinked with $CaCl_2$ (#8 CHT bupigel+$CaCl_2$ as defined in Example 2 hereinbelow).

describe and compare the change in level of free Bup (% of free Bup in storage media) during storage at 4° C. of LMVV (HSPC100/C16SPM/CHOL having 3/3/4 mole ratio) loaded with Bup using AS trans-membrane gradient embedded in Ca-crosslinked alginate hydrogel (ALG-Beads) when stored in various storage media. FIGS. 9A-9B shows the average effect of storage (6 months) in saline, 0.2%, 0.5%, or 2.0% Bup solutions (average of different batches of ALG-Beads produced according to the methods of the invention). FIG. 9C shows the average effect of storage (3 months) in saline 0.5%, 2.0% Bup solutions. FIGS. 9D to 9F describe and compare the change in level of free Bup (% free Bup in the different storage media) during storage at 4° C. of the different batches (herein denoted as A, B, C, D, E and an average plot) of LMVV (HSPC100/C16SPM/CHOL having 3/3/4 mole ratio) loaded with Bup using AS trans-membrane gradient embedded in Ca-cross-linked alginate hydrogel when stored in various storage media, during 3 months: saline (FIG. 9D), 0.5% BUP (FIG. 9E) and 2.0% BUP (FIG. 9F). FIGS. 9G-9K describe and compare the change in level of free Bup (% of free Bup in the different storage media) during storage at 4° C. of the different batches (herein denoted as A, B, C, D, E and an average plot) LMVV (HSPC100/C16SPM/CHOL having 3/3/4 mole ratio) loaded with Bup using AS trans-membrane gradient embedded in Ca-crosslinked alginate hydrogel when stored in various storage media, during 3 months in: saline (FIG. 9G), in 0.2% BUP (FIG. 9H), in 0.5% BUP (FIG. 9I) or in 2.0% BUP (FIG. 9J). FIG. 9K describes the average effect of storage (3 months) in saline, 0.2%, 0.5%, or 2.0% Bup solutions (average of different batches of ALG-ALG-Beads described in FIG. 9G to 9J). FIG. 9L shows the average effect of storage (2 months) in saline 0.5%, 2.0% Bup solutions. FIGS. 9M-9Q describe and compare the change in level of free bupivacaine (% of free Bup in storage medium) of LMVV (HSPC100/C16SPM/CHOL having 3/3/4 mole ratio) loaded with Bup via the AS trans-membrane not embedded in hydrogels when stored in various storage media at 4° C. (FIGS. 9M, 9N and 9O in saline, 0.5%, or 2.0% Bup solutions and FIG. 9P in saline, 0.2%, 0.5%, or 2.0% Bup solutions). FIG. 9Q describes a separate experiment of 2 months follow-up upon storage in saline without hydrogel. All storage media in FIGS. 9A-9Q were brought to 285 mOsmole by addition of NaCl solution to retain iso-tonicity FIG. 10A-10D describe the change in level of free Bup (% of free Bup in storage media) in different storage media of LMVV (HSPC100/C16SPM/CHOL3/3/4 mole ratio) loaded with Bup via trans-membrane AS gradient and embedded in Ca cross-linked alginate. Three storage media were used (saline, 0.5% Bup, and 2.0% Bup, all storage media were brought to iso-tonicity of 285 mOsmole with NaCl solution). These were stored for 40 days at 4° C. and than used in the experiments described in FIG. 10A-10D). FIGS. 10A and 10B describe release of Bup after the removal of storage media by washing with saline followed by 30 hours of incubation at 37° C. throughout this time amount of drug in the hydrogel media (saline) was measured (FIG. 10A) and also described as % Bup released (FIG. 10B). FIG. 10C describes the change in Bup level in the storage media of the preparations incubated in their original storage media (0.5 and 2.0% Bup) at 37° C. for 25 hours. FIG. 10D is an extension of data from FIG. 10C to 15 days of incubation, FIG. 10E shows the change in Bup concentration in 0.5% Bup, and 2.0% Bup storage media of the above described Bup loaded LMVV after incubation at a temperature of 25° C. for 20 days.

Figure 11A:
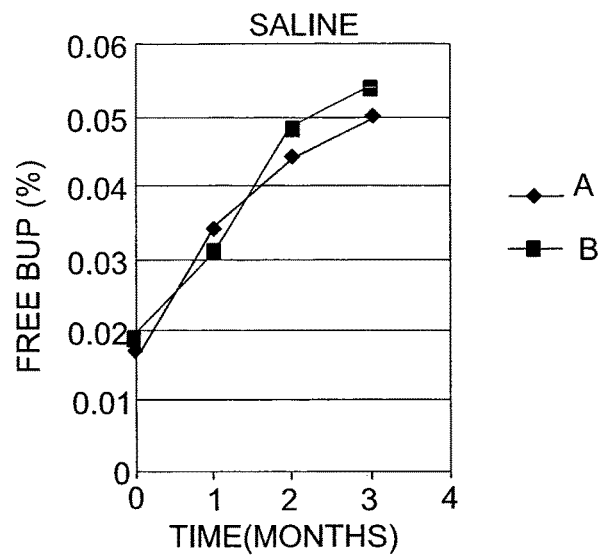
FIGS. 11A-11E describe change in level of free Bup (% of free Bup in storage media) over a storage period of 3 months at 4° C., in different liquid storage media of ALG-LMVV-BUP (HSPC100/C16SPM/CHOL 3/3/4 mole ratio), remote loaded by trans-membrane AS gradient. The storage media used were: Saline (FIG. 11A), 0.2% BUP (FIG. 11B), 0.5% BUP (FIG. 11C), and 2.0% BUP (FIG. 11D).
Figure 11B:
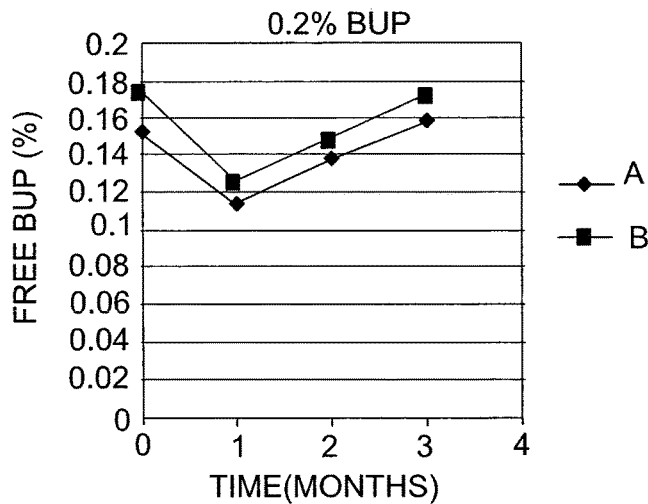
Figure 11C:
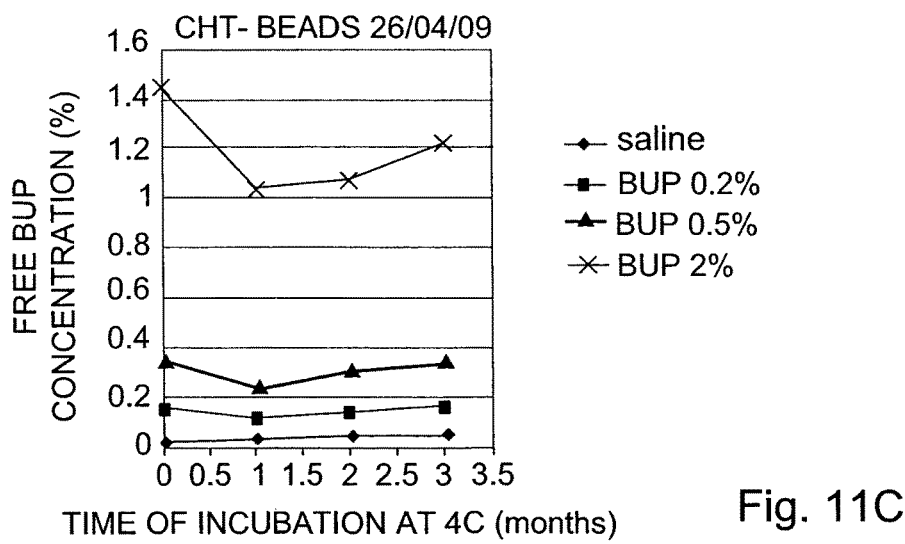
Figure 11D:
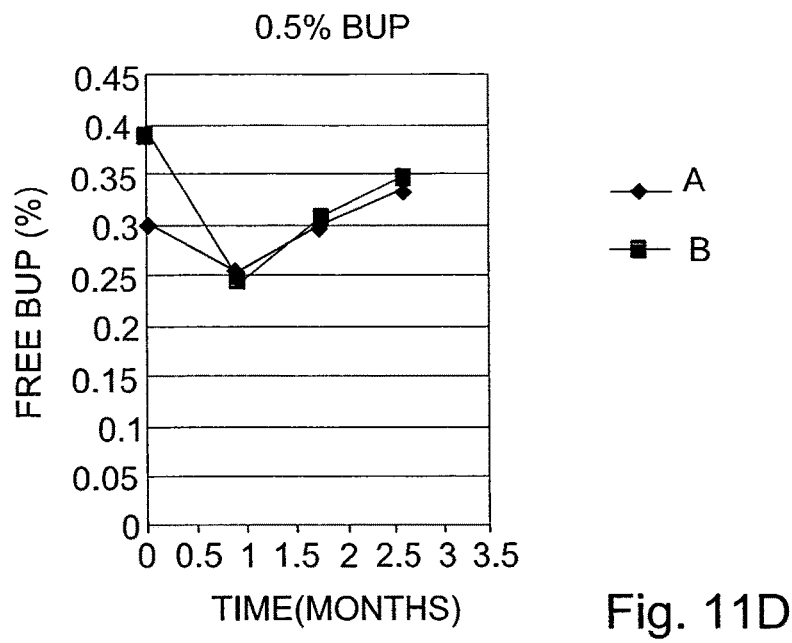
Figure 11E:
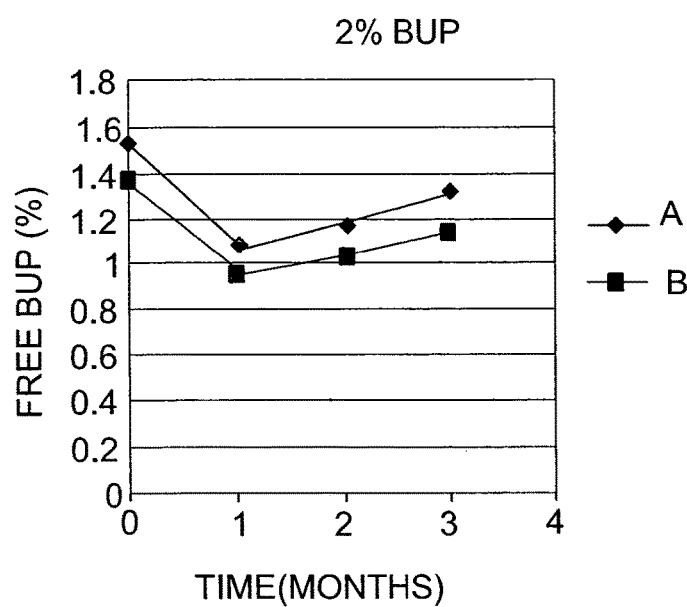

FIGS. 11A-11E describe change in level of free Bup (% of free Bup in storage media) over a storage period of 3 months at 4° C., in different liquid storage media of ALG-LMVV-BUP (HSPC100/C16SPM/CHOL 3/3/4 mole ratio), remote loaded by trans-membrane AS gradient. The storage media used were: Saline (FIG. 11A), 0.2% BUP (FIG. 11B), 0.5% BUP (FIG. 11C), and 2.0% BUP (FIG. 11D). FIG. 11E summarizes the changes in Bup concentration over a storage period of 3 months at 4° C., in different liquid storage media of CHT-LMVV-BUP (HSPC100/C16SPM/CHOL 3/3/4 mole ratio), remote loaded by trans-membrane AS gradient. The storage media used were: Saline, 0.2% BUP, 0.5% BUP, and 2.0% BUP.

In Vivo Experiments
Bupivacaine Loaded LMVV Preparations

FIGS. 5A-5C and 6A-6F summarize results obtained with 8 LMVV-BUP formulations. These were prepared (as specified below) under sterile conditions and were tested for sterility in the Clinical Microbiology Department, Hadassah Hospital, Jerusalem, Israel. These liposomes were also characterized for their size distribution, drug to PL mole ratio and rate of BUP release at 4° C. and 37° C. The liposomes were shipped from Jerusalem Israel to Dr G. J. Grant, Department of Anesthesiology, NYU, School of Medicine, NYC, USA at controlled temperature of 2° C.-8° C. Using sensors attached to the shipped samples it was found that the temperature was kept at the desired rang suring shipment. HPLC analysis before shipment and after arrival to destination indicated that no leakage during shipment took place. This is described as "In vivo Experiment 1" or NYU experiment.

TABLE 7

Characterization of liposomes composition and properties of formulations used in in vivo experiment 1

| sample | date of preparation | sample number | gradient sort | liposomes type | pellet volume ml | total volume ml | % of free bupiv. | $y = 141.555x$ Bupivicaine (total) mM | Pi µmol/ml = mmol/l = mM | Ratio Bupivicaine/ Pi mM Bupivicaine/ mM Pi |
|---|---|---|---|---|---|---|---|---|---|---|
| H100/SPM$_{C16}$/CHOL 3/3/4 | 15 Jul. 2007 | 1 | AS (in saline) 1 ml lipos (instead 0.5 ml) + 2 ml 4.5% bup. | MLV | 3.5 | 15 | 5.08 | 17.11 | 28.12 | 0.61 |
| | 09 Jul. 2007 | 2 | CaAc (in PBS) | MLV | 4 | 15 | 3.09 | 17.86 | 19.53 | 0.91 |
| | 10 Jul. 2007 | 3 | AS (in saline) | LMVV | 5 | 15 | 2.81 | 27.36 | 13.71 | 2.00 |
| | 11 Jul. 2007 & 15 Jul. 2007 | 4 | CaAc (in PBS) | LMVV | 15 | 30 | 3.56 | 17.28 | 21.06 | 0.82 |
| H100/CHOL 6/4 | 16 Jul. 2007 | 5 | AS (in saline) | LMVV | 7 | 15 | 3.27 | 32.23 | 15.91 | 2.03 |
| HSPC/CHOL 6/4 | 16 Jul. 2007 | 6 | AS (in saline) | LMVV | 6 | 15 | 6.81 | 33.32 | 14.89 | 2.24 |
| H100/CHOL 6/4 | 17 Jul. 2007 | 7 | CaAc (in PBS) | LMVV | 7 | 15 | 6.11 | 14.67 | 19.82 | 0.74 |
| H100/SPM$_{C16}$/CHOL 3/3/4 | 18 Jul. 2007 | 8 | 6% passive | LMVV | 4 | 15 | 1.20 | 23.00 | 20.13 | 1.14 |

All liposomal formulations were analyzed for free non liposomal BUP and total BUP before the in vivo experiment followed by their concentration to reach the level of 2% (w/w) BUP (for liposome formulations #1, 2, 3, 5, 6, 8) and to 1% (w/w BUP for liposome formulations #4 & 7). BUP was loaded into the liposomes either by active loading (CA or AS gradient) or by passive loading as described in Table 8.

TABLE 8

Liposome characterization prior to Experiment 1 performance

| # | Lipids | Loading technique | Liposome type | % free BUP |
|---|---|---|---|---|
| 1 | H100/SPM/CHOL | AS gradient | MLV | 3.88 |
| 2 | H100/SPM/CHOL | CA gradient | MLV | 3.95 |
| 3 | H100/SPM/CHOL | AS gradient | LMVV | 3.69 |
| 4 | H100/SPM/CHOL | CA gradient | LMVV | 4.52 |
| 5 | H100/CHOL | AS gradient | LMVV | 3.68 |
| 6 | HSPC/CHOL | AS gradient | LMVV | 7.80 |
| 7 | H100/CHOL | CA gradient | LMVV | 7.66 |
| 8 | H100/SPM/CHOL | 6% BUP passive loading | LMVV | 1.90 |

Analgesic Efficacy in Mouse Model:

Testing for analgesia was done by electrical stimulation of the skin directly overlying the abdomen at the site of injection using a current generator (model S48, Grass Instruments) as described in Grant et al 2001. (G. J. Grant et al, pharmaceutical research, vol 18, no 3, 336-343, 2001), and in Methods above.

Mice (male Swiss-Webster 26±3 gr) were tested prior to injection to determine the vocalization threshold than were injected with liposomal BUP or free BUP than followed by determination of analgesia duration (The duration of the main in vivo screening study was 2 days and started after a preliminary study using two different injection volumes of formulation #4 (referred to as the PILOT in Table 9A) was performed.

In order to evaluate the effect of altering the volume and BUP concentration of the injection, in each of the 7 groups (all groups except group 4) three mice received 150 µl of the 2% formulation and 3 mice received 300 µl 1.0% (achieved by a dilution of the 2% formulation).

It has been previously determined (Grant et al. 2004, ibid., and U.S. Pat. No. 6,162,462) that free (standard, non liposomal) BUP provide an analgesic effect for approximately 75 minutes post injection.

The analgesic efficacy of the various formulations 1 to 8, at different BUP concentration, different injection volume etc. is presented in Tables 9A to 9C. In these Tables, an numeric score of "1" denotes full analgesia, a numeric score of "0" was given when there was no analgesic effect, and a numeric value of "10" when there was partial analgesia.

In Table 9A results of mice injected with LMVV formulation #4, two mice with 300 µl and two mice with 150 µl are presented as "PILOT 1-4" Testing was done at 4, 17, and 21 hours following injection.

In all other 7 mice groups the mice were injected with either 300 µl of liposomes containing 1.0% BUP or 150 µl of liposomes containing 2.0% BUP. So total BUP injected per mouse was the same (3 mg/mouse).

The results of the pilot study are also described in Table 9A.

TABLE 9A

Duration of analgesia at different BUP concentrations (administered as liposomal-BUP) and different injected volumes Aug. 9, 2007
1 indicates mice under analgesia, 0 indicates mice lacks analgesia; 10 indicates mice is under partial analgesia
Note: On Aug. 8, 2007, we injected four animals with LMW formulation #4 (2 animals with 300 ul and 2 mice with 150 ul); testing was done at 4, 17, and 21 hours. These are labeled "PILOT" in the spreadsheet below

| animal # | lipo # | bup conc | volume (ul) | mg Bup | 4 hr | 8 hr | 12 hr | 15 hr | 18 hr | 21 hr |
|---|---|---|---|---|---|---|---|---|---|---|
| 1 | 1 | 2% | 150 | 3 | 1 | 1 | 10 | 0 | 0 | 0 |
| 2 | 1 | 2% | 150 | 3 | 1 | 1 | 1 | 1 | 0 | 0 |
| 3 | 1 | 2% | 150 | 3 | 1 | 1 | 1 | 1 | 0 | 0 |
| 4 | 1 | 1% | 300 | 3 | 1 | 1 | 1 | 0 | 0 | 0 |
| 5 | 1 | 1% | 300 | 3 | 1 | 1 | 1 | 0 | 0 | 0 |
| 6 | 1 | 1% | 300 | 3 | 1 | 1 | 1 | 0 | 0 | 0 |
| 7 | 2 | 2% | 150 | 3 | 1 | 1 | 1 | 1 | 0 | 0 |
| 8 | 2 | 2% | 150 | 3 | 1 | 1 | 0 | 0 | 0 | 0 |
| 9 | 2 | 2% | 150 | 3 | 1 | 1 | 1 | 0 | 0 | 0 |
| 10 | 2 | 1% | 300 | 3 | 1 | 1 | 1 | 1 | 0 | 0 |
| 11 | 2 | 1% | 300 | 3 | 1 | 1 | 0 | 0 | 0 | 0 |
| 12 | 2 | 1% | 300 | 3 | 1 | 1 | 0 | 0 | 0 | 0 |
| 13 | 3 | 2% | 150 | 3 | 1 | 1 | 1 | 1 | 0 | 0 |
| 14 | 3 | 2% | 150 | 3 | 1 | 1 | 1 | 0 | 0 | 0 |
| 15 | 3 | 2% | 150 | 3 | 1 | 1 | 1 | 1 | 0 | 0 |
| 16 | 3 | 1% | 300 | 3 | 1 | 1 | 1 | 0 | 0 | 0 |
| 17 | 3 | 1% | 300 | 3 | 1 | 1 | 1 | 1 | 1 | 0 |
| 18 | 3 | 1% | 300 | 3 | 1 | 1 | 1 | 1 | 0 | 0 |
| 19 | 4 | 1% | 300 | 3 | 1 | 1 | 1 | 1 | 1 | 0 |
| 20 | 4 | 1% | 300 | 3 | animal eliminated from study | | | | | |
| 21 | 4 | 1% | 300 | 3 | 1 | 1 | 1 | 10 | 10 | 0 |
| 22 | 4 | 1% | 300 | 3 | 1 | 1 | 1 | 1 | 10 | 10 |
| 23 | 4 | 1% | 300 | 3 | 1 | 1 | 1 | 1 | 10 | 0 |
| 24 | 4 | 1% | 300 | 3 | 1 | 1 | 1 | 1 | 0 | 0 |
| | | | | | | | | | 17 hr | |
| PILOT 1 | 4 | 1% | 300 | 3 | 1 | | | | 1 | 0 |
| PILOT 2 | 4 | 1% | 300 | 3 | 1 | | | | 1 | 0 |
| PILOT 3 | 4 | 1% | 150 | 1.5 | 1 | | | | 0 | |
| PILOT 4 | 4 | 1% | 150 | 1.5 | 1 | | | | 0 | |
| 25 | 5 | 2% | 150 | 3 | 1 | 1 | 1 | 0 | 0 | 0 |

TABLE 9A-continued

Duration of analgesia at different BUP concentrations (administered as liposomal-BUP) and different injected volumes Aug. 9, 2007
1 indicates mice under analgesia, 0 indicates mice lacks analgesia; 10 indicates mice is under partial analgesia
Note: On Aug. 8, 2007, we injected four animals with LMW formulation #4 (2 animals with 300 ul and 2 mice with 150 ul); testing was done at 4, 17, and 21 hours. These are labeled "PILOT" in the spreadsheet below

| animal # | lipo # | bup conc | volume (ul) | mg Bup | 4 hr | 8 hr | 12 hr | 15 hr | 18 hr | 21 hr |
|---|---|---|---|---|---|---|---|---|---|---|
| 26 | 5 | 2% | 150 | 3 | 1 | 1 | 1 | 1 | 1 | 0 |
| 27 | 5 | 2% | 150 | 3 | 1 | 1 | 1 | 0 | 0 | 0 |
| 28 | 5 | 1% | 300 | 3 | 1 | 1 | 1 | 1 | 0 | 0 |
| 29 | 5 | 1% | 300 | 3 | 1 | 1 | 1 | 0 | 0 | 0 |
| 30 | 5 | 1% | 300 | 3 | 1 | 1 | 10 | 0 | 0 | 0 |
| 31 | 6 | 2% | 150 | 3 | 1 | 1 | 0 | 1 | 0 | 0 |
| 32 | 6 | 2% | 150 | 3 | 1 | 1 | 1 | 1 | 0 | 0 |
| 33 | 6 | 2% | 150 | 3 | 1 | 0 | 0 | 0 | 0 | 0 |
| 34 | 6 | 1% | 300 | 3 | 1 | 1 | 0 | 0 | 0 | 0 |
| 35 | 6 | 1% | 300 | 3 | 1 | 1 | 1 | 10 | 10 | 0 |
| 36 | 6 | 1% | 300 | 3 | 1 | 1 | 1 | 0 | 0 | 0 |
| 37 | 7 | 1% | 300 | 3 | 1 | 1 | 1 | 10 | 10 | 0 |
| 38 | 7 | 1% | 300 | 3 | 1 | 1 | 1 | 1 | 0 | 0 |
| 39 | 7 | 1% | 300 | 3 | 1 | 0 | 0 | 0 | 0 | 0 |
| 40 | 7 | 1% | 300 | 3 | 1 | 1 | 0 | 0 | 0 | 0 |
| 41 | 7 | 1% | 300 | 3 | 1 | 1 | 1 | 1 | 0 | 0 |
| 42 | 7 | 1% | 300 | 3 | 1 | 1 | 1 | 1 | 0 | 0 |
| 43 | 8 | 2% | 150 | 3 | 1 | 1 | 1 | 1 | 0 | 0 |
| 44 | 8 | 2% | 150 | 3 | 1 | 1 | 1 | 0 | 0 | 0 |
| 45 | 8 | 2% | 150 | 3 | 1 | 1 | 1 | 0 | 0 | 0 |
| 46 | 8 | 1% | 300 | 3 | 1 | 1 | 1 | 1 | 0 | 0 |
| 47 | 8 | 1% | 300 | 3 | 1 | 1 | 1 | 1 | 0 | 0 |
| 48 | 8 | 1% | 300 | 3 | 1 | 1 | 1 | 0 | 0 | 0 |

TABLE 9B

Duration of analgesia at different free BUP concentrations and at different injected volumes Aug. 13, 2007
Standard Bupivacaine (Control) 1 = analgesia; 0 = no analgesia; 10 = partial analgesia

| Mouse | #Bup Conc | Volume (ul) | mg Bup | 15 min | 30 min | 45 min | 60 min | 75 min | 90 min | 105 min | 120 min | 135 min |
|---|---|---|---|---|---|---|---|---|---|---|---|---|
| 1 | 0.25% | 150 | 0.375 | 1 | 1 | 1 | 0 | 0 | 0 | | | |
| 2 | 0.25% | 150 | 0.375 | 1 | 1 | 1 | 0 | 0 | 0 | | | |
| 3 | 0.25% | 150 | 0.375 | 1 | 1 | 1 | 0 | 0 | 0 | | | |
| 4 | 0.25% | 150 | 0.375 | 1 | 1 | 1 | 1 | 0 | 0 | | | |
| 5 | 0.25% | 150 | 0.375 | 1 | 1 | 1 | 1 | 10 | 0 | | | |
| 6 | 0.25% | 150 | 0.375 | 1 | 1 | 1 | 0 | 0 | 0 | | | |
| 7 | 0.25% | 150 | 0.375 | 1 | 1 | 1 | 10 | 0 | 0 | | | |
| 8 | 0.25% | 150 | 0.375 | 1 | 1 | 1 | 0 | 0 | 0 | | | |
| 1 | 0.25% | 300 | 0.75 | 1 | 1 | 1 | 1 | 0 | 0 | 0 | 0 | 0 |
| 2 | 0.25% | 300 | 0.75 | 1 | 1 | 1 | 1 | 1 | 1 | 0 | 0 | 0 |
| 3 | 0.25% | 300 | 0.75 | 1 | 1 | 1 | 1 | 1 | 10 | 10 | 0 | 0 |
| 4 | 0.25% | 300 | 0.75 | 1 | 1 | 1 | 1 | 1 | 10 | 0 | 0 | 0 |
| 5 | 0.25% | 300 | 0.75 | 1 | 1 | 1 | 1 | 1 | 1 | 1 | 10 | 0 |
| 6 | 0.25% | 300 | 0.75 | 1 | 1 | 1 | 1 | 1 | 1 | 0 | 0 | 0 |
| 7 | 0.25% | 300 | 0.75 | 1 | 1 | 1 | 1 | 1 | 1 | 0 | 0 | 0 |
| 8 | 0.25% | 300 | 0.75 | 1 | 1 | 1 | 1 | 1 | 1 | 1 | 0 | 0 |
| 1 | 0.50% | 150 | 0.75 | 1 | 1 | 1 | 1 | 1 | 0 | 0 | | |
| 2 | 0.50% | 150 | 0.75 | 1 | 1 | 1 | 1 | 1 | 0 | 0 | | |
| 3 | 0.50% | 150 | 0.75 | 1 | 1 | 1 | 1 | 1 | 10 | 0 | | |
| 4 | 0.50% | 150 | 0.75 | 1 | 1 | 1 | 1 | 0 | 0 | 0 | | |
| 5 | 0.50% | 150 | 0.75 | 1 | 1 | 1 | 1 | 1 | 1 | 0 | | |
| 6 | 0.50% | 150 | 0.75 | 1 | 1 | 1 | 1 | 1 | 10 | 0 | | |
| 7 | 0.50% | 150 | 0.75 | 1 | 1 | 1 | 1 | 1 | 1 | 0 | | |
| 8 | 0.50% | 150 | 0.75 | 1 | 1 | 1 | 10 | 10 | 0 | 0 | | |

Liposomal (LMVV) Bupivacaine Pilot Study

| Mouse # | LipoForm# | Conc. | Volume | mg Bup | 15 hr | 18 hr | 21 hr |
|---|---|---|---|---|---|---|---|
| 1 | 3 | 2% | 300 | 6 | 1 | 1 | 10 |
| 2 | 3 | 2% | 300 | 6 | 1 | 1 | 0 |
| 1 | 4 | 1% | 450 | 4.5 | 1 | 1 | 0 |
| 2 | 4 | 1% | 450 | 4.5 | 1 | 1 | 0 |

TABLE 9B-continued

Duration of analgesia at different free BUP concentrations and at different injected volumes

| 1 | 5 | 2% | 300 | 6 | 1 | 1 | 0 |
| 2 | 5 | 2% | 300 | 6 | 0 | 1 | 0 |

TABLE 9C

Analgesic effect at different free BUP concentrations and different injected volumes Aug. 13, 2007
Standard Bupivacaine (Control) 1 = analgesia; 0 = no analgesia; 10 = partial analgesia

| Mouse # | Bup Conc | Volume (ul) | mg Bup | 15 min | 30 min | 45 min | 60 min | 75 min | 90 min | 105 min | 120 min | 135 min |
|---|---|---|---|---|---|---|---|---|---|---|---|---|
| 1 | 0.25% | 150 | 0.375 | 1 | 1 | 1 | 0 | 0 | 0 | | | |
| 2 | 0.25% | 150 | 0.375 | 1 | 1 | 1 | 0 | 0 | 0 | | | |
| 3 | 0.25% | 150 | 0.375 | 1 | 1 | 1 | 0 | 0 | 0 | | | |
| 4 | 0.25% | 150 | 0.375 | 1 | 1 | 1 | 1 | 0 | 0 | | | |
| 5 | 0.25% | 150 | 0.375 | 1 | 1 | 1 | 1 | 10 | 0 | | | |
| 6 | 0.25% | 150 | 0.375 | 1 | 1 | 1 | 0 | 0 | 0 | | | |
| 7 | 0.25% | 150 | 0.375 | 1 | 1 | 1 | 10 | 0 | 0 | | | |
| 8 | 0.25% | 150 | 0.375 | 1 | 1 | 1 | 0 | 0 | 0 | | | |
| 1 | 0.25% | 300 | 0.75 | 1 | 1 | 1 | 1 | 0 | 0 | 0 | 0 | 0 |
| 2 | 0.25% | 300 | 0.75 | 1 | 1 | 1 | 1 | 1 | 1 | 0 | 0 | 0 |
| 3 | 0.25% | 300 | 0.75 | 1 | 1 | 1 | 1 | 1 | 10 | 10 | 0 | 0 |
| 4 | 0.25% | 300 | 0.75 | 1 | 1 | 1 | 1 | 1 | 10 | 0 | 0 | 0 |
| 5 | 0.25% | 300 | 0.75 | 1 | 1 | 1 | 1 | 1 | 1 | 1 | 10 | 0 |
| 6 | 0.25% | 300 | 0.75 | 1 | 1 | 1 | 1 | 1 | 1 | 0 | 0 | 0 |
| 7 | 0.25% | 300 | 0.75 | 1 | 1 | 1 | 1 | 1 | 1 | 0 | 0 | 0 |
| 8 | 0.25% | 300 | 0.75 | 1 | 1 | 1 | 1 | 1 | 1 | 1 | 0 | 0 |
| 1 | 0.50% | 150 | 0.75 | 1 | 1 | 1 | 1 | 1 | 0 | 0 | | |
| 2 | 0.50% | 150 | 0.75 | 1 | 1 | 1 | 1 | 1 | 0 | 0 | | |
| 3 | 0.50% | 150 | 0.75 | 1 | 1 | 1 | 1 | 1 | 10 | 0 | | |
| 4 | 0.50% | 150 | 0.75 | 1 | 1 | 1 | 1 | 0 | 0 | 0 | | |
| 5 | 0.50% | 150 | 0.75 | 1 | 1 | 1 | 1 | 1 | 1 | 0 | | |
| 6 | 0.50% | 150 | 0.75 | 1 | 1 | 1 | 1 | 1 | 10 | 0 | | |
| 7 | 0.50% | 150 | 0.75 | 1 | 1 | 1 | 1 | 1 | 1 | 0 | | |
| 8 | 0.50% | 150 | 0.75 | 1 | 1 | 1 | 10 | 10 | 0 | 0 | | |

Liposomal (LMVV) Bupivacaine Pilot Study

| Mouse # | LipoForm# | Conc. | Volume | mg Bup | 15 hr | 18 hr | 21 hr |
|---|---|---|---|---|---|---|---|
| 1 | 3 | 2% | 300 | 6 | 1 | 1 | 10 |
| 2 | 3 | 2% | 300 | 6 | 1 | 1 | 0 |
| 1 | 4 | 1% | 450 | 4.5 | 1 | 1 | 0 |
| 2 | 4 | 1% | 450 | 4.5 | 1 | 1 | 0 |
| 1 | 5 | 2% | 300 | 6 | 1 | 1 | 0 |
| 2 | 5 | 2% | 300 | 6 | 0 | 1 | 0 |

The results of Table 9A-9C and FIGS. 5A-5C and 6A-6F show clearly the large superiority of all liposomal BUP (more than 8 hours for all liposomal 1-8 groups, in some of groups (#1, 2, 3, 4, 5, 7, 8 even 12 hours of) over free BUP in which there is a complete disappearance of analgesia in less then 2 hours post administration. Comparing the performance of the different liposomal-BUP formulations (described in Table 8) formulation 4, where BUP was actively loaded into LMVV via transmembrane CA gradient and the stored at iso-osmotic aqueous saline provided the longest analgesia effect. However the differences from the other formulations (#1, 2, 3, 5, 7, 8) was not significant especially when compared to the large increase in analgesia duration when compared to free BUP. These efficacy data are in agreement with those previously described for the unstable HSPC/CHOL LMVV formulations used by Grant et al. 2004, ibid., and U.S. Pat. No. 6,162,462].

In a separate experiment the effect of repeated injection of bupivacaine loaded LMVV in mice was evaluated. For this 3 mice were injected with 150 µl of liposomes containing 2.0% BUP and level of analgesia was determined as described in Table 9A, the results were similar to those in Table 9A. After 15 hours a second (repeated) injection was given to the same mice and the duration of analgesia was followed for another 24 hours. The results showed that the analgesia obtained after the second (repeated) injection was identical to the one achieved at the first injection without any observed side effect. The conclusion was that analgesia can be prolonged by repeated injections and the time period of analgesia after the second injection was at least of the same duration as that obtained after the first injection, namely there was no interference of the hydrogel.

Example 2: Efficacy of Hydrogels (Ca-Alginate and Chitosan-Oxalate) Encapsulating BUP Loaded LMVV The method used in Example 2 are the same as described above.

Results

Formulation Preparations and Characterization:

The following 9 different formulations were prepared: All LMVV have the lipid composition of HSPC100:C16SPM:CHOL 3:3:4 mole/mole and were remote loaded with BUP via AS gradient.

1—Bupivacaine loaded LMVV. Stored in saline at 4° C. for 16 days.
2—Alginate (VLG ALG) beads containing LMVV-BUP without free bupivacaine removal and stored at 4° C. for 4 months in 5.7% (iso-osmotic) bupivacaine (to prevent net drug leakage during storage). Before injection to mice the beads washed 10 times with 10 ml saline.
3—ALG beads containing LMVV-BUP (free drug was removed) and stored at 4° C. in saline for 16 days.
4—ALG beads containing LMVV-BUP (after removal of free drug) were stored at 4° C. in 5.7% bupivacaine for 16 days (to prevent reduction of drug to lipid ratio during storage). Before injection to mice these beads washed 10×10 ml of saline.
5—ALG beads containing LMVV-BUP stored at 4° C. in saline for 16 days. The beads were de-cross linked by 100 ul (each vial) 15 mg/ml oxalic acid (OA) before mice injection.
6—Chitosan (CHT) beads containing LMVV-BUP prepared without free bupivacaine removal and stored at 4° C. for 4 months in 5.7% bupivacaine (to prevent net drug leakage while storage). Before injection to mice the beads washed with OA and 10 times with 10 ml of saline each.
7—CHT beads contained LMVV-BUP (free drug was removed) and stored at 4° C. in saline for 16 days.
8—CHT beads contained LMVV-BUP and stored at 4° C. in saline for 16 days. The beads were de-cross linked by 100 ul 15.4 mg/ml $CaCl_2$ before mice injection.
9—Free bupivacaine 0.25%.

TABLE 10a samples characterization (analyzed before starting the experiment).

| Sample number | Free bup concentration(%) after injection through G31 syringe needle | BUP mM | PL. (mM) | BUP/PL. (mM) | Total BUP concentration (%) |
|---|---|---|---|---|---|
| 1 | 0.067 | 47.68 | 21.7 | 2.2 | 1.5 diluted to 1% |
| 2 | 0.056 | 17.0 | 14.1 | 1.21 | 0.54 |
| 3 | 0.166 | 29.57 | 15.3 | 1.93 | 0.93 |
| 4 | 0.132 | 32.39 | 18.0 | 1.8 | 1.02 |
| 5 | 0.049 | 23.21 | 13.7 | 1.69 | 0.73 |
| 6 | 0.057 | 18.48 | 12.35 | 1.5 | 0.58 |
| 7 | 0.06 | 28.21 | 12.56 | 2.25 | 0.89 |
| 8 | 0.087 | 28.21 | | | 0.89 |
| 9 | 0.25 | | | | 0.25 |

TABLE 10b samples characterization (analyzed after the experiment was finished).

| Sample number | Free bup concentration(%) after injection through G31 syringe needle | BUP mM | PL. (mM) | BUP/PL. (mM) | Total BUP concentration (%) |
|---|---|---|---|---|---|
| 1 | 0.096 | 26.8 | 14.6 | 1.8 | 0.8 |
| 2 | 0.744 | 48.8 | 16.8 | 2.9 | 1.5 |
| 3 | 0.146 | 30.8 | 16.3 | 1.88 | 0.95 |
| 5 | 0.06 | 25.9 | 14.7 | 1.76 | 0.8 |
| 6 | 0.312 | 41.8 | 17.6 | 3.2 | 1.3 |
| 7 | 0.125 | 50.2 | 23.3 | 2.1 | 1.5 |
| 8 | 0.12 | 31.5 | 15.2 | 2.1 | 0.97 |
| 9 | 0.25 | | | | 0.25 |

Note:
sample #2 and #6 had high free bupivacaine concentration.

TABLE 11

Bupivacaine release from beads' formulations at 37° C.

| sample # | time 0 % bup release | 2 hours % bup release | 4 hours % bup release | 6 hours % bup release | 15 hours % bup release | 23 hours % bup release | 24 hours % bup release |
|---|---|---|---|---|---|---|---|
| 3 | 17.8 | 19.5 | 51.2 | 65.1 | | 73.0 | 89.2 |
| 4 | 12.9 | 16.1 | 9.9 | | | | 90.4 |
| 5 | 5.9 | 23.5 | 41.8 | 50.6 | | 72.1 | 99.3 |
| 6 | 36.1 | 39.2 | 38.5 | 48.5 | | 69.23 | |
| 7 | 6.9 | 18.5 | 20.5 | 35.7 | 77.2 | 64.8 | 91.9 |
| 8 | 9.7 | 23.1 | 10.9 | 57.7 | 69.1 | | 101.2 |

Conclusion: all different HYDROGEL- LMVV-BUP formulations released the drug at 37° C. in a similar rate achieving total release after 24 hours.

TABLE 12A analgesia duration in mice

| mouse # | group # | 1 hr | 4 h | 7 hr | 10 hr | 12 hr | 14 hr | 16 hr | 18 hr | 20 hr | 22 hr | 24 hr | 26 hr | 27 hr | 28 hr | 29 hr | 30 hr | 32 hr | 34 hr | 49 hr |
|---|---|---|---|---|---|---|---|---|---|---|---|---|---|---|---|---|---|---|---|---|
| 1 | 1 | 1 | 1 | 1 | 1 | 1 | 1 | 1 | 0 | 0 | | | | | | | | | | |
| 2 | 1 | 1 | 1 | 1 | 1 | 1 | 1 | 0 | 0 | | | | | | | | | | | |
| 3 | 1 | 1 | 1 | 1 | 1 | 1 | 1 | 0 | 0 | | | | | | | | | | | |
| 4 | 1 | 1 | 1 | 1 | 1 | 1 | 1 | 0 | 0 | | | | | | | | | | | |
| 5 | 1 | 1 | 1 | 1 | 1 | 1 | 1 | 1 | 0.5 | 0 | | | | | | | | | | |
| 6 | 1 | 1 | 1 | 1 | 0 | 0 | 0 | | | | | | | | | | | | | |
| 7 | 1 | 1 | 1 | 1 | 1 | 1 | 1 | 1 | 0 | 0 | | | | | | | | | | |
| 1 | 2** | 1 | 1 | 1 | 1 | 1 | 1 | 1 | 1 | 1 | 1 | 1 | | 1 | | | 0 | | | |

TABLE 12A-continued analgesia duration in mice

| mouse # | group # | 1 hr | 4 h | 7 hr | 10 hr | 12 hr | 14 hr | 16 hr | 18 hr | 20 hr | 22 hr | 24 hr | 26 hr | 27 hr | 28 hr | 29 hr | 30 hr | 32 hr | 34 hr | 49 hr |
|---|---|---|---|---|---|---|---|---|---|---|---|---|---|---|---|---|---|---|---|---|
| 2 | 2** | 1 | 1 | 1 | 1 | 1 | 1 | 1 | 1 | 1 | 1 | 1 | 1 | | 1 | | 0 | | | |
| 3 | 2** | 1 | 1 | 1 | 1 | 1 | 1 | 1 | 1 | 1 | 0 | 0 | | | | | | | | |
| 4 | 2** | 1 | 1 | 1 | 1 | 1 | 1 | 1 | 1 | 1 | 1 | 1 | 1 | | 0.5 | | 0 | | | |
| 5 | 2** | | 1 | 1 | 1 | 1 | 1 | 1 | 1 | 0 | 0 | | | | | | | | | |
| 6 | 2** | | 1 | 0.5 | 1 | 1 | 1 | 1 | 1 | 0 | 0 | | | | | | | | | |
| 7 | 2** | dead | | | | | | | | | | | | | | | | | | |
| 1 | 3 | 1 | 1 | 1 | 1 | 1 | 1 | 1 | 1 | 0 | 0 | | | | | | | | | |
| 2 | 3 | 1 | 1 | 1 | 1 | 1 | 1 | 1 | 1 | 1 | 1 | 1 | 1 | | 1 | | 1 | 1 | 1 | 0 |
| 3 | 3 | 1 | 1 | 1 | 1 | 1 | 1 | 1 | 1 | 0 | 0 | | | | | | | | | |
| 4 | 3 | 1 | 1 | 1 | 1 | 1 | 1 | 1 | 1 | 1 | 1 | 1 | 1 | | 1 | | 1 | 1 | 1 | 0 |
| 5 | 3 | 1 | 1 | 1 | 1 | 1 | 1 | 1 | 1 | 0 | 0 | | | | | | | | | |
| 6 | 3 | 1 | 1 | 1 | 1 | 1 | 1 | 1 | 1 | 1 | 1 | 1 | 1 | | 1 | | 1 | 1 | 1 | 0 |
| 7 | 3 | 1 | 1 | 1 | 1 | 1 | 1 | 1 | 1 | 1 | 1 | 1 | 1 | | 0 | | | | | |
| 1 | 4** | dead | | | | | | | | | | | | | | | | | | |
| 2 | 4** | dead | | | | | | | | | | | | | | | | | | |
| 3 | 4** | | 1 | 1 | 1 | 1 | 1 | 1 | 1 | 1 | 1 | 1 | 1 | | 1 | | 1 | 1 | 1 | 0 |
| 4 | 4** | | 1 | 1 | 1 | 1 | 1 | 1 | 1 | 1 | 1 | 1 | 1 | | 1 | | 1 | 1 | 0 | |
| 5 | 4** | | 1 | 1 | 1 | 1 | 1 | 1 | 0 | 0 | | | | | | | | | | |
| 6 | 4** | | 1 | 1 | 1 | 1 | 1 | 1 | 1 | 1 | 1 | 1 | 1 | | 0.5 | | 0 | | | |
| 7 | 4** | | 1 | 1 | 1 | 1 | 1 | 1 | 1 | 0.5 | 0.5 | 1 | 1 | | 1 | | 0 | | | |
| 1 | 5 | 1 | 1 | 1 | 1 | 1 | 1 | 1 | 1 | 0 | 0 | | | | | | | | | |
| 2 | 5 | 1 | 1 | 1 | 1 | 1 | 1 | 1 | 1 | 1 | 0.5 | 1 | | 1 | 0 | | 0 | | | |
| 3 | 5 | 1 | 1 | 1 | 1 | 1 | 1 | 1 | 0 | 0 | | | | | | | | | | |
| 4 | 5 | 1 | 1 | 1 | 1 | 1 | 1 | 1 | 0 | 0 | | | | | | | | | | |
| 5 | 5 | 1 | 1 | 1 | 1 | 1 | 1 | 1 | 0 | 0 | | | | | | | | | | |
| 6 | 5 | 1 | 1 | 1 | 1 | 1 | 1 | 1 | 1 | 0 | 0.5 | 1 | | 0 | 0 | | | | | |
| 7 | 5 | 1 | 1 | 1 | 1 | 1 | 0.5 | 0 | 0 | | | | | | | | | | | |
| 1* | 6** | 1 | 1 | 1 | 1 | 1 | 1 | 1 | 1 | 1 | 1 | 1 | | 1 | | | | | | |
| 2* | 6** | 1 | 1 | 1 | 1 | 1 | 1 | 1 | 1 | 1 | 1 | 1 | | 1 | | 0 | 0 | | | |
| 3* | 6** | 1 | 1 | 1 | 1 | 1 | 1 | 1 | 1 | 1 | 1 | 1 | | 1 | | | | | | |
| 4 | 6** | 1 | 1 | 1 | 1 | 1 | 1 | 1 | 1 | 1 | 1 | 1 | | 1 | | | | | | |
| 5* | 6** | 1 | 1 | 1 | 1 | 1 | 1 | 1 | 0 | 0.5 | 0 | | | | | | | | | |
| 6* | 6** | 1 | 1 | 1 | 1 | 1 | 1 | 1 | 1 | 1 | 1 | 1 | | 1 | | 0 | | | | |
| 7 | 6** | 1 | 0.5 | | | | | | | | | | | | | | | | | |
| 1 | 7 | 1 | 1 | 1 | 1 | 1 | 1 | 1 | 1 | 0.5 | 0.5 | 1 | | 1 | | 1 | 1 | | 1 | 0 |
| 2 | 7 | 1 | 1 | 1 | 1 | 1 | 1 | 1 | 1 | 1 | 1 | 1 | | 1 | | 1 | 1 | | 1 | 0 |
| 3 | 7 | 1 | 1 | 1 | 1 | 1 | 1 | 1 | 1 | 1 | 1 | 1 | | 1 | | 1 | 1 | | 1 | 0 |
| 4 | 7 | 1 | 1 | 1 | 1 | 1 | 1 | 1 | 1 | 1 | 0.5 | 1 | | 1 | | 1 | 1 | | 1 | 1 |
| 5 | 7 | 1 | 1 | 1 | 1 | 1 | 1 | 1 | 1 | 1 | 1 | 1 | | 1 | | | | | | |
| 6 | 7 | 1 | 1 | 1 | 1 | 1 | 1 | 1 | 1 | 1 | 0.5 | 1 | | 1 | | 1 | 1 | | 1 | 1 |
| 7 | 7 | 1 | 1 | 1 | 1 | 1 | 1 | 1 | 1 | 1 | 1 | 1 | | 1 | | | | | | |
| 1* | 8 | 1 | 1 | 1 | 1 | 1 | 1 | 1 | 1 | 0.5 | 0 | | | | | 1 | 1 | | 1 | 0 |
| 2* | 8 | 1 | 1 | 1 | 1 | 1 | 1 | 1 | 1 | 1 | 1 | | 1 | | 1 | 1 | | 1 | 0 | |
| 3* | 8 | 1 | 1 | 1 | 1 | 1 | 1 | 1 | 1 | 1 | 1 | | 1 | | 1 | 1 | | 1 | 0 | |
| 4 | 8 | 1 | 1 | 1 | 1 | 1 | 1 | 1 | 1 | 0.5 | 1 | | 1 | | 1 | 0 | | 0 | 0 | |
| 5* | 8 | 1 | 1 | 1 | 1 | 1 | 1 | 1 | 0 | 0 | | | | | 1 | 1 | | 1 | 0 | |
| 6 | 8 | 1 | 1 | 1 | 1 | 1 | 1 | 1 | 1 | 1 | 1 | | 1 | | 0 | 0 | | | | |
| 7 | 8 | 1 | 1 | 1 | 1 | 1 | 1 | 1 | 1 | 1 | 0 | | 1 | | 0 | 0 | | | | |

1 = analgesia; 0 = no analgesia; 10 = partial analgesia;
*irritation at injection site;
**toxic from the free bup

TABLE 12B (group 9 only (contiuation of Table 12A)

standard free bupivacaine (group 9)

| mouse # | 0.25% bup | 5' | 30' | 60' | 75' | 90' | 105' | 120' | 135' | 150' |
|---|---|---|---|---|---|---|---|---|---|---|
| 1 | 300 ul | 1 | 1 | 1 | 1 | 1 | 0 | 0 | | |
| 2 | 300 ul | 1 | 1 | 1 | 0 | 0 | | | | |
| 3 | 300 ul | 1 | 1 | 1 | 0 | 0 | | | | |
| 4 | 300 ul | 1 | 1 | 1 | 1 | 1 | 0 | 0 | | |
| 5 | 300 ul | 1 | 1 | 1 | 1 | 1 | 1 | 0.5 | 0 | 0 |

TABLE 13

Toxic and side effects in mice

| formulation | storing solution* | effects descriptions |
|---|---|---|
| 1-LMVV | saline | no mortality, no abnormal clinical signs, no obvious side effects. |
| 2-ALG-bupigel | 5.7% bup | induced severe systemic toxicity with appearance of convulsions within 2 min after Inj. In 6 mice the damage was reversible after 1-2 hours. 1 mice died. |
| 3-ALG-bupigel | saline | no mortality, no abnormal clinical signs, no obvious side effects. |
| 4-ALG-bupigel | 5.7% bup | induced severe systemic toxicity with appearance of convulsions within 2 min after Inj. In 5 mice the damage was reversible after 1-2 hours. 2 mice died. |
| 5-ALG-bupigel & oxalic acid | saline | no mortality, no abnormal clinical signs, no obvious side effects. |
| 6-CHT-bupigel | 5.7% bup | induced severe systemic toxicity with appearance of convulsions within 2 min after Inj. In 7 mice the damage was reversible after 1-2 hours, in 5 mice: skin irritation at inj. Site was found. |
| 7-CHT-bupigel | saline | no mortality, no abnormal clinical signs, no obvious side effects. |
| 8-CHT-bupigel & CaCl2 | saline | no mortality, no abnormal clinical signs, in 4 mice: skin irritation at inj. site. |
| 2- ALG-bupigel | 0.5% bup | no mortality, no abnormal clinical signs, no obvious side effects (group of 5 mice) |

*all beads formulations were washed from the storing solutions before injection to the mice.

Control Groups:

Three control groups (5 mice per group) were studied:

The control groups aimed to check in the various formulations effects which are unrelated to bupivacaine but related to the formulation itself or to the act of injection.

The three control groups included:
1—ALG beads made of mixture 250 ul 2% ALG solution in water and 250 ul saline than cross linking by CaCl2.
2—ALG solution: mixture of 250 ul 2% ALG and 250 ul saline.
3—CHT solution: mixture of 250 ul 2% CHT and 250 ul saline. (CHT beads were very hard to pass through the needles 31G and 25G).

Mice 4 and 5 had analgesia from the ALG beads for 24 hours. Likewise, mice 3 and 4 which received chitosan sol. We have seen this phenomenon in the past, and currently we have no explanation for it.

Conclusions

All formulations (1 to 8) showed a prolonged analgesia compared with the free bupivacaine.

All different Hydrogel LMVV-BUP formulations) release the drug at 37° C. in a similar rate achieving total release after 24 hours.

TABLE 14 analgesia duration in mice, controls (300 ul injection per mice)
blank, plymers (no bup)

| mouse # | SAMPLE | 5 min | 30 min | 1 hr | 3 hr | 5 hr | 9 hr | 12 hr | 14 hr | 17 hr | 19 hr | 20 hr | 24 hr | 28 hr | 38 hr |
|---|---|---|---|---|---|---|---|---|---|---|---|---|---|---|---|
| 1 | ALG BEADS | 1 | 0 | 0 | 0 | 0 | 0 | | | | | | | | |
| 2 | ALG BEADS | 1 | 1 | 0 | 0 | 0 | 0 | | | | | | | | |
| 3 | ALG BEADS | 0 | 0 | 0 | 0 | 0 | 0 | | | | | | | | |
| 4 | ALG BEADS | 1 | 1 | 0.5 | 0.5 | 0.5 | 1 | 1 | 1 | 1 | 1 | 1 | 1 | | 0 |
| 5 | ALG BEADS | 0 | 1 | 1 | 1 | 1 | 1 | 1 | 1 | 1 | 1 | 1 | 1 | | 0 |
| 1 | ALG BEADS | | | | | | | | | | | | | 0 | |
| 2 | ALG BEADS | | | | | | | | | | | | | 0 | |
| 3 | ALG BEADS | | | | | | | | | | | | | 0 | |
| 4 | ALG BEADS | | | | | | | | | | | | | 1 | |
| 5 | ALG BEADS | | | | | | | | | | | | | 0 | |
| 1 | 1% ALG sol. | | | | | | | | | | | | | 0 | |
| 2 | 1% ALG sol. | | | | | | | | | | | | | 0 | |
| 3 | 1% ALG sol. | | | | | | | | | | | | | 0 | |
| 1 | 1% CHT sol. | 0 | 0 | 0 | 0 | 0 | 0 | | | | | | | | |
| 2 | 1% CHT sol. | 0 | 0 | 0 | 0 | 0 | 0 | | | | | | | | |
| 3* | 1% CHT sol. | 1 | 1 | 1 | 1 | 1 | 1 | 1 | 1 | 1 | 1 | 1 | 1 | | |
| 4* | 1% CHT sol. | 1 | 1 | 1 | 1 | 1 | 1 | 1 | 1 | 1 | 1 | 1 | 0.5 | 0 | |
| 5 | 1% CHT sol. | 1 | 0 | 0.5 | 0 | 0 | 0 | | | | | | | | |

All HYDROGEL-LMVV-BUP in hydrogels showed prolonged analgesia over LMVV-BUP.

Two of the CHT-LMVV-BUP (formulation 7;8) showed the highest analgesia prolongation followed closely by one of the ALG-LMVV-BUP (formulation 4) which was better than two other ALG-LMVV BUP formulations (3 & 5) followed by LMVV-BUP (formulation 1 which gave identical data to the a similar LMVV-BUP used in in vivo experiment 1 (NYU) referred to in the fig legend as LMVV-BUP (NYU), free bupivacaine (formulation 9) showed the shortest analgesia duration.

The beads of formulations 2, 4, 6 were stored at a high concentration of free bupivacaine (5.7%) in order to prevent change of drug to lipid ratio during storage. Before injection the beads were washed with cold un-buffered saline (pH=5.5). However as 5.7% bupivacaine at pH 5.5, exceeds the solubility limit which at 25° C. is below 2.9% (the mass solubility of bupivacaine at 25° C. in pH 5 is 2.9% and in pH 6 is 0.55%) bupivacaine may precipitate/crystallize. The solution of 5.7% bupivacaine in water was prepared by heating the solution close to water boiling followed by cooling to 4° C. Under such conditions no precipitation of bupivacaine occurs for few hours. In the hydrogel beads formulations 2, 4 and 6 free 5.7% bupivacaine crystallize/precipitate on the hydrogel fibers during storage at 4° C. and can not be washed by the cold saline. Therefore toxic effects in these formulations: severe systemic toxicity with appearance of convulsions within 2 min after injection. For most of the mice the damage was reversible after 1-2 hours (the time that the free bup was remained).

Side effects may be reduced by one or more of the following:
- Pre-wash of the beads with solution at lower pH (such as pH 2.0) in which solubility of bupivacaine 25° C. is 7.5%.
- Storing the LMVV-BUP at lower concentration of bupivacaine (0.5%-3%) that should not precipitate or crystallized and therefore can be washed by saline.
- use of ultra pure grade chitosan and possibly chitosan of lower viscosity to avoid or reduce irritation at the injection site in some of CHT formulations.

Without being bound by theory, it is believed that the use of LMVV encapsulated within hydrogel beads either the negatively charged polysaccharide alginate or the positively charged Chitosan, reduces the level of free drug (non liposomal) in the administered product using fast and easy washing of the beads. Intact LMVV are not released from the beads, while the free bupivacaine and even small liposomes are released. It is noted that hydrogen encapsulation did not affect drug release rate from LMVV. Chitosan, being positively charged, seems to act like a bioadhesive and probably binds to negatively charged surfaces like those of most cells, glycoproteins, cartilage etc, which may be an advantage as suggested by this preliminary study. It is known to be biocompatible.

Example 3: Scale Up of ALGINATE-Bup Loaded LMVV Beads

The following example is aimed providing:
1—Scale-up of LMVV preparation to 10 ml and 100 ml, using lipid composition of HSPC100/C16SPM/CHOLESTEROL 3/3/4 and ammonium sulfate for loading bupivacaine under iso-osmotic conditions.
2—Improve shelf life of LMVV-BUP by encapsulation of the bupivacaine loaded LMVV in cross-linked polymer hydrogel beads using low viscosity alginate (negative charge).
3—Evaluation of the efficacy of ALG-LMVV-BUP BEADS local anesthetic in mice pain model.

Methods

LMVV-BUP Preparation

The following two formulation of BUP loaded LMVV were prepared:
10 ml LMVV-BUP
100 ml LMVV-BUP Ethanolic Lipids Solution The lipids mixture as powder: HSPC-100/C16-SPM/CHOLESTEROL 3/3/4 mole ratio were dissolved in ethanol at 65 C and bath sonication at 65 C for 5 min.

TABLE 15

LMVV formulations

| Ethanol volume ml | HSPC-100 gr | C16-SPM gr | CHOLESTEROL gr |
|---|---|---|---|
| 1 (in 15 ml vile) | 0.225 | 0.225 | 0.154 |
| 10 (in 50 ml vile) | 2.25 | 2.25 | 1.54 |

Lipid Hydration

The ethanol lipids solution was added to AS solution at 65 C and mixed for 1 hour to obtain MLV.

TABLE 16

AS solution preparations

| AS volume ml | AS 285 mOs mg | mixing |
|---|---|---|
| 10 (in 50 ml vile) | 167 (127 Mm) | Shaking incubator |
| 100 (in Erlenmeyer 250 ml) | 1670 | Magnetic stirring under water bath |

LMVV Preparation

The MLV were exposed to 10 cycles of freezing in liquid nitrogen (2 min/cycle) and thawing in 65 C water bath (about 5 min/cycle). The MLV were placed in 15 ml vials.

TABLE 17

| MLV ml | 15 ml vials |
|---|---|
| 10 | 2 |
| 100 | 10 |

AS Gradient Creation

Transmembrane AS gradient were created by removal of AS from the extra liposome aqueous phase replacing it with saline.

Two methods were used:
(i) Centrifugation at condition of 2000 g or 4000 g for 5 min or 10 min at 4 c, the supernatant was removed and the pellet was washed with saline at 4 c. the washing process was repeated 7 times.
(ii) Diafiltration at 4 c using hollow cartridge 500000 NMWC cut off. (washed the AS with 10 time volume of saline)

TABLE 18

AS Gradient formation

| LMVV ml | centrifugation | diafiltration |
|---|---|---|
| 10 | 2 ml LMVV washed with 8 ml saline, repeated 7 times. | LMVV diluted with saline ×2 or ×5 washed with 200 ml or 500 ml saline |
| 100 | — | No dilution, washed with 1000 ml saline |

Bupivacaine Loading

Bupivacaine was loaded into LMVV using remote loading of performed liposomes having a trans membrane ammoniume sulfate (AS) gradient. The pellet of the LMVV-AS gradient was mixed with filtrated 5.7% BUP in pure water (285 mOsm, PH=4.1) at the volume ratio 1:4 or 1:3 during 1 hour at 65 C. The mixture was then cooled to 4 C during 1 hour and the supernatant was removed from LMVV then saline was added.

TABLE 19

| Pellet of AS grad LMVV | vials | 5.7% BUP ml |
|---|---|---|
| 10 | 50 ml | 30 ml |
| 2 × 5 | 2 × 15 ml | 2 × 20 ml |
| 10 × 10 | 10 × 50 ml | 10 × 30 ml |

Non-encapsulated bup was removed from LMVV by using two methods:
 (i) diafiltration
 (ii) washing with saline by centrifugation: this procedure was used for the 100 ml LMVV preparation.

LMVV-BUP pellet 90 ml were washed with 180 ml saline followed by 10 min centrifugation 4000 g at 4 C (using 9 of 50 ml vials). The supernatant was replaced with saline 7 times. In the last washing the saline replaced with 10 mM citrate buffer PH=5.5 in sodium chloride (the final osmotic pressure 285 mOsm) at a volume ratio 2/1 LMVV pellet/buffer.

TABLE 20

| LMVV-BUP | Dilution with saline | replaced saline volume |
|---|---|---|
| 10 | ×5 | 500 ml |
| 10 | ×2 | 250 ml |

Preparation of Alginate Beads Entrapping BUP Loaded LMVV

Alginate beads were prepared by Ca++ cross-linked alginate hydro-gel containing LMVV-BUP. For sterilization a solution of 2% (w/v) sodium alginate (ALG) was filtered through 0.2u filter. LMVV-BUP solution was centrifuged 2000 g for 5 min at 4 C and only the pellet (55.5 mM phospholipids) were used for the beads preparation. Cold 2% (w/v) sodium alginate solution and cold LMVV-BUP pellet (55.5 mM phos.) 1:1 V/V (0.2 ml ALG and 0.2 ml LMVV-BUP) mixture were dipped through a 1 ml syringe into 15 ml solution of cold 1.54% (w/v) (285 mOsm) calcium chloride. 14-17 beads were formed at 10 min gentle mechanical stirring. The beads were washed with cold saline (10 ml×3) than stored with 400 ul citrate buffer PH=5.5 solution in saline or 0.2%; 0.5%; 2% bup (adjusting osmotic pressure with sodium chloride to get 285 mOsm) at cold room (4 C).

Assays

Stability was determined from drug release rate. This was determined from the change level of free drug solution and drug to phospholipids molar ratio (D/PL) in the alginate beads at temperature 4 C, 25 C, and 37 C.

Characterization of the Beads:

Sample of beads made of 0.2 ml LMVV (pellet) and 0.2 ml 2% alginate without storing medium was injected through a #31 needle and the weight of the "broken" beads was measured. This "broken" beads were diluted ×10(w/v) with saline and free bup, total bup and total phospholipids concentration were determined. Bup was measured by HPLC (Grant et al. Parm. Res 2001 18, 336-343). Phospholipids concentration was determined by modified Bartlett method (Shmeeda et al 2003 Method Enz. 367, 272-292.

Free Bup (Non Liposomal Bup) Determination:

Aliquot of upper phase (sup) from the diluted "broken" beads after 5 min 2000 g centrifugation at 4 C followed by adding ×10 volume isopropanol (IPA) to extract the bup for HPLC determination.

Total Bup Determination:
 (I) Total: aliquot of diluted "broken" beads were heated under boil water 5 min followed by extracting the bup with ×10 volume in IPA for HPLC determination.
 (II) Total sup: aliquot of diluted 'broken" beads were heated under boil water 5 min and spin it, then aliquot from the upper phase (sup) was extracted with ×10 volume IPA for HPLC determination.

Total Phospholipids Determination:

Aliquot of 25 ul or 50 ul from diluted "broken" beads were used for Bartlett assay.

Results

Drug Release from LMVV and Beads-LMVV

Bupivacaine release from few LMVV preparations and ALG-beads was measured for different storing solution, as indicated in Table 21.

TABLE 21

LIPOSOME LMVV-BUP PREPARETION STORING SOLUTIONS AND CONDITIONS

| Storing solution | PH | Sterile conditions | Volume preparation | Drug/PL |
|---|---|---|---|---|
| Saline, 2% 0.5% bup | No buffer | − | 10 ml | 1.5 |
| Saline, 2% 0.5% bup | No buffer | − | 10 ml | 2.4 |
| Saline, 2% 0.5% bup | 5.5 | + | 10 ml | 1.45 |
| Saline, 2% 0.5% 0.2% bup | 5.5 | + | 10 ml | 1.44 |
| Saline, 2% 1% 0.5% 0.2% bup | 5.5 | + | 100 ml | 1.63 |

TABLE 22

ALGINATE LMVV-BUP BEADS PREPARATION

| Storing solution | Storing pH | Sterile condition |
|---|---|---|
| Saline, 2% 0.5% 0.2% bup | No buffer | − |
| 2% 0.5% bup | No buffer | − |
| Saline, 2% 0.5% bup | 5.5 | + |
| Saline, 2% 0.5% 0.2% bup | 5.5 | + |
| 2% bup | 5.5 | + |
| 0.5% bup | 5.5 | + |
| 0.2% bup | 5.5 | + |
| saline | 5.5 | + |
| 1% | 5.5 | + |

FIG. 9A-9H show the release profile of Bupivacaine from alginate LMVV beads at 4° C. in different storing solution. Bupivacaine Release from Alginate LMVV Beads at 37° C. and 25° C. in Different Storing Solution.

FIGS. 10A and 10B show release of BUP form beads (080209) washed from the storing (1 month) solution with saline and incubated at 37 C. FIG. 10C shows release of Bup from beads (180209) unwashed from the storing (1 month at 4° C.) solution and then incubated at 37° C. FIG. 10D shows release of BUP from beads (010609) unwashed from the storing (1 week at 4° C.) solution and then incubated at 37° C. and 25° C.

Characterization the Beads:

TABLE 23

B-ALG Aug. 02, 2009 (IMVV 29 Jan. 2009 D/L = 1.5)
After 3 months at 4 C.

| beads sample | weight | free bup (%) | total bup (%) | phos (nM) | D/L | bup in the sample |
|---|---|---|---|---|---|---|
| storing in sal | 0.302 | 0.13(0.1) | 0.91 (sup) | 30.2 | 0.99 | 2.73 |
| after washing | | | 1.29 | | 1.4 | 3.9 |
| storing in 0.5 | 0.256 | 0.23 | 1.6 | 30.9 | 1.7 | 4.1 |
| after washing | | | | | | |
| storing in 2% | 0.292 | 0.42 | 1.25 (SUP) | 25.85 | 1.59 | 3.65 |
| after washing | | | 1.8 | | 2.3 | 5.25 |

B-ALG Aug. 02, 2009 (IMVV Jan. 06, 2009 D/L = 1.63)
Beads D after 1 week at 4 c.

| samples storing in | weight gr | free bup (%) | total total bup (%) | sup total bup (%) | phos mM | D/L(total) | D/L (sup) | total bup | sup (mg)/sample |
|---|---|---|---|---|---|---|---|---|---|
| saline | 0.2884 | 0.12 | 1.15 | 1.00 | 23.20 | 1.56 | 1.35 | 3.32 | 2.88 |
| | 0.2884 | | 0.82 | 1.00 | 25.50 | 1.06 | 1.24 | 2.36 | 2.88 |
| 0.2% bup washed | 0.1906 | 0.22 | 1.29 | 1.21 | 25.27 | 1.60 | 1.50 | 2.46 | 2.31 |
| | 0.1906 | | 1.28 | 1.08 | 24.50 | 1.70 | 1.44 | 2.44 | 2.06 |
| 0.5% bup unwashed | 0.2942 | 0.33 | 1.31 | 1.28 | 23.00 | 1.78 | 1.75 | 3.85 | 3.77 |
| | 0.2942 | | 1.28 | 0.92 | 26.25 | 1.58 | 1.14 | 3.77 | 2.71 |
| 0.5% bup washed | 0.4037 | 0.20 | 1.68 | 1.46 | 17.37 | 1.51 | 1.31 | 6.78 | 5.89 |
| | 0.4037 | | 1.02 | 0.72 | 14.18 | 2.30 | 1.64 | 4.12 | 2.91 |
| 2% bup washed | 0.2896 | 0.38 | 2.09 | 1.42 | 24.53 | 2.67 | 1.80 | 6.05 | 4.11 |
| | 0.2896 | | 1.58 | 1.34 | 28.00 | 1.82 | 1.56 | 4.58 | 3.88 |
| Blank (no) bup | 0.1871 | | | | 32? 25.9 | | | | |

LMVV Jan. 06, 2009 D/L = 1.63)
Characterization of beads B, 2 weeks incubation at 37 C. and washed from the storing solution

| storing solution | weight gr | free bup | total total bup | sup total bup | phos mM | D/L(total) | D/L (sup) | Amount of sample (total) | bup (mg)/ (sup) |
|---|---|---|---|---|---|---|---|---|---|
| 0.5% bup(B) | 0.2604 | 0.19 | 0.49 | 0.27 | 24.8 | 0.64 | 0.35 | 1.27596 | 0.70308 |
| 0.5% bup(C) | 0.1891 | 0.16 | 0.38 | 0.23 | 20.9 | 0.6 | 0.35 | 0.71858 | 0.43493 |
| 2% bup (B) | 0.2457 | 0.35 | 0.56 | 0.41 | 19.8 | 0.92 | 0.68 | 1.37592 | 1.00737 |
| 2% bup (C) | 0.2535 | 0.48 | 0.61 | 0.52 | 20.1 | 0.98 | 0.84 | 1.54635 | 1.3182 |

B-ALG Jul. 4, 2009 (LMVVFeb. 4, 2009 D/L = 1.45)
After 1 month at 4 C.

| Beads sample E | weight | free pup (%) | total bup (%) | phos (mM) | D/L | Total bup in the sample |
|---|---|---|---|---|---|---|
| storing in saline unwashed | 0.39 | 0.116 | 0.86 (sup) 1.16 | 25.7 | 1.09 1.48 | 3.35 4.518 |
| storing in 0.5% bup unwashed | 0.227 | 0.38 | 1.1 (sup) 1.24 | 31.6 | 1.12 1.29 | 2.31 2.6 |
| storing in 2% bup after washing | 0.3435 | 0.51 | 1.2 (sup) 1.5 | 24.7 | 1.6 2 | 3.85 4.81 |

B-ALG Aug. 2, 2009
After 6 month at 4 C.

| sample B | weight | free pup (%) | total bup (%) | phos (mM) | D/L |
|---|---|---|---|---|---|
| In saline unwashed | 0.259 | 0.1634 | 1.12 | 30.12 | |
| washed | | 0.017 | 0.98 | 31.5 | 1.06 |
| in 0.5% bup unwashed | 0.2755 | 0.324 | 1.36 | 27.625 | |
| washed | | 0.022 | 1.04 | 28 | 1.21 |
| in 2% bup (washed beads) | 0.19 | 0.096 | 1.12 | 26.17 | |
| washed after injection | | 0.018 | 1.307 | | 1.623 |

TABLE 23-continued

LMVV Jan. 06, 2009 D/L = 1.63
Characterization of beads 3 weeks after incubation at 25 C. and washed (well) from the storing solution:

| storing solution | weight gr | free bup | total total bup | sup total bup | phos mM | D/L(total) | D/L (sup) | Amount of sample (total | bup (mg)/ (sup) |
|---|---|---|---|---|---|---|---|---|---|
| 0.5% BUP | 0.1994 |  | 0.93 | 0.74 | 26.45 | 1.14 | 0.92 | 1.85442 | 1.47556 |
| 2% BUP | 0.239 | 0.076 | 1.26 | 1.08 | 17.467 | 2.35 | 2.02 | 3.0114 | 2.5812 |

Chitosane Beads-LMVV Bup

Bup release from chitosane beads encapsulating Bup loaded LMVV is shown in FIG. 11E.

Analgesic Efficacy in Mouse Model

Testing for analgesia was performed by electrical stimulation of mice skin as described elsewhere (G. J. Grant et al, Pharmaceutical Research, 18, no 3, 336-343, 2001). Pain by electrical stimulation at the desired intensity was applied to the skin of shaved mice abdomen. The current generator (model S48, Grass Instruments (W. Warwick, R.I. USA) was used. Mice (male Swiss-Webster, 26±3 gr (n=8 per group) were used. The mice were shaved the hair overlying the abdomen and tested prior to injection to determine the Individual vocalization threshold of each mice. Than the mice were injected through 30G needle with 0.25 ml of one of the following formulation:

1—Alginate beads containing LMVV-BUP (010609), were stored at 4 c for 2 months in 0.5% bup, PH=5.5 (see B3). The external solution of the beads were removed before injection without washing them.

2—Alginate beads containing LMVV-BUP (010609), were stored at 4 c for 2 months in 2% bup, PH=5.5 (see B3). The external solution of the beads were removed and the beads washed (2.5 ml saline×5) before injection.

3—Alginate beads containing LMVV-BUP (010609), were stored at 4 c for 2 months in 1% bup, PH=5.5 (see B3). The external solution of the beads were removed before injection without washing them.

4—Alginate beads containing LMVV-BUP (010609), were stored at 4 c for 2 months in saline, PH=5.5 (see B3). The external solution of the beads were removed before injection without washing them.

5—LMVV-BUP (010609) were stored at 4 c for 2 months in saline PH=5.5.

6—BLANK: Aginate beads containing LMVV without bup, were stored at 4 c for 2 months in saline PH=5.5. The external solution of the beads were removed before injection.

7—FREE BUP: 0.15 ml of the clinical 0.5% BUP were injected.

The analgesia duration was than followed as specified in the experiment itself. All experiments were approved and ratified by the HUJI ethic committee.

Figure 12:
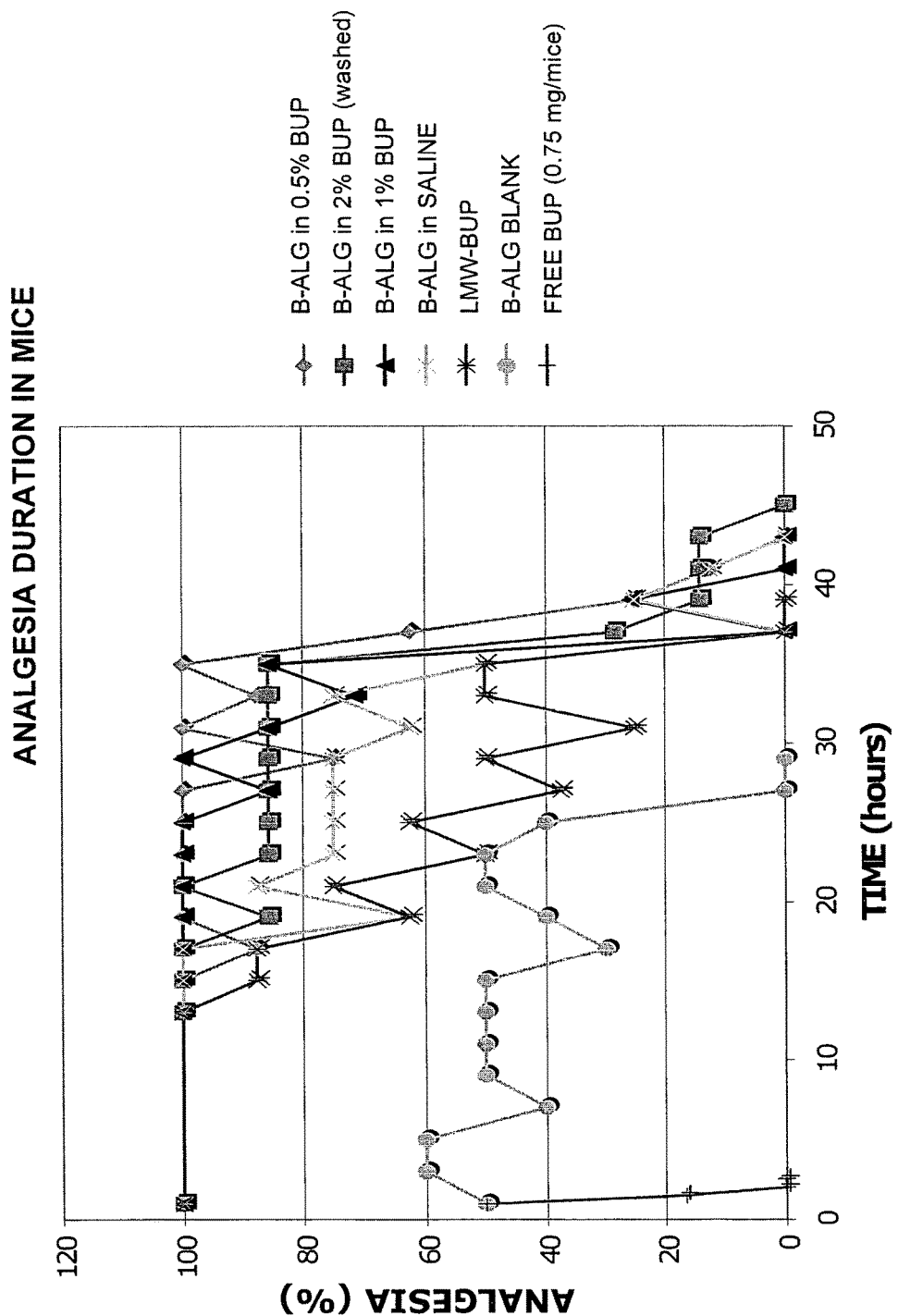
FIG. 12 compares the duration of analgesia between ALG-LMVV-BUP beads (using LMVV of HSPC100/SPM/CHOL having mole ratio of 3/3/4), remote loaded by AS gradient) stored in different liquid media (0.5%, 2%, 1% Bup solution, saline, or none (LMVV-BUP)), compared with blank ALG-Beads (without any encapsulated Bup), after 2 months storage at 4° C. and a control of 0.75% free BUP and administered after decantation of storage media.

FIG. 12 shows the analgesia duration in mice of each of the above noted formulations.

TABLE 24

FREE BUP (%) in the preparation formulations:

| SAMPLE FORMULATION | FREE BUP(%) time = 0 time of preparation | FREE BUP(%) time = 2 months Time of the in-vivo exp. |
|---|---|---|
| No 1: beads stored in 0.5% bup | 0.33 | 0.36 |
| No 2; beads stored in 2% bup (washed) | 0.38 | 0.5 |
| No 3: beads stored in 1% bup | 0.55 | 0.5 |
| No 4: beads stored in saline | 0.12 | 0.192 |
| No 5: LMVV 010609 | 0.024 | 0.038 |

TABLE 25

BUP DOSE PER MOUSE

| SAMPLE FORMULATION | FREE BUP (mg) | LIPOSOMAL BUP (mg) | TOTAL BUP (mg) |
|---|---|---|---|
| No 1: beads stored in 0.5% bup | 0.96 | 2.34 | 3.3 |
| No 2; beads stored in 2% bup (washed) | 1.13 | 1.82 | 2.95 |
| No 3: beads stored in 1% bup | 0.72 | 1.79 | 2.51 |
| No 4: beads stored in saline | 0.6 | 2.0 | 2.6 |
| No 5: LMVV 010609 | 0.684 | 3.06 | 3.75 |

The invention claimed is:

1. A composition, comprising:
1) an external storage solution having a first osmolality, comprising:
   at least one water soluble, lipid permeable active agent having a first concentration,
   wherein the at least one water soluble, lipid permeable active agent has a molecular weight of less than or equal to 500 Da, and a LogP of greater than 2.2,
   wherein the at least one water soluble, lipid permeable active agent has a molecular weight of less than or equal to 500 Da, and a LogP of greater than 2.2 is selected from the group consisting of chloroprocaine, ciprocaine, cocaine, cyclomethycaine, dimethocaine, etidocaine, propoxycaine, proparacaine, tetracaine, bupivacaine, cinchocaine, levobupivacaine, lidocaine, piperocaine, ropivacaine, dibucaine, heptacaine, mesocaine, propanocaine, carbisocaine, butacaine, betamethasone hemisuccinate and methyl prednisolone succinate; and
2) particles contained within the external storage solution, wherein the particles comprise:
   i) a water insoluble, water absorbed cross-linked polymeric matrix;

ii) liposomes contained within the water insoluble, water absorbed cross-linked polymeric matrix,
  wherein the liposomes comprise cholesterol and a phosphatidylcholine lipid having a Tm greater than or equal to 41° C.;
  wherein the liposomes have an intraliposomal aqueous compartment, containing an intraliposomal solution having a second osmolality, comprising the at least one water soluble, lipid permeable active agent having a molecular weight of less than or equal to 500 Da, and a LogP of greater than 2.2, at a second concentration;
  wherein the first osmolality is not more than 50 mOsmole higher than the second osmolality;
  wherein the second concentration is at least three times greater than the first concentration; and
  wherein the first concentration increases not more than 2 fold during storage at 4° C. for a period of at least three months.

2. The composition of claim 1, wherein the liposomes are at least one of multilamellar vesicles (MLVs) or multivesicular vesicles (MVVs).

3. The composition of claim 1, wherein the polymer of the matrix is a fully cross-linked polymer or partially cross-linked polymer.

4. The composition of claim 3, wherein the polymeric matrix is a hydrogel, the hydrogel comprises at least one cross-linked polysaccharide, the polysaccharide being selected from the group consisting of alginate and chitosan.

5. The composition of claim 1, wherein the first concentration of the at least one water soluble, lipid permeable active agent having a molecular weight of less than or equal to 500 Da, and a LogP of greater than 2.2 is between 0.2% to 2.0%.

6. The composition of claim 1, wherein the liposomes are large multivesicular vesicles (LMVV) having a diameter of between 200 nm to 25 μm.

7. The composition of claim 1, wherein the particles are administered to a subject in need thereof.

* * * * *